(12) United States Patent
Hohjoh et al.

(10) Patent No.: US 9,238,812 B2
(45) Date of Patent: Jan. 19, 2016

(54) AGENT FOR SUPPRESSING EXPRESSION OF DOMINANT MUTANT GENE

(75) Inventors: Hirohiko Hohjoh, Tokyo (JP); Masaki Takahashi, Tokyo (JP)

(73) Assignee: LSIP, LLC, Tokyo (JP)

( * ) Notice: Subject to any disclaimer, the term of this patent is extended or adjusted under 35 U.S.C. 154(b) by 0 days.

(21) Appl. No.: 13/821,299

(22) PCT Filed: Sep. 28, 2011

(86) PCT No.: PCT/JP2011/072187
§ 371 (c)(1),
(2), (4) Date: Mar. 7, 2013

(87) PCT Pub. No.: WO2012/043633
PCT Pub. Date: Apr. 5, 2012

(65) Prior Publication Data
US 2013/0197061 A1    Aug. 1, 2013

(30) Foreign Application Priority Data

Sep. 30, 2010 (JP) .................................. 2010-222847
Mar. 1, 2011 (JP) .................................. 2011-044347

(51) Int. Cl.
*A61K 31/7105* (2006.01)
*C12N 15/113* (2010.01)
*C12N 15/11* (2006.01)

(52) U.S. Cl.
CPC .......... *C12N 15/113* (2013.01); *A61K 31/7105* (2013.01); *C12N 15/111* (2013.01); *C12N 15/1135* (2013.01); *C12N 15/1138* (2013.01); *C12N 2310/14* (2013.01); *C12N 2320/11* (2013.01); *C12N 2320/34* (2013.01)

(58) Field of Classification Search
None
See application file for complete search history.

(56) References Cited

U.S. PATENT DOCUMENTS

| 2004/0192629 A1 | 9/2004 | Xu et al. |
| 2005/0272083 A1 | 12/2005 | Seshagiri |
| 2005/0288243 A1 | 12/2005 | Xu et al. |
| 2006/0147959 A1 | 7/2006 | Bell et al. |
| 2007/0031844 A1* | 2/2007 | Khvorova et al. ................. 435/6 |
| 2009/0202989 A1 | 8/2009 | Hillan |

FOREIGN PATENT DOCUMENTS

| JP | 2006505288 | 2/2006 |
| JP | 2007531525 | 11/2007 |
| JP | 2008504809 | 2/2008 |
| JP | 2008546421 | 12/2008 |
| WO | 2004/013280 A2 | 2/2004 |
| WO | 2005096781 | 10/2005 |

OTHER PUBLICATIONS

Furuya Hirokazu, et al., "A Unique Case of Fibrodysplasia Ossificans Progressiva with an ACVR1 Mutation, G356D, Other Than the Common Mutation (R206H)", American Journal of Medical Genetics Part A, vol. 146A, 2008, pp. 459-463.
Sordella, Raffaella, et al., "Gefitinib-Sensitizing EGFR Mutations in Lung Cancer Activate Anti-Apoptotic Pathways", Science, vol. 305, Aug. 20, 2004, pp. 1163-1167, with supporting online material (9 Pages).
Scherr, Michaela, et al., "Specific Inhibition of bcr-abl Gene Expression by Small Interfering RNA", Blood, Feb. 15, 2003, vol. 101, No. 4, pp. 1566-1569.
Scherr, M. et al., "Stable RNA interference (RNAi) as an option for anti-bcr-abl therapy", Gene Therapy, 2005, vol. 12, pp. 12-21.
Li, Ming-Jie, et al., "Specific Killing of Ph+ Chronic Myeloid Leukemia Cells by a Lentiviral Vector-Delivered Anti-bcr/abl Small Hairpin RNA", Oligonucleotides, 2003, vol. 13, pp. 401-409.
Wohlbold, L., et al., "All common p210 and p190 Bcr-abl Variants can be targeted by RNA interference", Leukemia, 2005, vol. 19, pp. 290-292.
Miller, Victor M., et al., "Allele-specific silencing of dominant disease genes", PNAS, Jun. 10, 2003, vol. 100, No. 12, p. 7195-7200.
Onishi, Yusuke, et al., "Establishment and Application of Method for Evaluating Allele-Specific Suppression of Expression Using RNAi", Abstract No. OA046; 54th Annual Meeting of the Japan Society of Human Genetics, 2009, pp. 1-4.
Shore, Eileen M., et al., "A recurrent mutation in the BMP type I receptor ACVR1 causes inherited and sporadic fibrodysplasia ossificans progressiva", Nature Genetics, May 2006, vol. 38, No. 5, pp. 525-527, and correction page.
Nakajima, Masahiro, et al., "The ACVR1 617G > A mutation is also recurrent in three Japanese patients with fibrodysplasia ossificans progressiva", Journal of Human Genetics, 2007, vol. 52, pp. 473-475.
Shariat, N., et al., Endocrinology, vol. 149, No. 2, p. 580-586, 2007.
Ryther, R., et al., Endocrinology, vol. 145, No. 6, p. 2988-2996, 2004.
Shinohara, T., et al., Medical Hypotheses, vol. 70, No. 2, p. 378-380, 2007.
Zhou, W., et al., Nature, vol. 462, No. 24, p. 1070-1074, 2009.
Engelman, J., et al., Journal of Clinical Investigtion, vol. 116, No. 10, p. 2695-2706, 2006.
Supplementary European Search Report issued in corresponding European Application No. 11 82 9186, Oct. 27, 2014, 4 pages.

* cited by examiner

*Primary Examiner* — Jennifer McDonald
(74) *Attorney, Agent, or Firm* — Mintz Levin Cohn Ferris Glovsky and Popeo, P.C.; David G. Conlin; Christopher R. Cowles

(57) ABSTRACT

An RNAi molecule that can selectively and effectively suppress only the expression of a particular dominant mutant gene, while permitting the expression of the wild-type gene or a desired mutant gene, and a design method thereof is presented.

6 Claims, 37 Drawing Sheets

A

B

A

Deletion mutation: del(E746 - A750)

B

A

Deletion mutation: del(L747 - T751)- L747S

B

A

Deletion & insertion mutations: del(L747 - E749)- A750P(G)

B

A

Deletion & insertion mutations:del(L747-E749)-A750P(A)

B

A
Reciprocal translocation: BCR-ABL chimeric gene

B

A

Reciprocal translocation: BCR-ABL chimeric gene

B n=4, mean±S.D.
: (p<0.01) vs. No siRNA
*: (p<0.05) vs. siControl n=4, mean±S.D.

n=4, mean±S.D.
: (p<0.01) vs. No siRNA
*: (p<0.05) vs. siControl
**: (p<0.01) vs. siControl n=4, mean±S.D.

US 9,238,812 B2

AGENT FOR SUPPRESSING EXPRESSION OF DOMINANT MUTANT GENE

RELATED APPLICATIONS

This application is a national stage application filed under 35 USC §371 of PCT/JP2011/072187, filed Sep. 28, 2011, which claims the benefit of Japanese Patent Application Nos. 2010-222847, filed Sep. 30, 2010, and 2011-044347, filed Mar. 1, 2011, both of which are incorporated herein, in entirety, by reference.

TECHNICAL FIELD

The present invention relates to an agent for suppressing the expression of a dominant mutant gene, comprising an RNAi molecule that can selectively and effectively suppress the expression of a dominant mutant gene, a pharmaceutical composition comprising the expression-suppressing agent, and a method for designing the RNAi molecule.

BACKGROUND ART

In recent years, functional nucleic acids controlling the expression of particular genes in vivo have received attention as novel pharmaceutical drugs or diagnostic drugs comparable to compounds and antibodies. Various studies and developments toward medical applications thereof are underway around the world.

The known functional nucleic acids include, for example: small interfering RNAs (siRNAs), short hairpin RNAs (shRNAs), and micro RNAs (miRNAs), which post-transcriptionally suppress the expression of target genes by gene silencing mediated by RNA interference (RNAi); nucleic acid aptamers, which suppress the functions of target substances such as transcription factors by specifically binding thereto; antisense nucleic acids, which suppress the translation of target mRNAs by binding thereto; decoy DNAs containing regulatory regions such as transcription factor-binding domains as decoy sequences, wherein the decoy DNAs capture target substances, thereby suppressing gene expression caused by the transcription factors; and U1 adaptors, which specifically inhibit polyadenylation in the mRNA precursors of target genes to destabilize the mRNA molecules and then direct the degradation thereof. All of them are expected as the next-generation pharmaceutical drugs or diagnostic drugs. Among them, RNAi by siRNAs or shRNAs is in the limelight as powerful gene expression control tools capable of suppressing the desired gene expression, because of their target specificity, wide applications, and reliable functions or effects.

Allele-specific gene silencing (or allele-specific RNAi: ASP-RNAi), which is an application of RNAi, can specifically suppress the expression of a desired allele. This technique can specifically suppress the expression of a target dominant mutant gene causative of a disease without influencing the expression of the wild-type gene and as such, is considered exceedingly useful in the therapy of the disease. For example, fibrodysplasia ossificans progressiva (FOP) known as an intractable autosomal dominantly inherited disease is caused by a point mutation that substitutes guanine (G) at position 617 by adenine (A) or a point mutation that substitutes G at position 1067 by A on its causative activin-like kinase 2 (ALK2) gene. Since a mutant gene having any of these point mutations is dominant, even a heterozygote having the wild-type ALK2 gene develops FOP (Non Patent Literatures 1 to 3). Unfortunately, an effective method for preventing the onset or progression of FOP has not yet been found. In this regard, if ASP-RNAi can suppress only the expression of a dominant mutant gene and permit the expression of the wild-type gene, the onset of autosomal dominantly inherited diseases including FOP can be prevented. In addition, the progression of these diseases can be prevented for patients who have already developed the diseases. Thus, ASP-RNAi molecules, among the RNAi molecules, are particularly highly useful as pharmaceutical drugs or diagnostic drugs.

Since such a base-substitution mutant gene having a point mutation differs from the wild-type gene in their nucleotide sequences only by one or several bases, conventional RNAi molecules based on general design methods suppress the expression of the wild-type gene due to their low specificity for the mutant gene. Even if a mutant gene has a clear difference from the wild-type gene in their nucleotide sequences, as in a dominant mutant gene that results in a transcript containing a point of discontinuity, the RNAi molecules designed by the conventional methods do not always have high specificity for the mutant gene and may often suppress the expression of the wild-type gene. Thus, the development of siRNAs or shRNAs having exceedingly high specificity for mutant genes is essential for achieving such ASP-RNAi. Nevertheless, the design of siRNAs or the like is inevitably limited by design region, because a mutation site (e.g., a substitution, deletion, or insertion site) and its neighboring nucleotide sequences must be used as the target region. Hence, the design may disadvantageously fail to constantly produce highly specific and effective siRNAs or the like, even by the application of effective methods for selecting target sequences of siRNAs known in the art.

CITATION LIST

Non Patent Literature

Non Patent Literature 1: Shore E M., et al., 2006, Nature Genetics, Vol. 38: 525-527

Non Patent Literature 2: Nakajima M., et al., 2007, Journal of Human Genetics, Vol. 52: 473-475

Non Patent Literature 3: Furuya H., et al., 2008, American Journal of Medical Genetics Part A, Vol. 146A: 459-463

SUMMARY OF INVENTION

Technical Problem

An object of the present invention is to develop an RNAi molecule that can selectively and effectively suppress only the expression of a particular target dominant mutant gene generating a point of discontinuity on a transcript, while permitting the expression of the wild-type gene or a desired dominant mutant gene, and to provide an agent for suppressing the expression of a dominant mutant gene, comprising the molecule as an active ingredient, and a method for designing the RNAi molecule.

Another object of the present invention is to provide a therapeutic agent that treats an inherited disease developed by the expression of a dominant mutant gene.

Solution to Problem

As a result of conducting diligent studies to attain the objects, the present inventors have found the general structural rule of RNAi molecules (e.g., siRNAs) capable of selectively and effectively suppressing the expression of a dominant mutant gene generating a point of discontinuity on a transcript. Specifically, an RNAi molecule having a predetermined length set as a base length from a base 3' flanking the point of discontinuity on a sense strand region to the 3' end of the sense strand region has been shown to selectively and effectively suppress the expression of the dominant mutant gene, but exhibit few or reduced suppressive effects on the expression of the wild-type gene. The present invention has been completed on the basis of these findings and provides the followings:

(1) An agent for suppressing the expression of a dominant mutant gene, comprising an RNAi molecule with an ASP score of 0.4 or higher as an active ingredient, wherein the ASP score is calculated according to the following equation:

ASP score=[(relative ratio of a normalized expression level of a normal gene treated with the RNAi molecule to a normalized expression level of the normal gene treated with a control RNAi molecule)−(relative ratio of a normalized expression level of a mutant gene treated with the RNAi molecule to a normalized expression level of the mutant gene treated with the control RNAi molecule)]×(1−the relative ratio of the normalized expression level of the mutant gene treated with the RNAi molecule to the normalized expression level of the mutant gene treated with the control RNAi molecule)

wherein the control RNAi molecule represents an RNAi molecule that does not influence the expression of the normal gene and the mutant gene, and the RNAi molecule comprises: an RNAi sense strand region comprising at least one point of discontinuity to be generated on a transcript of the targeted dominant mutant gene and a nucleotide sequence identical to a sequence of 16 to 30 consecutive bases of the transcript; and an RNAi antisense strand region comprising a nucleotide sequence complementary thereto, wherein any one of the 4th to 15th bases downstream from a base 3' flanking any one point of discontinuity on the RNAi sense strand region constitutes the 3' terminal base of the RNAi sense strand region.

(2) An agent for suppressing the expression of a dominant mutant gene, comprising an expression vector comprising an operably linked DNA encoding an RNAi molecule with an ASP score of 0.4 or higher as an active ingredient, wherein the ASP score is calculated according to the following equation:

ASP score=[(relative ratio of a normalized expression level of a normal gene treated with the RNAi molecule to a normalized expression level of the normal gene treated with a control RNAi molecule)−(relative ratio of a normalized expression level of a mutant gene treated with the RNAi molecule to a normalized expression level of the mutant gene treated with the control RNAi molecule)]×(1−the relative ratio of a normalized expression level of the mutant gene treated with the RNAi molecule to the normalized expression level of the mutant gene treated with the control RNAi molecule)

wherein the control RNAi molecule represents an RNAi molecule that does not influence the expression of the normal gene and the mutant gene, and the RNAi molecule comprises: an RNAi sense strand region comprising at least one point of discontinuity to be generated on a transcript of the targeted dominant mutant gene and a nucleotide sequence identical to a sequence of 16 to 30 consecutive bases of the transcript; and an RNAi antisense strand region comprising a nucleotide sequence complementary thereto, wherein any one of the 4th to 15th bases downstream from a base 3' flanking any one point of discontinuity on the RNAi sense strand region constitutes the 3' terminal base of the RNAi sense strand region.

(3) The suppressing agent according to (1) or (2), wherein TT or UU is further added to each of the 3' ends of the RNAi sense strand region and the RNAi antisense strand region.

(4) The suppressing agent according to any of (1) to (3), wherein the RNAi molecule is an siRNA.

(5) The suppressing agent according to any of (1) to (3), wherein the RNAi molecule is an shRNA.

(6) The suppressing agent according to any of (1) to (5), wherein the mutation in the dominant mutant gene is selected from the group consisting of a base deletion, a base insertion, a base substitution capable of destroying a splice site, a gene duplication, a gene translocation, and a chromosomal inversion.

(7) The suppressing agent according to any of (1) to (6), wherein the dominant mutant gene is a gain of function type.

(8) The suppressing agent according to any of (1) to (7), wherein the dominant mutant gene is involved in the onset of a disease.

(9) The suppressing agent according to (8), wherein the disease is malignant neoplasm.

(10) The suppressing agent according to (9), wherein the malignant neoplasm is non-small cell lung cancer, and the targeted dominant mutant gene thereof is a mutant EGFR gene; the malignant neoplasm is colon cancer, and the targeted dominant mutant gene thereof is a mutant CTNNB1 gene; the malignant neoplasm is stomach cancer, and the targeted dominant mutant gene thereof is a mutant CDH1 gene; the malignant neoplasm is breast cancer, and the targeted dominant mutant gene thereof is a mutant BRCA1 gene or a mutant BRCA2 gene; the malignant neoplasm is autoimmune polyendocrine syndrome type I, and the targeted dominant mutant gene thereof is a mutant AIRE gene; the malignant neoplasm is autoimmune lymphoproliferative syndrome, and the targeted dominant mutant gene thereof is a mutant TNFRSF6/APT1/FAS gene; the malignant neoplasm is chronic myeloid leukemia or acute lymphocytic leukemia, and the targeted dominant mutant gene thereof is a BCR-ABL chimeric gene; the malignant neoplasm is Burkitt's lymphoma, and the targeted dominant mutant gene thereof is a c-myc-IgH chimeric gene; the malignant neoplasm is anaplastic large cell lymphoma, and the targeted dominant mutant gene thereof is a NPM-ALK chimeric gene; the malignant neoplasm is lung cancer, and the targeted dominant mutant gene thereof is an EML4-ALK chimeric gene; the malignant neoplasm is dermatofibrosarcoma protuberans, and the targeted dominant mutant gene thereof is a PDGFB-COL1A1 chimeric gene; the malignant neoplasm is congenital fibrosarcoma, and the targeted dominant mutant gene thereof is an ETV6-NTRK3 chimeric gene; the malignant neoplasm is low-grade fibromyxoid sarcoma, and the targeted dominant mutant gene thereof is a FUS-CREB3L2 chimeric gene; the malignant neoplasm is extraskeletal myxoid chondrosarcoma, and the targeted dominant mutant gene thereof is an EWS-CHN chimeric gene; the malignant neoplasm is Ewing's sarcoma or desmoplastic small cell tumor, and the targeted dominant mutant gene thereof is a chimeric gene whose translocation partner is EWSR1 gene; the malignant neoplasm is alveolar rhabdomyosarcoma, and the targeted dominant mutant gene thereof is a chimeric gene whose translocation partner is SYT gene or SSX gene; the malignant neoplasm is inflammatory myofibroblastic tumor, and the targeted dominant mutant gene thereof is a chimeric gene whose translocation partner is ALK gene; the malignant neoplasm is liposarcoma, and the targeted dominant mutant gene thereof is a chimeric gene whose translocation partner is CHOP gene; or the malignant neoplasm is clear cell sarcoma of soft tissue or malignant fibrous histiocytoma, and the targeted dominant mutant gene thereof is a chimeric gene whose translocation partner is ATF1 gene.

(11) The suppressing agent according to (10), wherein the malignant neoplasm is non-small cell lung cancer, and the targeted dominant mutant gene thereof is a mutant EGFR gene.

(12) The suppressing agent according to (11), wherein the sense strand region of the RNAi molecule consists of a nucleotide represented by SEQ ID NO: 3, 5, 7, 9, 11, 13, 15, 17, 19, 21, 29, 31, 33, 35, 37, 39, 41, 43, 45, 47, 49, 53, 55, 59, 61, 63, 65, 67, 129, 131, 133, 135, 137, 139, 141, 143, or 145.

(13) The suppressing agent according to (10), wherein the malignant neoplasm is chronic myeloid leukemia or acute lymphocytic leukemia, and the targeted dominant mutant gene thereof is a BCR-ABL chimeric gene.

(14) The suppressing agent according to (13), wherein the sense strand region of the RNAi molecule consists of a nucleotide represented by SEQ ID NO: 97, 99, 101, 103, 105, 107, 109, 111, or 113.

(15) The suppressing agent according to (8), wherein the disease is a disease caused by a human autosomal dominant mutation.

(16) The suppressing agent according to (15), wherein the disease caused by a human autosomal dominant mutation is congenital night blindness, and the targeted dominant mutant gene thereof is RHO gene; the disease caused by a human autosomal dominant mutation is deafness nonsyndromic autosomal dominant 2 (DFNA2), and the targeted dominant mutant gene thereof is KCNQ4 gene or GJB gene; the disease caused by a human autosomal dominant mutation is Waardenburg's syndrome, and the targeted dominant mutant gene thereof is MITF gene; the disease caused by a human autosomal dominant mutation is nonsyndromic deafness, and the targeted dominant mutant gene thereof is DIAPH1/DFNA1 gene or POU4F3 gene; the disease caused by a human autosomal dominant mutation is hypertrophic cardiomyopathy, and the targeted dominant mutant gene thereof is TNNT2 gene; the disease caused by a human autosomal dominant mutation is familial hypertrophic cardiomyopathy, and the targeted dominant mutant gene thereof is MYBPC3 gene; the disease caused by a human autosomal dominant mutation is apical hypertrophic cardiomyopathy, and the targeted dominant mutant gene thereof is TNNI3 gene; the disease caused by a human autosomal dominant mutation is Charcot-Marie-Tooth disease type 1A, and the targeted dominant mutant gene thereof is PMP22 gene; the disease caused by a human autosomal dominant mutation is Charcot-Marie-Tooth disease type 1B, and the targeted dominant mutant gene thereof is MPZ gene; the disease caused by a human autosomal dominant mutation is long QT syndrome, and the targeted dominant mutant gene thereof is KCNQ1 gene, KCNH2 gene, SCN5A gene, ANK2 gene, KCNE1 gene, KCNE2 gene, KCNJ2 gene, CAV3 gene, SCN48 gene, AKAP9 gene, or ANTA1 gene; the disease caused by a human autosomal dominant mutation is short QT syndrome, and the targeted dominant mutant gene thereof is KCNH2 gene or KCNJ2 gene; the disease caused by a human autosomal dominant mutation is Brugada syndrome, and the targeted dominant mutant gene thereof is SCN5A gene, GPD1L gene, CACNA1C gene, CACNB2B gene, or SCN1B gene; the disease caused by a human autosomal dominant mutation is catecholaminergic polymorphic ventricular tachycardia, and the targeted dominant mutant gene thereof is RYR2 gene; the disease caused by a human autosomal dominant mutation is cardiac conduction disorder, and the targeted dominant mutant gene thereof is SCN5A gene or SCN1B gene; the disease caused by a human autosomal dominant mutation is amyotrophic lateral sclerosis, and the targeted dominant mutant gene thereof is TDP43 gene; the disease caused by a human autosomal dominant mutation is Noonan syndrome, and the targeted dominant mutant gene thereof is PTPN11 gene; or the disease caused by a human autosomal dominant mutation is hypocalcemia, and the targeted dominant mutant gene thereof is CaR gene.

(17) The suppressing agent according to (8), wherein the disease is myotonic dystrophy, and the targeted dominant mutant gene thereof is DMPK gene; the disease is spinal muscular atrophy, and the targeted dominant mutant gene thereof is SMN1 gene; the disease is congenital myasthenic syndrome, and the targeted dominant mutant gene thereof is CHRNE gene; the disease is frontotemporal dementia, and the targeted dominant mutant gene thereof is MAPT gene; or the disease is isolated growth hormone deficiency type II, and the targeted dominant mutant gene thereof is GH1 gene.

(18) A pharmaceutical composition comprising at least one suppressing agent according to any of (1) to (17) as an active ingredient.

(19) The pharmaceutical composition according to (18) dependent on (11) or (12), further comprising, as an active ingredient: an RNAi molecule whose sense strand region consists of a nucleotide represented by SEQ ID NO: 83 or 85, and/or an expression vector comprising an operably linked DNA encoding the RNAi molecule; and/or an RNAi molecule whose sense strand region consists of a nucleotide represented by SEQ ID NO: 89, and/or an expression vector comprising an operably linked DNA encoding the RNAi molecule.

(20) An agent for suppressing the expression of a point mutant EGFR gene, comprising an RNAi molecule whose sense strand region consists of a nucleotide represented by SEQ ID NO: 89, and/or an expression vector comprising an operably linked DNA encoding the RNAi molecule.

(21) A method for designing an RNAi molecule selectively suppressing the expression of a dominant mutant gene generating a point of discontinuity on a transcript, the method comprising the steps of: (a) selecting bases 5' and 3' flanking the point of discontinuity on the transcript as first and second reference bases, respectively; (b) selecting the 3' terminal base of an RNAi sense strand such that the 3'-terminal base corresponds to any one of the 4th to 15th bases downstream from the base corresponding to the second reference base on the transcript; (c) selecting a nucleotide sequence as an RNAi sense strand region, the nucleotide sequence comprising 16 to 30 consecutive bases comprising the first and second reference bases in the transcript from the dominant mutant gene; and (d) selecting a nucleotide sequence as an RNAi antisense strand region, the nucleotide sequence comprising a nucleotide sequence complementary to the selected nucleotide sequence of the RNAi sense strand region.

(22) The design method according to (21), further comprising the step of (e) screening for an RNAi molecule with an ASP score of 0.4 or higher, wherein the ASP score is calculated according to the following equation:

ASP score=[(relative ratio of a normalized expression level of a normal gene treated with the RNAi molecule to a normalized expression level of the normal gene treated with a control RNAi molecule)−(relative ratio of a normalized expression level of a mutant gene treated with the RNAi molecule to a normalized expression level of the mutant gene treated with the control RNAi molecule)]×(1−the relative ratio of the normalized expression level of the mutant gene treated with the RNAi molecule to the normalized expression level of the mutant gene treated with the control RNAi molecule)

wherein the control RNAi molecule represents an RNAi molecule that does not influence the expression of the normal gene and the mutant gene.

(23) The design method according to (21) or (22), wherein TT or UU is further added to each of the 3' ends of the RNAi sense strand region and the RNAi antisense strand region.

The present specification encompasses the contents described in the specifications and/or drawings of Japanese Patent Application Nos. 2010-222847 and 2011-044347 on which the priority of the present application is based.

Advantageous Effects of Invention

The agent for suppressing the expression of a dominant mutant gene according to the present invention is capable of selectively and effectively suppressing the expression of a target dominant mutant gene without largely influencing the expression of the wild-type gene or a dominant mutant gene other than the target.

The method for designing the RNAi molecule serving as an active ingredient in the agent for suppressing the expression of a dominant mutant gene according to the present invention can provide a highly applicable design method capable of designing an RNAi molecule against every disease-causative dominant mutant gene generating a point of discontinuity on a transcript.

The pharmaceutical composition of the present invention is capable of curing an inherited disease by selectively suppressing the expression of a target dominant mutant gene causative of the disease while maintaining the expression of the wild-type gene.

BRIEF DESCRIPTION OF DRAWINGS

149 amino acid sequence) and a deletion mutant EGFR gene del(L747-T751)-L747S (SEQ ID NO: 154 nucleotide sequence; SEQ ID NO: 153 amino acid sequence). The boxed region in the nucleotide sequence of the wild-type EGFR gene (SEQ ID NO: 150) corresponds to the deleted region in the mutant EGFR gene. A position corresponding to a point of discontinuity on a transcript of this mutant gene is indicated by arrowhead.

FIG. 23A shows the results about the PC3 cells. FIG. 23B shows the results about the PC9 cells. FIG. 23C shows the results about the HeLa cells. In each diagram, the values are indicated as relative values with the survival activity of their respective untreated cells as 100%.

FIG. 24A shows the results about the PC3 cells treated with the siRNA. FIG. 24B shows the results about the PC9 cells treated with the siRNA. FIG. 24C shows the results about the HeLa cells treated with the siRNA. In each diagram, the values are indicated as relative values with the survival activity of their respective untreated cells as 100%.

FIG. 28A shows nude mice in the 3rd week (9 weeks old) after administration of an siRNA or the like to a tumor (indicated by arrow) derived from subcutaneously transplanted PC3 cells. FIG. 28B shows PC3 cell-derived tumors excised from each population (involving 5 mice) in the 3rd week (9 weeks old) after administration of an siRNA or the like.

FIG. 31A shows total bilirubin level in plasma. FIG. 31B shows direct bilirubin level in plasma. FIG. 31C shows indirect bilirubin level in plasma. FIG. 31D shows alkaline phosphatase level in plasma. siEgfr represents EGFR-siRNA having the constitution of a conventional siRNA.

DESCRIPTION OF EMBODIMENTS

Figure 1:
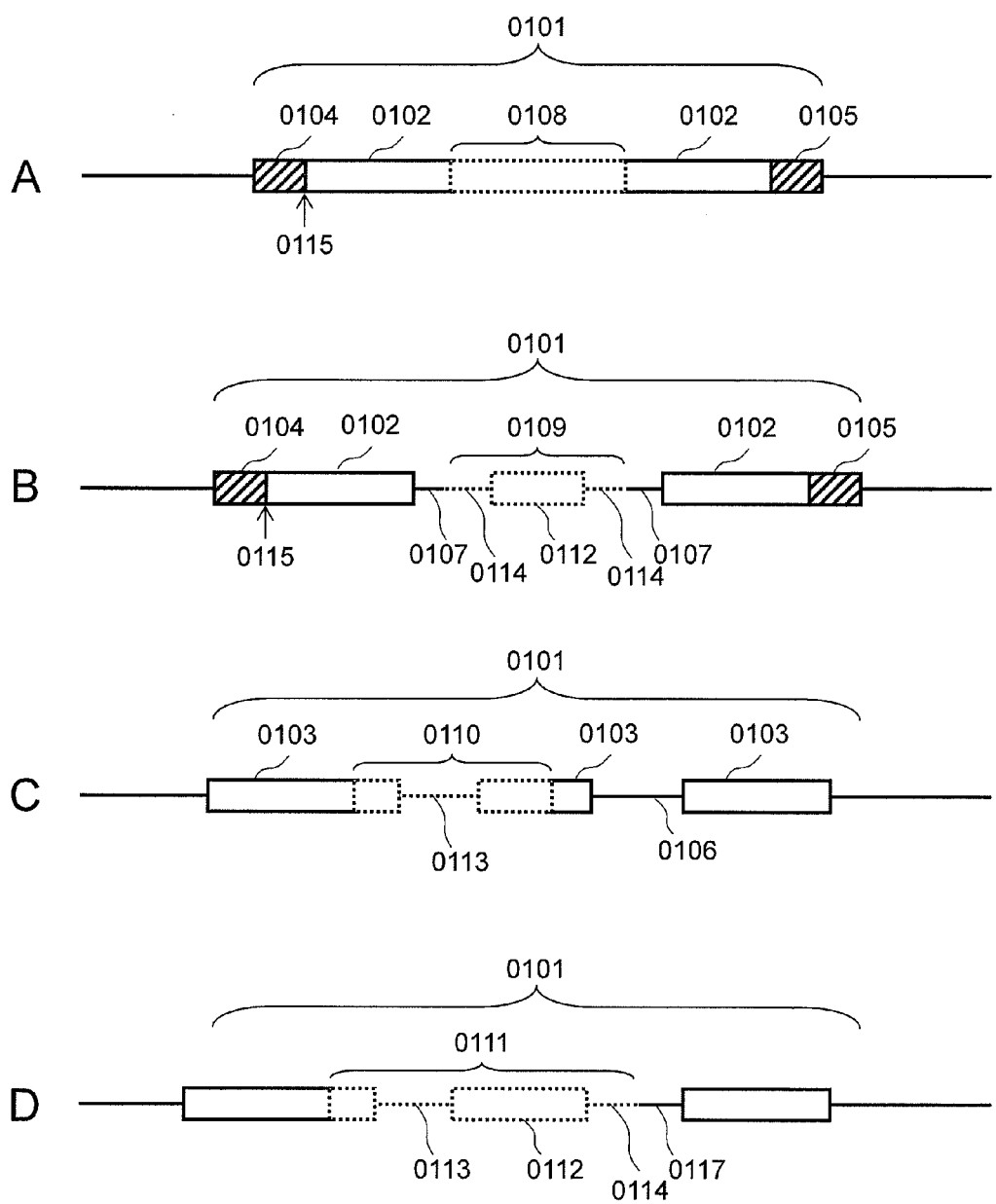
FIG. 1 is a conceptual diagram illustrating the type of a deletion mutation. The open box indicated by solid line (0102 or 0103) represents an intra-exon coding region (0102) of a gene (0101) or the whole or a portion (0103) of an exon. The diagonally shaded box indicated by solid line (0104 or 0105) represents the untranslated region (5' untranslated region: 0104; 3' untranslated region: 0105) of the gene. The solid line (0106 or 0107) between boxes represents the whole (0106) or a portion (0107) of an intron. The region indicated by broken line is a deleted region (0108, 0109, 0110, or 0111). The open box indicated by broken line (0108 or 0112) represents a deleted region (0108) in the intra-exon coding region of the gene or a deleted exon (0112). The broken line (0113 or 0114) between boxes represents the whole (0113) or a portion (0114) of a deleted intron. The arrow (0115) represents a transcription initiation point.

1. Agent for Suppressing Expression of Dominant Mutant Gene 1-1. Summary

The first embodiment of the present invention provides an agent for suppressing the expression of a dominant mutant gene. The suppressing agent of the present invention comprises an RNAi molecule and/or an expression vector encoding the RNAi molecule as an active ingredient and selectively suppresses the expression of a dominant mutant gene.

1-2. Constitution of RNAi Molecule and Definition

In the present specification, the "RNAi molecule" refers to a molecule that is capable of inducing RNA interference in vivo to post-transcriptionally and pre-translationally suppress (silence) the expression of a targeted dominant mutant gene via the degradation of the gene transcript. The RNAi molecule may be single-stranded or double-stranded as long as the molecule can suppress the gene expression of interest through the RNAi mechanism. Examples thereof include double-stranded molecules such as small interfering RNAs (siRNAs), and single-stranded molecules such as short hairpin RNAs (shRNAs) and micro RNAs (miRNAs). For the RNA interference, see, for example, Bass B. L., 2000, Cell, 101, 235-238; Sharp P. A., 2001, Genes Dev., 15, 485-490; Zamore P. D., 2002, Science, 296, 1265-1269; and Dernburg, A. F. & Karpen, G. H., 2002, Cell, 111, 159-162. In the present specification, hereinafter, the post-transcriptional gene silencing mediated by the RNAi mechanism is referred to as the "suppression of gene expression".

In the present specification, the RNAi molecule consists of a nucleic acid. In this context, the "nucleic acid" refers to a natural nucleic acid, a non-natural nucleic acid, and/or a nucleic acid analog.

In the present specification, the "natural nucleic acid" refers to a naturally occurring biological polymer that is constituted of nucleotide units linked through phosphodiester bonds. The natural nucleic acid typically corresponds to an RNA comprising an assembly of ribonucleotides having any of the bases adenine, guanine, cytosine, and uracil, and/or a DNA comprising an assembly of deoxyribonucleotides having any of the bases adenine, guanine, cytosine, and thymine. The RNAi molecule of the present invention is preferably composed mainly of, particularly, RNA.

In the present specification, the "non-natural nucleic acid" refers to a nucleic acid comprising or consisting of a nonenatural nucleotide. In this context, the "none-natural nucleotide" refers to an artificially constructed or artificially chemically modified nucleotide that is not found in the natural world and refers to a nucleotide similar in properties and/or structure to the naturally occurring nucleotides, or a nucleotide comprising a nucleoside or base similar in properties and/or structure to naturally occurring nucleosides or bases. Examples thereof include abasic nucleoside, arabinonucleoside, 2'-deoxyuridine, α-deoxyribonucleoside, β-L-deoxyribonucleoside, and other nucleosides having sugar modification. Such nucleosides further include nucleosides having substituted pentose (2'-O-methylribose, 2'-deoxy-2'-fluororibose, 3'-O-methylribose, or 1',2'-deoxyribose), arabinose, or substituted arabinose sugar; or substituted hexose, or sugar modification resulting in an alpha anomer. The nonenatural nucleotide also includes a nucleotide containing an artificially constructed base analog or an artificially chemically modified base (modified base). Examples of the "base analog" include a 2-oxo(1H)-pyridin-3-yl group, a 5-substituted 2-oxo(1H)-pyridin-3-yl group, a 2-amino-6-(2-thiazolyl)purin-9-yl group, a 2-amino-6-(2-thiazolyl)purin-9-yl group, and a 2-amino-6-(2-oxazolyl)purin-9-yl group. Examples of the "modified base" include modified pyrimidine (e.g., 5-hydroxycytosine, 5-fluorouracil, and 4-thiouracil), modified purine (e.g., 6-methyladenine and 6-thioguanosine), and other heterocyclic bases. The non-natural nucleic acid can also include chemically modified nucleic acids or nucleic acid analogs such as methylphosphonate-type DNA or RNA, phosphorothioate-type DNA or RNA, phosphoramidate-type DNA or RNA, and 2'-O-methyl-type DNA or RNA.

In the present specification the "nucleic acid analog" refers to an artificially constructed compound similar in structure and/or properties to the natural nucleic acid. Examples thereof include a peptide nucleic acid (PNA), a peptide nucleic acid having a phosphate group (PHONA), a bridged nucleic acid or locked nucleic acid (BNA or LNA), and a morpholino nucleic acid.

The nucleic acid constituting the RNAi molecule of the present invention may be labeled at its phosphate group, sugar, and/or base, if necessary, with a labeling material for nucleic acids. Any substance known in the art can be used as the labeling material for nucleic acids. Examples thereof include radioisotopes (e.g., $^{32}$P, $^{3}$H, and $^{14}$C), DIG, biotin, fluorescent dyes (e.g., FITC, Texas, cy3, cy5, cy7, FAM, HEX, VIC, JOE, Rox, TET, Bodipy 493, NBD, and TAMRA), and luminescent materials (e.g., acridinium ester).

In the present specification, the "mutation", also called variation, refers to a physical or structural change in a nucleotide sequence on a gene or on a chromosome. The mutation includes a genetic mutation, which occurs on the gene, and a chromosomal mutation, which occurs on the chromosome. In the present specification, the mutation may be any of them as long as the mutation causes a point of discontinuity described later on a transcript of the target dominant mutant gene. Also, the mutation encompasses not only naturally occurring mutations but mutations artificially induced using, for example, a mutagen such as ethyl methanesulfonate (EMS) or N-methyl-N'-nitro-N-nitrosoguanidine and mutations introduced by a molecular genetic approach.

Examples of the type of the mutation include mutations based on a base deletion, insertion, or substitution on a gene, a gene duplication or translocation, or a chromosomal inversion.

The "deletion" refers to a mutation involving a loss of a portion of the nucleotide sequence of a wild-type gene. In this context, the "wild-type gene" refers to the most commonly naturally occurring gene in the allele population of the same type of gene, wherein a protein or a functional nucleic acid encoded thereby has its original functions. The "functional nucleic acid", also called noncoding RNA, refers to an RNA that has various functions in itself without encoding a protein. The functional nucleic acid or noncoding RNA corresponds to, for example, transfer RNAs (tRNAs), ribosomal RNAs (rRNAs), small nuclear RNAs (snRNAs), small nucleolar RNAs (snoRNAs), and micro RNAs (miRNAs). In the present invention, the number of deleted bases in a deletion site in one gene and the position of the deletion site are not particularly limited as long as the site brings about a point of discontinuity on a transcript of the deletion mutant gene. In general, approximately 1 to 50 bases, 1 to 40 bases, 1 to 30 bases, or 1 to 20 bases are deleted. For example, 70% or more, 80% or more, or 90% or more of the nucleotide sequence of the wild-type gene may be deleted as long as this scope of the deletion results in a transcript that eventually brings about a dominant mutation in an individual having the mutant gene. Examples of the deletion site in one gene include: as shown in FIG. 1A, the deletion of a transcription initiation point (0115)-free partial region (0108) (indicated by broken line) in a coding region (0102) in one exon (0101); as shown in FIG. 1B, the deletion of a transcription initiation point (0115)-free region (0109) comprising the whole region (0112) of one or more exons (the region (0109) may further comprise the whole region and/or partial region of one or more introns; in FIG. 1B, the deletion site comprises the whole region (0112)

of one exon as well as partial regions (0114) of two introns flanking the exon) in a gene containing one or more introns; as shown in FIG. 1C, the deletion of a region (0110) comprising the whole region (0113) of at least one intron and partial regions of two exons flanking the intron (i.e., a portion of the 3' sequence of the upstream exon and a portion of the 5' sequence of the downstream exon) in a gene containing one or more introns; and as shown in FIG. 1D, the deletion of a region comprising a portion of the 3' sequence of an upstream exon and a portion of the 5' sequence of an intron positioned downstream of the exon (the region may further comprise the whole regions of one or more other exons and introns positioned therebetween; in FIG. 1D, the region, i.e., the region (0111), also comprises the whole region (0112) of one exon, the whole region (0113) of one of the introns flanking the exon, and the partial region (0114) of the other intron). By contrast, the deletion of a splice site-free partial region of an intron or the deletion of the whole regions of one or more introns does not apply to the deletion of the present invention, because such a deletion does not cause the point of discontinuity on a transcript.

The "insertion" refers to a mutation involving putting one or more bases into the nucleotide sequence of the wild-type gene. In the present invention, the position of the base insertion in a gene is not particularly limited as long as this insertion is positioned in an exon. By contrast, an insertion into an intron does not cause the point of discontinuity on a transcript, because the intron is normally removed by splicing after gene expression. Hence, the insertion of the present invention does not include such a base insertion into an intron, as a rule. However, the insertion of the present invention includes even an insertion into an intron when the insertion causes a point of discontinuity on a transcript, such as: an insertion into an intron as long as this insertion destroys a splice site described later; the insertion of an enormous number of bases into an intron as long as the intron is not normally removed by splicing; and the insertion of bases resulting in a sequence corresponding to an exon so that the new exon is inserted on the spliced transcript. The number of inserted bases is not particularly limited. For example, one base may be inserted, as described above. Alternatively, hundreds of bases or more such as transposon may be inserted.

The "substitution" refers to a mutation involving the replacement of base(s) in the wild-type gene by different base(s). In the comparison between a wild-type gene and a mutant gene, typically, the substitution mutation does not cause a gap in the nucleotide sequences of both the genes and their transcripts. Hence, typically, a substitution other than a substitution capable of destroying a splice site cannot cause the point of discontinuity on a transcript of the gene. By contrast, the substitution capable of destroying a splice site causes the point of discontinuity on a transcript, i.e., a gap between the nucleotide sequences of the transcripts from the wild-type gene and the mutant gene, as described later, as a result of inhibiting the splicing-mediated removal of an intron placed under the control of the splice site on the transcript. Thus, the substitution according to the present invention is directed only to the substitution capable of destroying a splice site. In this context, the splice site refers to a site necessary for normal splicing in a gene sequence. In the case of, for example, pre-mRNA splicing, general sites positioned at predetermined sites within introns apply thereto, such as a 5' splice site (donor site) positioned close to the 5' end of an intron, a 3' splice site (acceptor site) positioned close to the 3' end of an intron, and a blanch point positioned within an intron. In addition, the splice site according to the present invention also encompasses other intra-intron bases or intra-exon bases necessary for splicing. In the case of tRNA splicing or self-splicing, a base that is necessary for splicing and essential for confirmation in an RNA sequence applies to the splice site. The number of substituted bases is not particularly limited as long as the substitution can destroy a splice site. For example, the substitution may be the point mutation (single-base substitution) of any base essential for pre-mRNA splicing, such as guanine (G) in the 5' splice site.

The "duplication" refers to a mutation involving the presence of a plurality of identical genes in a chromosome. The gene duplication typically takes place due to the duplication of a partial region in the chromosome containing the genes. The duplication according to the present invention is directed to a duplication by which only a portion of a gene is duplicated to thereby generate a point of discontinuity on a transcript from the gene.

The "translocation" refers to a mutation involving the positional change of a gene or a portion of a chromosome within the same chromosome or onto a different chromosome. The translocation according to the present invention is directed to a translocation by which a portion of a gene is moved to a different position to thereby generate a point of discontinuity on a transcript comprising the translocated portion of the gene. For example, a chimeric gene resulting from the translocation, i.e., a gene comprising two or more different genes partially fused, generates a point of discontinuity on its transcript compared with any transcript of each gene used in the fusion.

The "inversion" refers to a mutation involving the reversed orientation of a portion of a chromosome. The inversion according to the present invention is directed to an inversion by which the orientation of a portion of a gene is reversed to thereby generate a point of discontinuity on a transcript comprising the portion of the gene with the reversed orientation.

The "mutant gene" refers to a gene comprising a base different from the corresponding base in the nucleotide sequence of the wild-type gene. The mutant gene according to the present invention includes a mutant gene congenitally occurring on a chromosome and a postnatally acquired mutant gene. The mutant gene does not have to exist in all cells constituting an individual and may exist in only some (or a portion) of cells, tissues, or organs. Examples thereof include mutant genes that do not exist in normal cells but exist only in cancer cells in one individual.

In the present specification, the "dominant mutant gene" refers to a mutant gene from which a trait is preferentially manifested as a phenotype in the individual. The presence or absence of the activity of a protein or a functional RNA encoded by the mutant gene is not limited as long as the mutant gene eventually brings about the abnormal phenotype as a dominant phenotype in the individual. The dominant mutant gene may have, for example, any of gain of function and loss of function mutations. The gain of function mutation includes: a hypermorph mutation resulting in a trait that exhibits increased amount (overexpression) or increased activity (constitutive activity or hyperactivity) of a protein; a neomorph mutation resulting in a trait that exhibits novel functional activity; and an antimorph mutation (dominant negative) resulting in the suppressed exhibition of a trait of a wild-type gene because the gene product antagonizes or suppresses a protein derived from the wild-type gene. Examples of the loss of function mutation include: an amorph mutation by which the gene is completely unable to express its trait; and a hypomorph mutation by which the gene is less able to express its trait. The loss of function mutation is typically recessive. In the present specification, the loss of function mutation is directed only to a mutation producing dominant effects. The dominant mutation is preferably the gain of function mutation.

In the present specification, the "point of discontinuity" refers to the junction between bases on a transcript of a mutant gene, wherein at this junction, the continuity of bases identical between the mutant gene transcript and the wild-type gene transcript is lost due to the presence of a gap of at least one or more bases (this gap may be positioned at the end portion of the nucleotide sequence of the transcript) in the comparison of the nucleotide sequence of the mutant gene transcript with the nucleotide sequence of the wild-type gene transcript. The transcript of one mutant gene may have one or more points of discontinuity.

Figure 2:
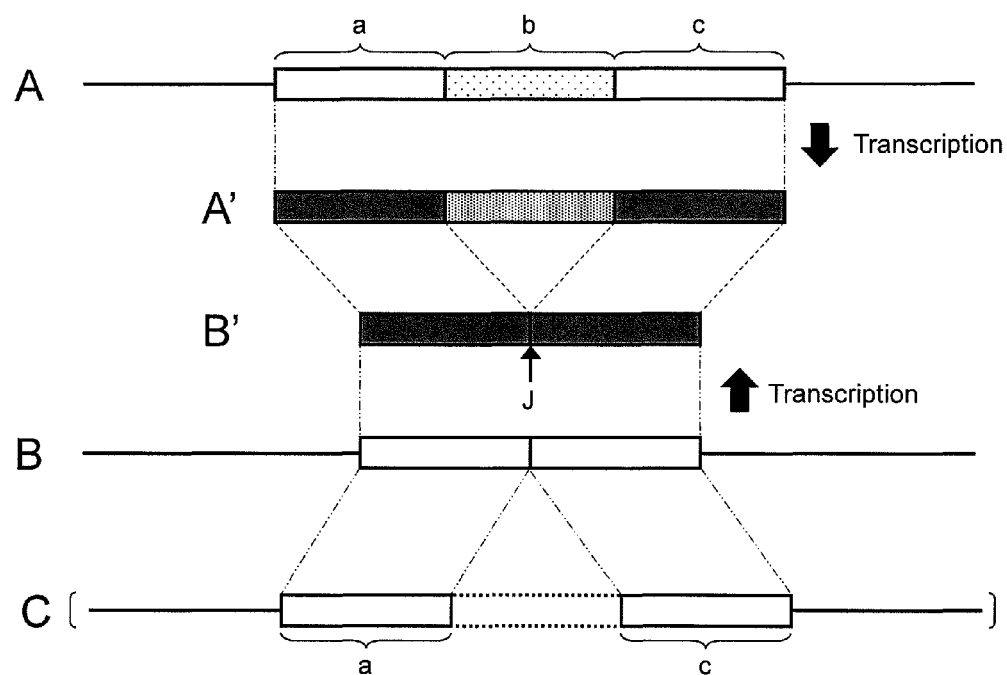
FIG. 2 is a conceptual diagram (1) illustrating a point of discontinuity caused by a deletion mutation. A represents a wild-type gene. A' represents a transcript of the wild-type gene. B represents a mutant gene. B' represents a transcript of the mutant gene. C indicates the deleted region (region b) by broken line in the comparison of the mutant gene B with the wild-type gene A. In this diagram, the junction (J) between regions a and c on the transcript B' serves as a point of discontinuity.

This discontinuity is based on a mutation in the mutant gene. The mutation may be, for example, a base deletion in one exon as shown in FIG. 2. In this case, in the comparison between the nucleotide sequences of transcript B' of mutant gene B in which region b in wild-type gene A is deleted and wild-type gene transcript A', the nucleotide sequences of regions a and c are identical therebetween. The continuity, however, is lost between the 3'-terminal base of the region a and the 5'-terminal base of the region c in the wild-type gene transcript. In this case, the junction (J) between the 3'-terminal base of the region a and the 5'-terminal base of the region c in the mutant gene transcript B' serves as a point of discontinuity.

Figure 3:
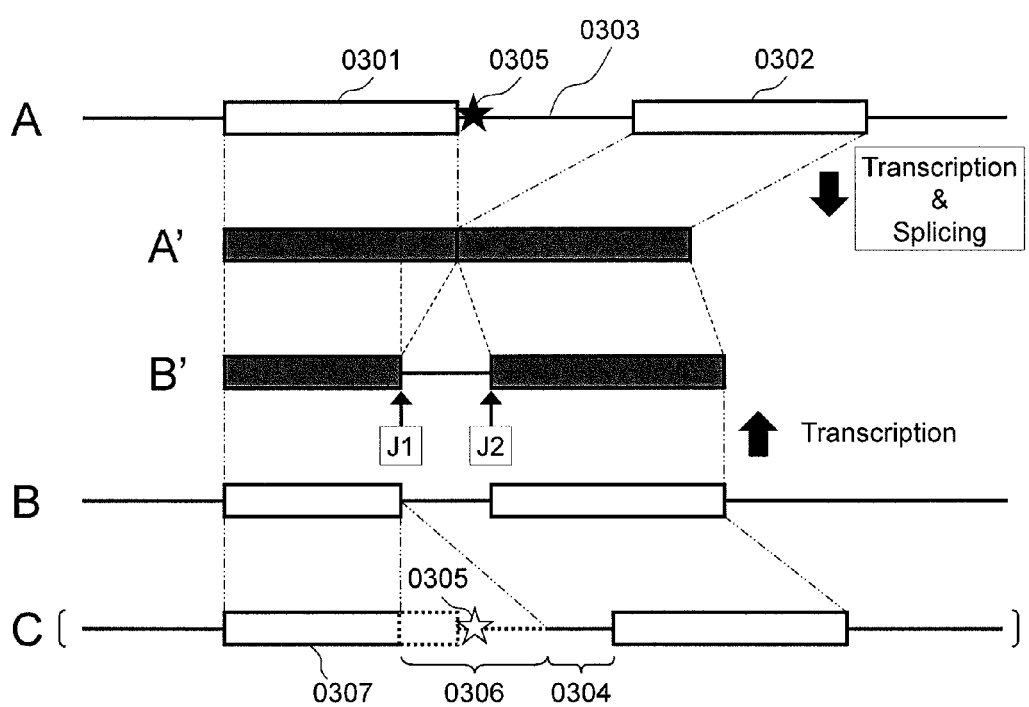
FIG. 3 is a conceptual diagram (2) illustrating a point of discontinuity caused by a deletion mutation. A represents a wild-type gene. A' represents a transcript of the wild-type gene. B represents a mutant gene. B' represents a transcript of the mutant gene. The open box indicated by solid line (0301 or 0302) represents an exon. The solid line (0303 or 0304) between boxes represents the whole (0303) or a portion (0304) of an intron. The asterisk (0305) represents a 5' splice site. The region indicated by broken line (0306) is a deleted region in the mutant gene. In this diagram, two junctions in the transcript B' of the mutant gene serve as points of discontinuity: the junction (J1) between a region derived from a portion (0307) of exon 1 (0301) and a region derived from a portion (0304) of the intron; and the junction (J2) between the region derived from a portion (0304) of the intron and a region derived from exon 2 (0302).

Alternatively, as shown in FIG. 3, the deletion in the mutant gene B (see C in which the deletion site is indicated by broken line) may be of a region (0306) consisting of one or some 3-terminal bases of exon 1 (0301) and one or some 5'-terminal bases of intron 1 (0303). In this case, the 5' splice site (0305) is deleted in the mutant gene B to thereby inhibit the pre-mRNA splicing-mediated removal of intron 1. The resulting transcript B' contains the remaining bases (0304) at the 3' end of intron 1 (0303). In the comparison between the nucleotide sequences of this transcript B' and transcript A' of wild-type gene A, the continuity is lost between a base immediately upstream of the deleted 3' end of exon 1 (0301) on the 5' side and the 5'-terminal base of exon 2 (0302) on the 3' side. Thus, in this case, two junctions serve as points of discontinuity: junction (J1) between a base immediately upstream of the deleted 3' end of exon 1 (0301) and a base immediately downstream of the deleted 5' end of 5'-terminally truncated intron 1 (0304); and junction (J2) between the 3'-terminal base of intron 1 (0304) and the 5'-terminal base of exon 2 (0302).

Figure 4:
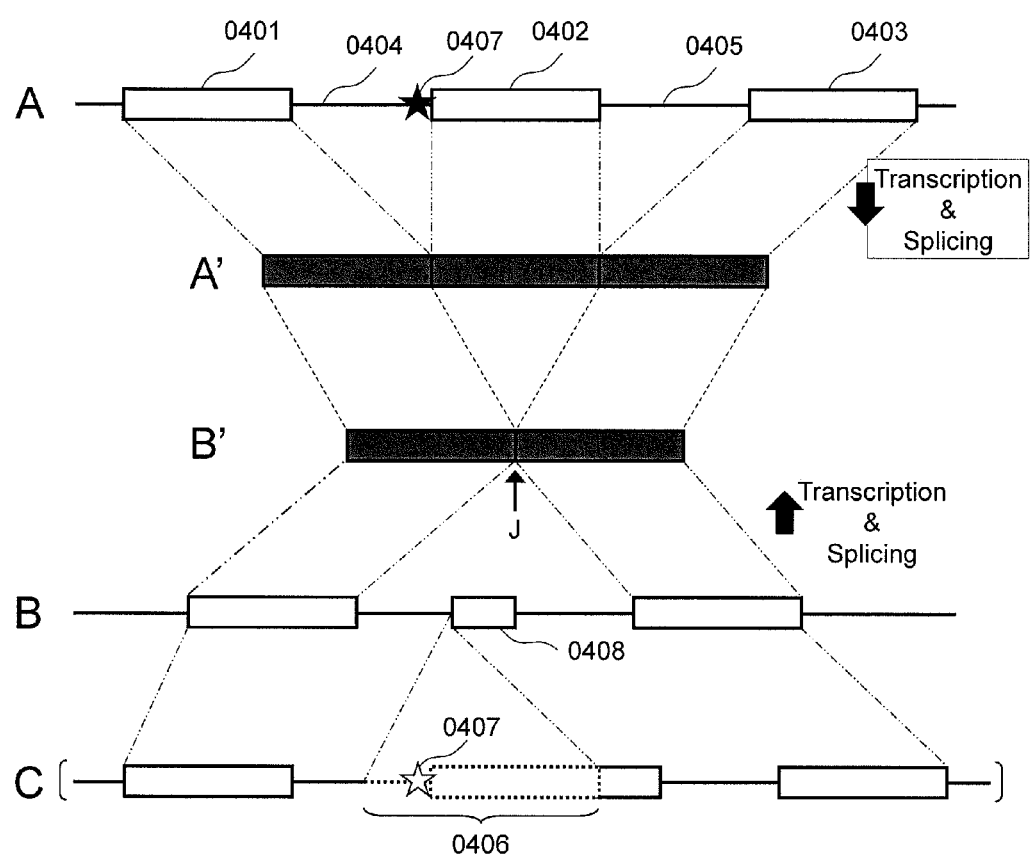
FIG. 4 is a conceptual diagram (3) illustrating a point of discontinuity caused by a deletion mutation. A represents a wild-type gene. A' represents a transcript of the wild-type gene. B represents a mutant gene. B' represents a transcript of the mutant gene. C indicates the deleted region (0406) by broken line in the comparison of the mutant gene B with the wild-type gene A. In this diagram, the junction (J) between exon 1 (0401) and exon 3 (0403) on the transcript B' of the mutant gene serves as a point of discontinuity.

Furthermore, as shown in FIG. 4, the deletion in the mutant gene B (see C in which the deletion site is indicated by broken line) may be of a region (0406) consisting of one or some 3-terminal bases of intron 1 (0404) and one or some 5'-terminal bases of exon 2 (0402). In this case, the 3' splice site (0407) of intron 1 is deleted in the mutant gene B, whereby the partial 3'-terminal region (0408) of exon 2 (0402) may be removed by splicing. The resulting transcript B' contains exon 1 (0401) linked to exon 3 (0403). In the comparison between the nucleotide sequences of this transcript B' and transcript A' of wild-type gene A, the continuity is lost between the 3'-terminal base of exon 1 (0401) and the 5'-terminal base of exon 3 (0403). Thus, in this case, the junction (J) between the 3'-terminal base of exon 1 (0401) and the 5'-terminal base of exon 3 (0403) serves as a point of discontinuity.

Figure 5:
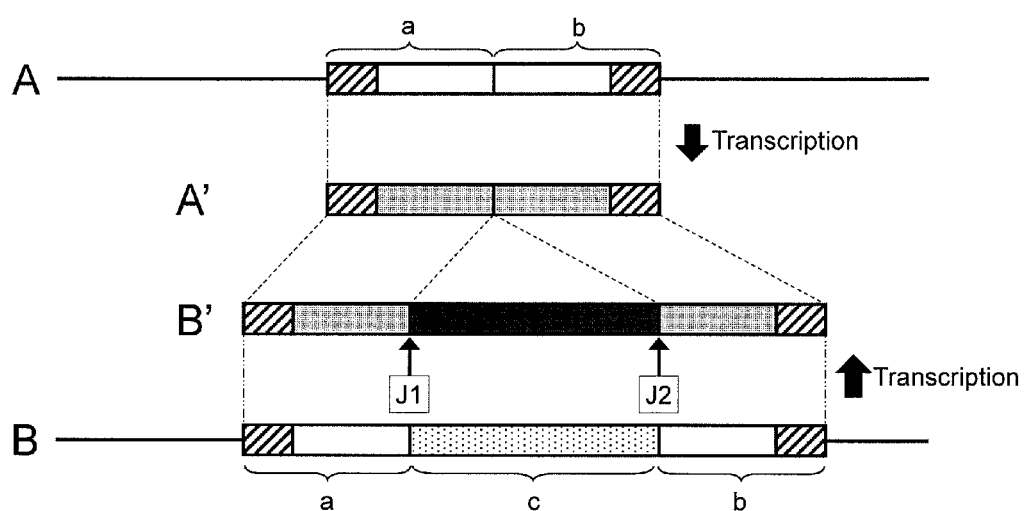
FIG. 5 is a conceptual diagram illustrating a point of discontinuity caused by an insertion mutation. A represents a wild-type gene. A' represents a transcript of the wild-type gene. B represents a mutant gene. B' represents a transcript of the mutant gene. In the diagram, the open box in each of regions a and b represents an intra-exon coding region, and the diagonally shaded box therein represents an intra-exon untranslated region. Region c (shaded box) represents an inserted portion in the mutant gene. In this diagram, two junctions (J1 and J2) in the transcript B' of the mutant gene serves as points of discontinuity: the junctions between wild-type exon-derived regions (regions a and b) and the region (region c) derived from the inserted portion.

Alternatively, as shown in FIG. 5, the mutation in the mutant gene B may be, for example, a base insertion into one exon. In this case, in the comparison between the nucleotide sequences of transcript B' of mutant gene B containing inserted region c and transcript A' of wild-type gene A, the continuity is lost between the 3' end of region a and the 5' end of region c and between the 3' end of region c and the 5' end of region b in the transcript B'. In this case, two junctions in the mutant gene transcript B' serve as points of discontinuity: junction (J1) between the 3'-terminal base of region a and the 5'-terminal base of region c; and junction (J2) between the 3'-terminal base of region c and the 5'-terminal base of region b.

In this embodiment, the type of the targeted gene and an organic species from which the gene is derived are not particularly limited. A gene encoding any protein or functional nucleic acid may be targeted by the suppressing agent of this embodiment. Also, the organism species may be any of animals and plants and encompasses any type thereof. The animal is preferably a vertebrate, more preferably fish, a bird, or a mammal. The fish is more preferably a fish species for marine resources (e.g., fish species of the families Salmonidae, Serranidae, Gadidae, Clupeidae, Paralichthyidae, Pleuronectidae, Carangidae, Ammodytidae, Sparidae, and Sebastidae). The bird is more preferably an edible species (e.g., chickens, geese, domestic ducks, ducks, mallards, turkeys, quails, and ostriches). The mammal is more preferably livestock (pigs, cattle, sheep, goats, and horses), a laboratory animal (rodents, rabbits, dogs, and monkeys), a racehorse, a pet animal (dogs, cats, rabbits, monkeys, and rodents), or a human. The organism species is further preferably a human. Alternatively, the plant is preferably a seed plant, more preferably an angiosperm, further preferably an edible plant species (e.g., edible plant species belonging to the families Poaceae (e.g., rice, wheat, barley, rye, corn, kaoliang, and millet), Leguminosae (e.g., soybean, adzuki bean, and green pea), Solanaceae (e.g., tomato, eggplant, potato, pepper, and bell pepper), Convolvulaceae (e.g., sweet potato), Rosaceae (e.g., strawberry, almond, peach, plum, Japanese apricot, rose, and cherry), Brassicaceae (e.g., radish, turnip, and rape), Chenopodiaceae (e.g., spinach and sugarbeet), Umbelliferae, Polygonaceae, Cucurbitaceae, Compositae, Liliaceae, Araceae, Vitaceae, Rutaceae, Fagaceae, and Arecaceae), a plant species for fiber resources (e.g., cotton and hemp), or a plant species for wood resources (e.g., Japanese cedar, cypress, fir, hemlock fir, pine, yew, cherry, maple, live oak, oak, beech, elm, zelkova, walnut, Japanese big-leaf magnolia, Katsura tree, teak, lauan, ebony, mahogany, poplar, and eucalyptus).

The trait in which the mutation is involved is not particularly limited and is preferably a trait whose exhibition is to be suppressed. Examples thereof include a mutation involved in the onset of a disease and a mutation involved in abnormal morphology. In this context, the disease includes, for example, a disease caused by a postnatally occurring mutation in genomic DNA within a particular cell, and a disease caused by an autosomal dominant mutation.

Examples of the disease caused by a postnatally occurring mutation in genomic DNA within a particular cell include neoplasm (tumor), particularly, malignant neoplasm (malignant tumor, i.e., so-called cancer including leukemia). Specific examples of malignant neoplasm developed by a postnatally occurring insertion or deletion in the nucleotide sequence of genomic DNA within a particular cell include: non-small cell lung cancer (NSCLC) caused by the mutation in epidermal growth factor receptor (EGFR) gene; colon cancer caused by the mutation in CTNNB1 gene; stomach cancer caused by the mutation in CDH1 gene; breast cancer caused by the mutation in BRCA1 gene or BRCA2 gene; autoimmune polyendocrine syndrome type I caused by the mutation in AIRE gene; and autoimmune lymphoproliferative syndrome caused by the mutation in TNFRSF6/APT1/FAS gene. More specific examples of malignant neoplasm developed by a postnatally occurring gene mutation involving a translocation in genomic DNA within a particular cell include: chronic myeloid leukemia (CML) and acute lymphocytic leukemia (ALL) caused by a chimeric gene of BCR gene and ABL gene; Burkitt's lymphoma caused by a chimeric gene of c-myc gene and IgH gene; anaplastic large cell lymphoma caused by a chimeric gene of NPM gene and ALK gene; lung cancer caused by a chimeric gene of EML4 gene and ALK gene; dermatofibrosarcoma protuberans caused by a chimeric gene of PDGFB gene and COL1A1 gene; congenital fibrosarcoma caused by a chimeric gene of ETV6 gene and NTRK3 gene; low-grade fibromyxoid sarcoma caused by a chimeric gene of FUS gene and CREB3L2 gene; extraskeletal myxoid chondrosarcoma caused by a chimeric gene of EWS gene and CHN gene; Ewing's sarcoma caused by a chimeric gene whose translocation partner is EWS1 gene; alveolar rhabdomyosarcoma caused by a chimeric gene whose translocation partner is SYT gene or SSX gene; inflammatory myofibroblastic tumor caused by a chimeric gene whose translocation partner is ALK gene; liposarcoma caused by a chimeric gene whose translocation partner is CHOP gene; and clear cell sarcoma of soft tissue or malignant fibrous histiocytoma caused by a chimeric gene whose translocation partner is ATF1 gene.

Examples of diseases accompanying splicing abnormality include: myotonic dystrophy caused by the mutation in DMPK gene; spinal muscular atrophy caused by the mutation in SMN1 gene; congenital myasthenic syndrome caused by the mutation in CHRNE gene; frontotemporal dementia caused by the mutation in MAPT gene; and isolated growth hormone deficiency type II caused by the mutation in GH1 gene.

Examples of diseases caused by a human autosomal dominant mutation include: congenital night blindness caused by the mutation in RHO gene; deafness nonsyndromic autosomal dominant 2 (DFNA2) caused by the mutation in KCNQ4 gene or GJB gene; Waardenburg's syndrome caused by the mutation in MITF gene; nonsyndromic deafness caused by the mutation in DIAPH1/DFNA1 gene or POU4F3 gene; hypertrophic cardiomyopathy caused by the mutation in TNNT2 gene; familial hypertrophic cardiomyopathy caused by the mutation in MYBPC3 gene; apical hypertrophic cardiomyopathy caused by the mutation in TNNI3 gene; Charcot-Marie-Tooth disease type 1B caused by the mutation in MPZ gene; Charcot-Marie-Tooth disease type 1A caused by the mutation in PMP22 gene; long QT syndrome caused by the mutation in KCNQ1 gene, KCNH2 gene, SCN5A gene, ANK2 gene, KCNE1 gene, KCNE2 gene, KCNJ2 gene, CAV3 gene, SCN48 gene, AKAP9 gene, or ANTA1 gene; short QT syndrome caused by the mutation in KCNH2 gene or KCNJ2 gene; Brugada syndrome caused by the mutation in SCN5A gene, GPD1L gene, CACNA1C gene, CACNB2B gene, or SCN1B gene; catecholaminergic polymorphic ventricular tachycardia caused by the mutation in RYR2 gene; cardiac conduction disorder caused by the mutation in SCN5A or SCN1B gene; amyotrophic lateral sclerosis caused by the mutation in TDP43 gene; Noonan syndrome caused by the mutation in PTPN11 gene; and hypocalcemia caused by the mutation in CaR gene.

1-3. Structure of RNAi Molecule

The RNAi molecule contained in the suppressing agent of this embodiment comprises: an RNAi sense strand region containing at least one point of discontinuity to be generated on a transcript of the targeted dominant mutant gene; and an RNAi antisense strand region comprising a nucleotide sequence complementary thereto.

Figure 6:
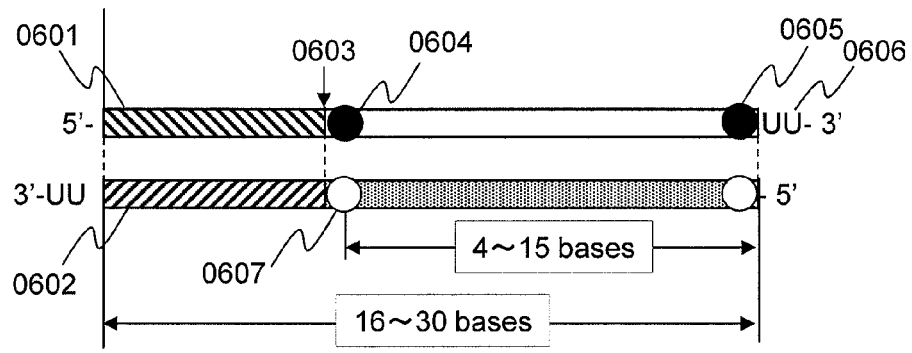
FIG. 6 is conceptual diagram showing the structure of an RNAi molecule. A double-stranded RNAi molecule (siRNA) is shown in (A), and a single-stranded RNAi molecule (shRNA) is shown in (B).
Figure 6:
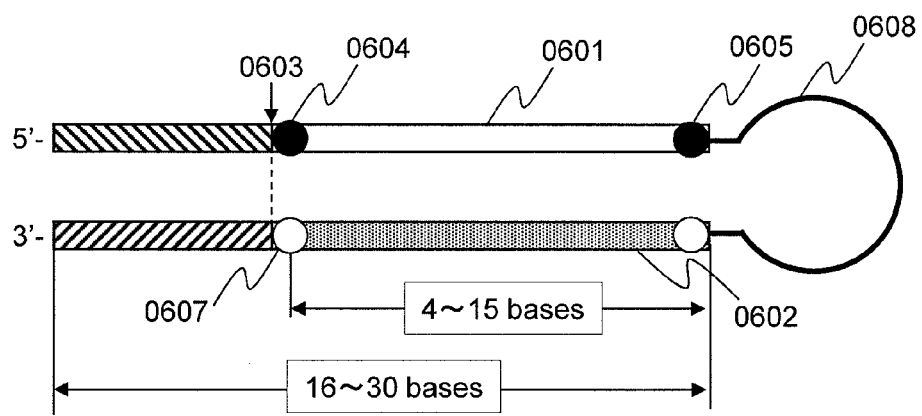

As an example, FIG. 6 is a conceptual diagram showing the structure of the RNAi molecule contained in the suppressing agent of this embodiment. As shown in this diagram, the RNAi molecule encompasses a double-stranded molecule (FIG. 6A) and a single-stranded molecule (FIG. 6B). In addition, the RNAi molecule of the present invention may include a circular molecule (e.g., a dumbbell-shaped nucleic acid) comprising the RNAi sense strand region and the RNAi antisense strand region comprising a nucleotide sequence complementary thereto.

(Component Common to RNAi Molecules)

The RNAi molecule contained, in any form, in the suppressing agent of this embodiment comprises an RNAi sense strand region (0601), an RNAi antisense strand region (0602), and a point of discontinuity (0603) as essential components. Hereinafter, these components common to RNAi molecules will be described.

The "RNAi sense strand region" (0601) comprises a nucleotide sequence identical to the nucleotide sequence of a transcript of the target dominant mutant gene and contains at least one point of discontinuity (0603) (in FIG. 6, indicated by the junction between the diagonally shaded region and the open region in the sense strand region (0601)) to be generated on the transcript. The base length of the sense strand region (0601) is 16 to 30 consecutive bases, 18 to 25 consecutive base, or 19 to 23 consecutive bases of the transcript. When a base (0604) 3' flanking the point of discontinuity (0603) is defined as a reference (which corresponds to a second reference base described later), any one of the 3rd to 16th bases, preferably the 4th to 15th bases (0605), more preferably the 4th to 13th bases, downstream from the reference base constitutes the 3'-terminal base of the RNAi sense strand region. When one transcript contains a plurality of points of discontinuity (0603), a base 3' flanking any one point of discontinuity may be selected as a reference base.

The "RNAi antisense strand region" (0602) comprises a nucleotide sequence completely complementary to the RNAi sense strand region (0601). Thus, this nucleotide sequence contains a base (0607) complementary to the reference base, i.e., the base 3' flanking the point of discontinuity (0603). In the case of the double-stranded RNAi molecule (FIG. 6A) of this embodiment, the RNAi antisense strand region is contained in another polynucleotide strand different from the polynucleotide strand comprising the RNAi sense strand region. In the case of the single-stranded molecule (FIG. 6B), the RNAi antisense strand region and the RNAi sense strand region are contained in opposite orientations in the same polynucleotide strand.

The "point of discontinuity" (0603) is described above in detail, so that the description thereof is omitted.

A feature of the RNAi molecule of this embodiment is an ASP score of 0.4 or higher. The "ASP score" (allele-specificity score) refers to allele discrimination ability, which is an important factor for ASP-RNAi, indicated in numerical form. In other words, this ASP score can also be regarded as the numerical form of the influence of nonspecific suppression of the RNAi molecule on the expression of the normal gene, i.e., the adverse reaction of the RNAi molecule on the normal gene. The ASP score is calculated according to the following equation:

ASP score=[(relative ratio of a normalized expression level of a normal gene treated with the RNAi molecule to a normalized expression level of the normal gene treated with a control RNAi molecule)−(relative ratio of a normalized expression level of a mutant gene treated with the RNAi molecule to a normalized expression level of the mutant gene treated with the control RNAi molecule)]×(1−the relative ratio of the normalized expression level of the mutant gene treated with the RNAi molecule to the normalized expression level of the mutant gene treated with the control RNAi molecule)

In the equation, the control RNAi molecule represents an RNAi molecule that is used as a negative control for the RNAi molecule serving as the active ingredient of this embodiment and does not influence the expression of the normal gene and the mutant gene. Hence, in the equation, the normalized expression level of each gene treated with the control RNAi molecule is regarded as 100%. For example, an RNAi molecule comprising an arbitrary nucleotide sequence free from the targeted gene applies to the control RNAi molecule. In the equation, when the relative ratio of the normalized expression level exceeds "1.0", this is regarded as the absence of an expression suppressive effect. In this case, "1.0" is assigned to the relative ratio for calculation.

The ASP score can reflect both "specificity" for and "suppressive effect" on the mutant gene. For example, a certain RNAi molecule with a low ASP score strongly suppresses the expression of the wild-type gene due to its low specificity, even if this RNAi molecule can strongly suppress the expression of the mutant gene. This means that the RNAi molecule has strong adverse reaction on the wild-type gene. The RNAi molecule with an ASP score of 0.4 or higher suppresses the expression of the mutant gene and also has little adverse reaction or relatively weak effects on the wild-type gene. Thus, this RNAi molecule can function in ASP-RNAi.

For the ASP score calculation, the respective expression levels of the normal gene and the mutant gene may be measured by the same method. In this case, the measurement method is not particularly limited, and any of methods known in the art may be used. These expression levels can be normalized on the basis of the expression level of an internal or external control gene insusceptible to the suppression of expression by the RNAi molecule. Preferably, the expression levels of the wild-type gene and the mutant gene are measured on the basis of the expression of a reporter (e.g., *Photinus* or *Renilla* luciferase) gene and the expression of β-galactosidase gene as a control insusceptible to the suppression of expression by the RNAi molecule, under conditions described later in Example 1 using a reporter gene expression plasmid developed by Ohnishi Y. et al. (2006, Journal of RNAi and Gene Silencing, Vol. 2: 154-160).

(Component of Double-Stranded RNAi Molecule)

The double-stranded RNAi molecule, such as an siRNA, contained in the suppressing agent of this embodiment can further comprise, as shown in FIG. 6A, optional 3'-terminal additional bases (0606) at the 3' end of each polynucleotide strand, in addition to the components RNAi sense strand region (0601), RNAi antisense strand region (0602), and point of discontinuity (0603) common to the RNAi molecules. The "3'-terminal additional bases" (0606) are constituted of two bases: thymine-thymine (TT) or uracil-uracil (UU). The RNAi molecule having these additional bases can enhance RNAi suppression efficiency (Tuschl T et al., 1999, Genes Dev, 13 (24): 3191-7).

(Component of Single-Stranded RNAi Molecule)

The single-stranded RNAi molecule, such as an shRNA, contained in the suppressing agent of this embodiment further comprises, as shown in FIG. 6B, a short spacer sequence (0608) that links the RNAi sense strand region (0601) and the RNAi antisense strand region (0602) oriented oppositely thereto, in addition to the components RNAi sense strand region (0601), RNAi antisense strand region (0602), and point of discontinuity (0603) common to the RNAi molecules. The spacer sequence can be usually an arbitrary nucleotide sequence consisting of 3 to 24 bases, preferably 4 to 15 bases. Thus, the single-stranded RNAi molecule consists of 35 bases (16×2+3) to 84 bases (30×2+24) in total. The RNAi sense strand region and the RNAi antisense strand region form base pairs with each other within the RNAi molecule, while the spacer sequence flanked thereby forms a loop structure. As a result, the whole molecule can assume a hairpin stem-loop structure. Upon introduction into a cell, the single-stranded RNAi molecule having this structure is processed into an siRNA duplex by the action of endonuclease called Dicer within the cytoplasm. The RNAi antisense strand region in the duplex is incorporated into an RNA-induced silencing complex (RISC), which can in turn suppress the post-transcriptional and pre-translational expression of the target gene through the same RNAi mechanism as in the double-stranded RNAi molecule. The RNAi sense strand region (0601) and the RNAi antisense strand region (0602) in the single-stranded molecule can further contain 3'-terminal additional bases at their respective 3' ends, as in the double-stranded RNAi molecule. An arbitrary sequence may be added to the 5' end and/or 3' end of the single-stranded molecule. For example, a nucleotide sequence capable of forming a stem-loop structure can also be added to the 5' end and/or 3' end.

1-4. Constitution of Expression Vector

In the present specification, the "expression vector" refers to a vector that serves as an active ingredient contained in the suppressing agent of the present embodiment, wherein a DNA encoding the RNAi molecule is expressibly inserted in a vector for expression.

In the case of the expression vector of this embodiment for the double-stranded RNAi molecule such as an siRNA, DNA fragments encoding the RNAi sense strand region and the RNAi antisense strand region, respectively, may be inserted to two different vectors for expression or may be inserted as DNA fragments whose expressions are independently controlled, into one vector for expression. In the case of the expression vector for the single-stranded RNAi molecule such as an shRNA, a DNA fragment encoding the single-stranded RNAi molecule may be inserted to a predetermined position in a vector for expression.

In the present specification, the "vector for expression" refers to a backbone moiety in the expression vector of this embodiment, i.e., a moiety other than the DNA fragment encoding the RNAi molecule of embodiment 1 in the expression vector of this embodiment. The type of the vector for expression is not particularly limited and is preferably a plasmid or a virus. These vectors may be selected appropriately according to a host for the introduction. In the case where the host for the introduction is, for example, a human, an expression vector known in the art can be used, for example, a virus such as adenovirus, retrovirus, lentivirus, Sendai virus, or adeno-associated virus, or a vector based on a non-viral vector. In the case where the host for the introduction is a plant, a plasmid such as a binary vector of pBI or pRI series, or a virus such as cauliflower mosaic virus (CaMV), bean golden mosaic virus (BGMV), or tobacco mosaic virus (TMV) can be used. Alternatively, in the case where the host for the introduction is *E. coli*, for example, a plasmid of pBI, pPZP, pSMA, pUC, pBR, or pBluescript series (Stratagene Corp.) can be used. In addition, expression vectors for various types of hosts commercially available from each life science manufacturer may be used.

The vector for expression can contain a regulatory region such as a promoter, an enhancer, or a terminator, or a marker region such as a selective marker gene. Their respective types are not particularly limited. Those known in the art may be selected appropriately according to the host for the introduction of the expression vector.

Examples of the promoter that is operable in *E. coli* include: lac, trp, and tac promoters; and phage-derived T7, T3, SP6, PR, and PL promoters. Examples of the promoter that is operable in yeast include yeast glycolysis gene-derived promoters, alcohol dehydrogenase gene promoter, TPI1 promoter, and ADH2-4-c promoter. Examples of the promoter that is operable in plant cells include cauliflower mosaic virus (CaMV) 35S promoter, nopaline synthase gene promoter (Pnos), *Zea mays*-derived ubiquitin promoter, rice-derived actin promoter, and tobacco-derived PR protein promoter. Examples of the promoter that is operable in insect cells include polyhedrin promoter, P10 promoter, *Autographa californica* polyhedrosis basic protein promoter, baculovirus immediate early gene 1 promoter, and baculovirus 39K delayed-early gene promoter. RNA polymerase II (Pol II) promoter or RNA polymerase III (Pol III) promoter is preferably used as a promoter that is operable in animal cells including human cells. The promoter is preferably Pol III promoter, particularly preferably, for example, U6 or H1 promoter. Alternatively, a site-specific promoter that induces gene expression only at a particular site in vivo may be used for any of these hosts. When the DNA fragments encoding the RNAi sense strand region and the RNAi antisense strand region, respectively, are inserted into two different vectors for expression, promoters used in the vectors are preferably the same as each other or different promoters having equivalent expression activities so that both the RNA strands are expressed at equivalent levels.

1-5. Design and Production of RNAi Molecule

Figure 7:
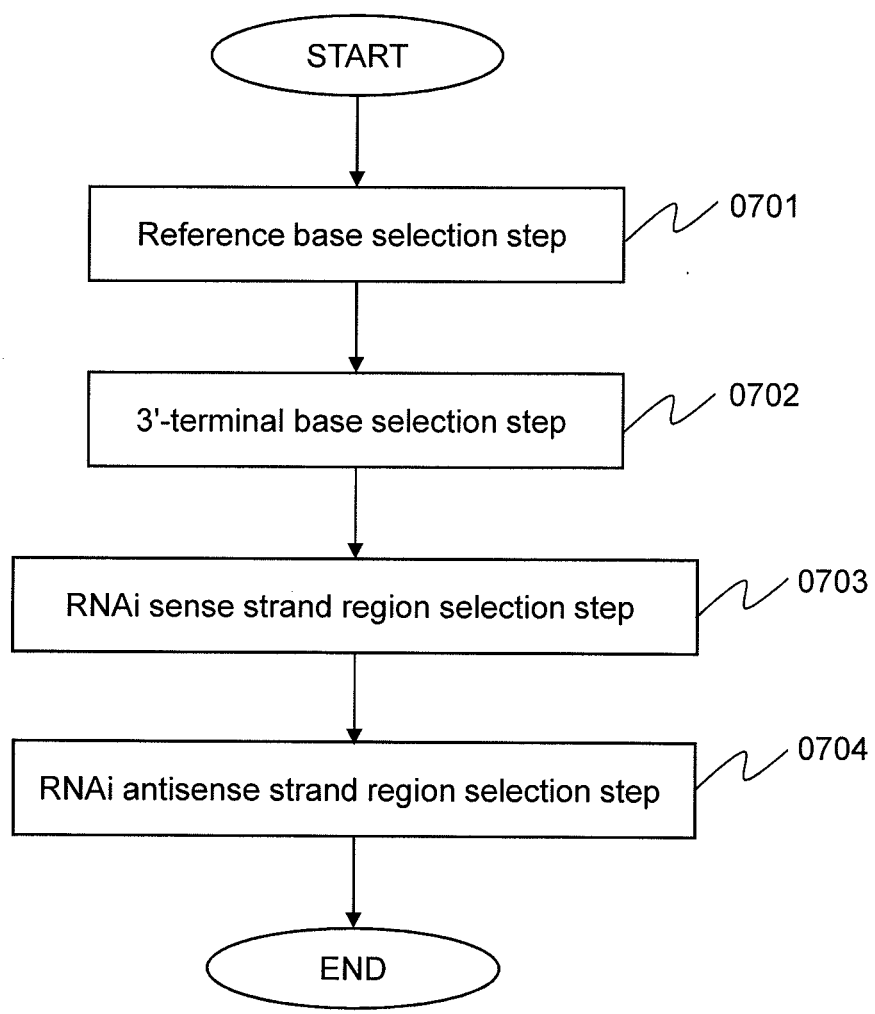
FIG. 7 is a flow chart showing a method for designing an RNAi molecule of embodiment 1.

The method for designing the RNAi molecule contained in the suppressing agent of this embodiment will be described. This design method comprises, as shown in FIG. 7, a reference base selection step (0701), a 3'-terminal base selection step (0702), an RNAi sense strand region selection step (0703), and an RNAi antisense strand region selection step (0704). Hereinafter, each step will be described.

The "reference base selection step" (0701) is the step of selecting bases 5' and 3' flanking the point of discontinuity on the transcript from the targeted dominant mutant gene as first and second reference bases, respectively. When the transcript of the dominant mutant gene contains two or more points of discontinuity, any one of the points of discontinuity is selected. In this case, bases 5' and 3' flanking the selected point of discontinuity are used as the first and second reference bases, respectively.

The "3'-terminal base selection step" (0702) is the step of selecting the 3'-terminal base of an RNAi sense strand region such that the 3'-terminal base corresponds to any one of the 4th to 15th bases, preferably the 4th to 14th bases or the 4th to 13th bases, downstream from the base corresponding to the second reference base.

The "RNAi sense strand region selection step" (0703) is the step of selecting a nucleotide sequence as an RNAi sense strand region, the nucleotide sequence comprising 16 to 30 consecutive bases comprising the first and second reference bases in the transcript from the dominant mutant gene. Since the 3'-terminal base has already been determined by the 3'-terminal base selection step, 16 to 30 bases (also including the first and second reference bases) upstream from the base corresponding to the 3'-terminal base in the nucleotide sequence of the transcript can be selected as the RNAi sense strand region. This step determines a region on the dominant mutant gene targeted by the RNAi molecule.

The "RNAi antisense strand region selection step" (0704) is the step of selecting a nucleotide sequence as an RNAi antisense strand region, the nucleotide sequence comprising a nucleotide sequence complementary to the selected nucleotide sequence of the RNAi sense strand region.

The steps described above are common to all forms (e.g., single-stranded RNAi molecule, double-stranded RNAi molecule, and circular RNAi molecule) of the RNAi molecule contained in the suppressing agent of this embodiment. Next, a 3'-terminal addition step, a spacer linking step, and an ASP score screening step will be described. A feature of the "3'-terminal addition step" is that thymine-thymine (TT) or uracil-uracil (UU) is added to each of the 3' ends of the RNAi sense strand region and the RNAi antisense strand region thus designed. This step is optional and may thus be added, if necessary, to the design method of the present invention.

The "spacer linking step" is unique and essential to the single-stranded RNAi molecule or the circular RNAi molecule. This step is the step of linking the 3' end (e.g., the 3' end of the TT- or UU-added 3' end of the RNAi sense strand region that has undergone the 3'-terminal addition step prior to this step) of the RNAi sense strand region thus designed to the 5' end of the RNAi antisense strand region (i.e., in an orientation opposite to the RNAi sense strand region) via the 5' and 3' ends, respectively, of a spacer sequence to form a single-stranded or circular RNAi molecule. The spacer sequence may be an arbitrary nucleotide sequence consisting of 3 to 24 bases, preferably 4 to 15 bases. Preferably, the nucleotide sequence does not form a base pair within the spacer sequence.

The "ASP score screening step" is the step of screening the RNAi molecules prepared by the steps described above for only an RNAi molecule with an ASP score of 0.4 or higher.

The ASP score can be calculated according to the equation described above.

The RNAi molecule of this embodiment can be synthesized by a chemical synthesis method based on the nucleotide sequence designed by the method described above. The chemical synthesis of the RNAi molecule may employ a contract manufacturing service provided by each life science manufacturer (e.g., Sigma-Aldrich Corp., Bex Co., Ltd., Takara Bio Inc., and Invitrogen Corp.). Alternatively, the nucleotide sequence designed by the method described above is temporarily converted to a DNA sequence, and a DNA chemically synthesized on the basis of the sequence can be subjected to cloning and then to an in vitro RNA transcription method known in the art to prepare the RNAi molecule of this embodiment as RNA. For the in vitro RNA transcription method, see, for example, Sambrook, J. et. al., (1989) Molecular Cloning: A Laboratory Manual Second Ed., Cold Spring Harbor Laboratory Press, Cold Spring Harbor, N.Y. Alternatively the method of Ui-Tei et al. (Nucleic Acids Res., 32: 936-948, 2004), the method of Reynolds et al. (Nat. Biotechnol., 22: 326-330, 2004), or the method of Amarzguioui et al. (Biochem. Biophys. Res. Commun., 316: 1050-1058, 2004) can be referred to.

1-6. Preparation of Expression Vector

The expression vector contained in the suppressing agent of this embodiment can be prepared basically according to a method known in the art, for example, a method described in Sambrook, J. et. al., (1989) Molecular Cloning: a Laboratory Manual Second Ed., Cold Spring Harbor Laboratory Press, Cold Spring Harbor, N.Y.

As a specific example, first, the nucleotide sequence of the RNAi molecule is determined according to the method described in the preceding paragraph "1-5. Design and production of RNAi molecule". Subsequently, a sense strand DNA and an antisense strand DNA are each synthesized by a chemical synthesis method or the like on the basis of a DNA sequence corresponding thereto. In this procedure, preferably, appropriate restriction sites are added to both ends of each strand, or the strands are modified so that appropriate cohesive ends occur after annealing. DNA synthesis may employ a contract manufacturing service provided by each life science manufacturer. Both the strands thus synthesized are mixed for annealing to prepare a double-stranded DNA fragment. Then, the restriction sites, if present at the ends, are cleaved, if necessary, with restriction enzymes appropriate therefor. The 5' end of each strand is further phosphorylated, if necessary, with T4 polynucleotide kinase or the like. Subsequently, the double-stranded DNA fragment thus prepared is linked to the corresponding restriction sites downstream of a promoter in a vector for expression. Alternatively, the DNA fragment is temporarily linked and cloned into a cloning vector, and then, a fragment cleaved therefrom may be linked to a vector for expression.

For expressing the RNAi molecule having the 3'-terminal additional bases, it should be noted that TT is inserted in advance to each of the 3' ends of the RNAi sense strand region and the RNAi antisense strand region. This step is optional and may thus be added, if necessary, to the preparation method of the present invention.

1-7. Agent for Suppressing Expression of Mutant EGFR Gene

One example of the agent for suppressing the expression of a dominant mutant gene according to this embodiment includes an agent for suppressing the expression of a mutant epidermal growth factor receptor (EGFR) gene, comprising an RNAi molecule specifically suppressing the expression of a mutant EGFR gene (this RNAi molecule is also referred to as an EGFR-RNAi molecule) as an active ingredient. In this context, the mutant EGFR gene refers to a postnatally occurring dominant mutant gene causative of non-small cell lung cancer (NSCLC). The binding of a ligand such as epidermal growth factor (EGF) to the extracellular domain of EGFR typically activates tyrosine kinase in the intracellular domain, leading to autophosphorylation. The mutant EGFR gene is thought to result from the gain of function due to a substitution, a deletion, or an insertion in the particular base of the EGFR gene to constitutively activate downstream intracellular signaling pathways (Paez G. J. et al., Science, 2004, 304; 1497-1500).

The agent for suppressing the expression of a mutant EGFR gene according to this embodiment can specifically suppress the expression of such mutant EGFR genes based on these mutations (e.g., deletion and insertion) other than the substitution.

Specific examples of the agent for suppressing the expression of a mutant EGFR gene according to this embodiment include agents for suppressing the expression of a mutant EGFR gene, comprising, as an active ingredient, an EGFR-RNAi molecule against each of del(E746-A750) mutation and del(L747-T751)-L747S mutation involving the deletion of some bases of the human EGFR gene, and del(L747-E749)-A750P mutation involving the deletion and insertion of some bases, as shown in Panel A in FIGS. 8-1, 9-1, 10-1, and 11-1. This del(L747-E749)-A750P mutation includes, as described later, two types of mutations that differ in deletion and insertion resulting in difference by one base (G or A) between nucleotide sequences, which however encode identical amino acid sequences. In the present specification, these two different del(L747-E749)-A750P mutations are distinguished, if necessary, from each other so that in the description below, the mutation having G is referred to as del(L747-E749)-A750P(G) mutation (FIG. 10-1 A) while the mutation having A is referred to as del(L747-E749)-A750P(A) mutation (FIG. 11-1 A), for the sake of convenience. More specific examples of the agent for suppressing the expression of a mutant EGFR gene include an agent for suppressing the expression of the mutant EGFR gene del(E746-A750), comprising a single-stranded or double-stranded RNAi molecule comprising a sense strand region represented by SEQ ID NO: 3, 5, 7, 9, 11, 13, 15, 17, 19, or 21, and/or an expression vector comprising an operably linked DNA encoding the RNAi molecule. Examples of the agent for suppressing the expression of the mutant EGFR gene del(L747-T751)-L747S include an agent comprising a single-stranded or double-stranded RNAi molecule comprising a sense strand region represented by SEQ ID NO: 29, 31, 33, 35, 37, 39, 41, 43, 45, 47, or 49 and/or an expression vector comprising an operably linked DNA encoding the RNAi molecule. Examples of the agent for suppressing the expression of the mutant EGFR gene del(L747-E749)-A750P(G) include an agent comprising an single-stranded or double-stranded RNAi molecule comprising a sense strand region represented by SEQ ID NO: 53, 55, 59, 61, 63, 65, or 67, and/or an expression vector comprising an operably linked DNA encoding the RNAi molecule. Alternatively, examples of the agent for suppressing the expression of the mutant EGFR gene del(L747-E749)-A750P(A) include an agent comprising a single-stranded or double-stranded RNAi molecule comprising a sense strand region represented by SEQ ID NO: 129, 131, 133, 135, 137, 139, 141, 143, or 145, and/or an expression vector comprising an operably linked DNA encoding the RNAi molecule.

1-8. Agent for Suppressing Expression of BCR-ABL Chimeric Gene

One example of the agent for suppressing the expression of a dominant mutant gene according to this embodiment includes an agent for suppressing the expression of a BCR-ABL chimeric gene, comprising an RNAi molecule specifically suppressing the expression of a BCR-ABL chimeric gene attributed to a translocation mutation in Philadelphia chromosome (this RNAi molecule is also referred to as BCR-ABL-RNAi molecule) as an active ingredient. In this context, the BCR-ABL chimeric gene refers to a postnatally occurring dominant mutant gene regarded as a causative gene of chronic myeloid leukemia (CML) or acute lymphocytic leukemia (ALL).

The Philadelphia chromosome (Ph chromosome), which is found in 90% or more of chronic myeloid leukemia (CML) cases and approximately 20% of acute lymphocytic leukemia (ALL) cases, is a tumor-specific chromosome having a structure in which a portion of chromosome 9 is translocated to chromosome 22. This translocation reciprocally translocate the ABL gene located on the long arm of chromosome 9 (9q34) and the BCR gene located on the long arm of chromosome 22 (22q11) to form a BCR-ABL chimeric gene, which eventually produce p210 or p190 protein with increased tyrosine kinase activity. The agent for suppressing the expression of a BCR-ABL chimeric gene according to this embodiment can specifically suppress the expression of such BCR-ABL chimeric genes.

Figure 12:
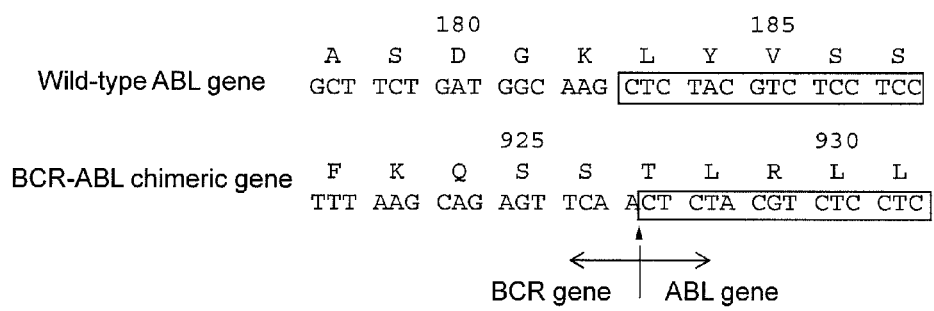
FIG. 12A is a diagram showing the comparison of a translocation site and its neighboring nucleotide sequences (and an amino acid sequence encoded thereby) between the wild-type ABL gene (SEQ ID NO: 160 nucleotide sequence; SEQ ID NO: 159 amino acid sequence) and a BCR-ABL chimeric gene resulting from Philadelphia chromosome (reciprocal translocation between the ABL gene located on the long arm of chromosome 9 (9q34) and the BCR gene located on the long arm of chromosome 22 (22q11)) (SEQ ID NO: 162 nucleotide sequence; SEQ ID NO: 161 amino acid sequence). The boxed region in the nucleotide sequence of the wild-type ABL gene (SEQ ID NO: 160) corresponds to the translocated region. The boxed region in the nucleotide sequence of the BCR-ABL chimeric gene (SEQ ID NO: 162) corresponds to a region of the ABL gene linked to the BCR gene as a result of the translocation. A position corresponding to a point of discontinuity on a transcript of this chimeric gene is indicated by arrowhead.
FIG. 12B shows the expression suppressive effects of BCR-ABL-siRNA on the non-target wild-type ABL gene and the BCR-ABL chimeric gene, wherein these effects were calculated as their respective relative values with the luciferase activity of siControl as 1.0. The luciferase activity was corrected with the expression level of β-galactosidase as an external control insusceptible to the RNAi-mediated suppression of expression.
FIG. 12C shows the ASP scores of BCR-ABL-siRNA against the non-target wild-type ABL gene and the BCR-ABL chimeric gene. The threshold (ASP score of 0.4) is indicated by broken line.
Figure 1:
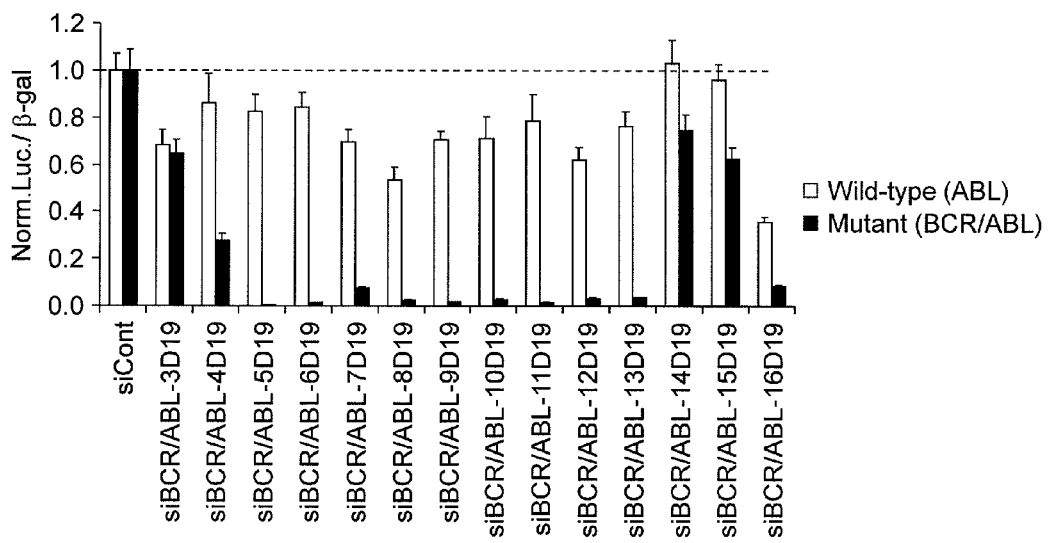
Figures 2, 12:
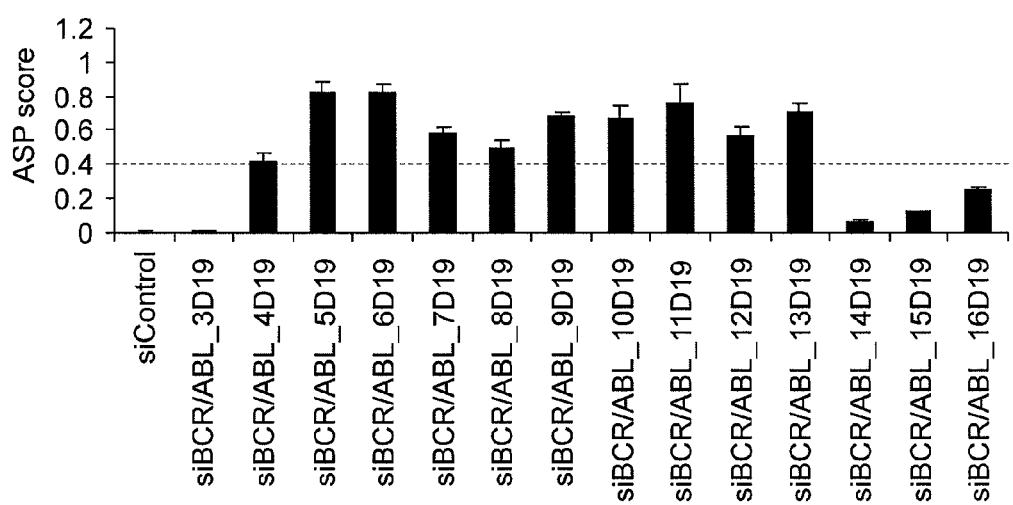
Figure 13:
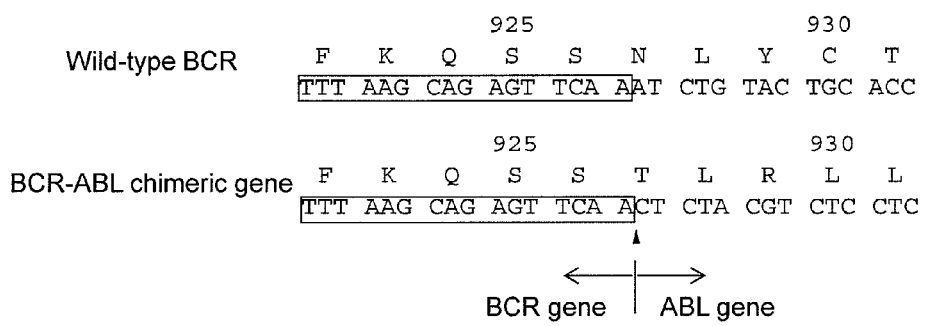
FIG. 13A is a diagram showing the comparison of a translocation site and its neighboring nucleotide sequences (and an amino acid sequence encoded thereby) between the wild-type BCR gene (SEQ ID NO: 164 nucleotide sequence; SEQ ID NO: 163 amino acid sequence) and a BCR-ABL chimeric gene resulting from Philadelphia chromosome (reciprocal translocation between the ABL gene located on the long arm of chromosome 9 (9q34) and the BCR gene located on the long arm of chromosome 22 (22q11)) (SEQ ID NO: 162 nucleotide sequence; SEQ ID NO: 161 amino acid sequence). The boxed region in the nucleotide sequence of the wild-type BCR gene (SEQ ID NO: 164) corresponds to the translocated region. The boxed region in the nucleotide sequence of the BCR-ABL chimeric gene (SEQ ID NO: 162) corresponds to a region of the BCR gene linked to the ABL gene as a result of the translocation. A position corresponding to a point of discontinuity on a transcript of this chimeric gene is indicated by arrowhead.
FIG. 13B shows the expression suppressive effects of BCR-ABL-siRNA on the non-target wild-type BCR gene and the BCR-ABL chimeric gene, wherein these effects were calculated as their respective relative values with the luciferase activity of siControl as 1.0. The luciferase activity was corrected with the expression level of β-galactosidase as an external control insusceptible to the RNAi-mediated suppression of expression.
FIG. 13C shows the ASP scores of BCR-ABL-siRNA against the non-target wild-type BCR gene and the BCR-ABL chimeric gene. The threshold (ASP score of 0.4) is indicated by broken line.
Figure 1:
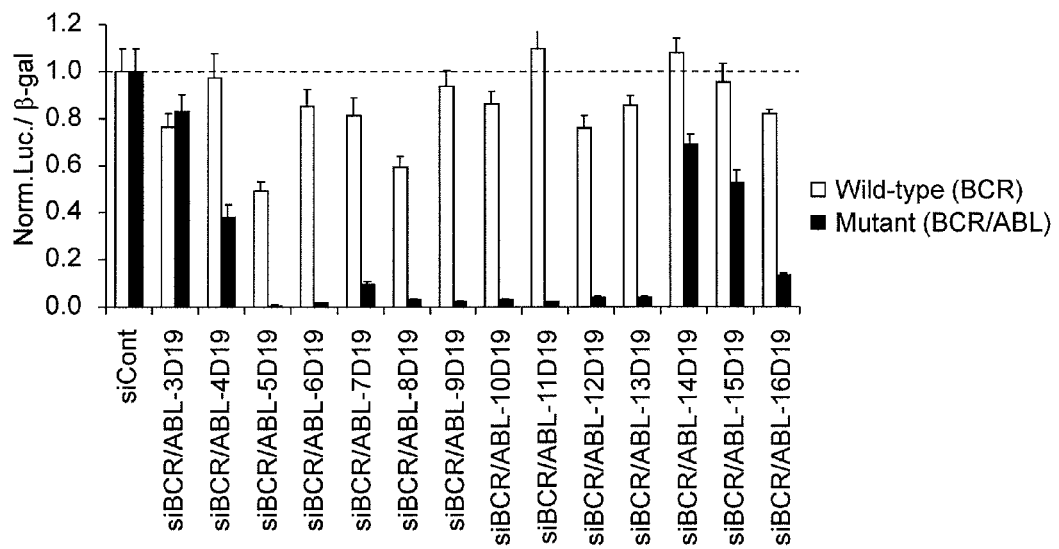
Figures 2, 13:
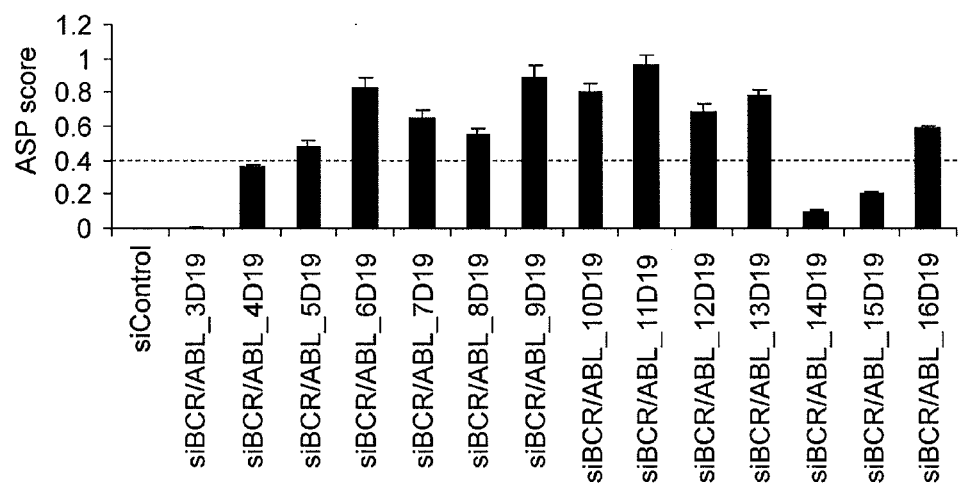

Specific examples of the agent for suppressing the expression of a BCR-ABL chimeric gene according to this embodiment include an agent for suppressing the expression of a BCR-ABL chimeric gene, comprising, as an active ingredient, a BCR-ABL-RNAi molecule against a BCR-ABL chimeric gene as shown in Panel A in FIGS. 12-1 and 13-1. More specifically, the agent for suppressing the expression of a BCR-ABL chimeric gene according to this embodiment comprises, for example, a single-stranded or double-stranded RNAi molecule comprising a sense strand region represented by SEQ ID NO: 97, 99, 101, 103, 105, 107, 109, 111, or 113, and/or an expression vector comprising an operably linked DNA encoding the RNAi molecule.

1-9. Effect

According to the gene expression-suppressing agent of this embodiment, the RNAi molecule serving as an active ingredient hardly influences the expression of a non-target gene and can selectively and efficiently suppress the expression of a target gene.

When the suppressing agent of this embodiment is introduced into a cell, the RNAi molecule serving as an active ingredient can directly act on the targeted dominant mutant gene or the RNAi molecule encoded by the DNA contained in the expression vector serving as an active ingredient can act after its expression on the targeted dominant mutant gene, thereby suppressing the expression of the dominant mutant gene by the silencing mechanism of RNAi. Thus, the suppressing agent comprising the RNAi molecule can confer its RNAi-mediated suppressive effect on the recipient cell or the like in a relatively short time. By contrast, the suppressing agent comprising the expression vector can continuously confer the effect as long as the expression vector is maintained in the cell after administration. Hence, combined use thereof can effectively suppress the expression of the dominant mutant gene.

A pharmaceutical composition (described later) supplemented with the suppressing agent of this embodiment can treat or relieve various diseases.

2. Pharmaceutical Composition

The second embodiment of the present invention provides a pharmaceutical composition.

2-1. Constitution

The pharmaceutical composition of the present invention comprises the agent for suppressing the expression of a dominant mutant gene according to embodiment 1 as an active ingredient. The agent for suppressing the expression of a dominant mutant gene may comprise one RNAi molecule against the targeted dominant mutant gene or an expression vector comprising an operably linked DNA encoding the RNAi molecule, or may comprise one or two or more different RNAi molecules targeting the same gene, and/or expression vector(s) comprising operably linked DNA(s) encoding the one or two or more different RNAi molecules, respectively.

For example, the pharmaceutical composition of this embodiment may comprise, as active ingredients, an agent for suppressing the expression of a mutant EGFR gene, the suppressing agent comprising two or more different EGFR-RNAi molecules. In this case, the suppressing agent can comprise two or more RNAi molecules selected from the group consisting of an EGFR-RNAi molecule targeting the del (E746-A750) mutant gene (e.g., the sense strand region of the EGFR-RNAi molecule comprises the nucleotide sequence represented by SEQ ID NO: 3, 5, 7, 9, 11, 13, 15, 17, 19, or 21), an EGFR-RNAi molecule targeting the del(L747-T751)-L747S mutant gene (e.g., the sense strand region of the EGFR-RNAi molecule comprises the nucleotide sequence represented by SEQ ID NO: 29, 31, 33, 35, 37, 39, 41, 43, 45, 47, or 49), an EGFR-RNAi molecule targeting the del(L747-E749)-A750P(G) mutant gene (e.g., the sense strand region of the EGFR-RNAi molecule comprises the nucleotide sequence represented by SEQ ID NO: 53, 55, 59, 61, 63, 65, or 67), and an EGFR-RNAi molecule targeting the del(L747-E749)-A750P(A) mutant gene (e.g., the sense strand region of the EGFR-RNAi molecule comprises the nucleotide sequence represented by SEQ ID NO: 129, 131, 133, 135, 137, 139, 141, 143, or 145).

Alternatively, the agent for suppressing the expression of a mutant EGFR gene may comprise an EGFR-RNAi molecule and an EGFR-RNAi molecule expression vector (which comprises e.g., an operably linked DNA encoding the EGFR-RNAi molecule and/or a different EGFR-RNAi molecule).

The pharmaceutical composition of this embodiment may be prepared as a so-called combination formulation, which can further contain an additional pharmaceutically acceptable active ingredient without deactivating the RNAi molecule and/or the expression vector in the agent for suppressing the expression of a dominant mutant gene according to embodiment 1.

In this context, the additional active ingredient can be an expression-suppressing agent that targets the same gene as in the agent for suppressing the expression of a dominant mutant gene according to embodiment 1, but comprises an RNAi molecule and/or an expression vector comprising an operably linked DNA encoding the RNAi molecule, which constitutionally differ from the active ingredient of embodiment 1. One example of such a combination formulation targeting a mutant EGFR gene includes a combination formulation comprising: the agent for suppressing the expression of a dominant mutant gene, comprising an EGFR-RNAi molecule and/or an expression vector comprising an operably linked DNA encoding the RNAi molecule, as constituted according to embodiment 1; and, for example, an agent for suppressing the expression of a dominant allele, comprising an RNAi molecule whose sense strand region is represented by SEQ ID NO: 83 or 85, and/or an expression vector comprising an operably linked DNA encoding the RNAi molecule. In addition, the combination formulation of the present invention may further comprise an agent for suppressing the expression of a dominant mutant gene, the suppressing agent being different from the agent for suppressing the expression of a dominant allele and comprising an RNAi molecule whose sense strand region is represented by SEQ ID NO: 89 as described later in Example 4 and/or an expression vector comprising an operably linked DNA encoding the RNAi molecule as an active ingredient. Such a combination formulation comprising, as active ingredients, suppressing agents that target the different mutation sites of the same gene and suppress the gene expressions based on these mutations, respectively, is useful when the mutation site of the target gene is not identified. The RNAi molecule serving as an active ingredient in each suppressing agent has high specificity for the target mutant gene and as such, advantageously, is hardly likely to have adverse reaction such as the suppression of the expression of non-target genes and deactivate the other RNAi molecule and/or expression vectors in the mixture.

Alternatively, the additional active ingredient may be a drug having pharmacological effects different from that of the agent for suppressing the expression of a dominant mutant gene according to embodiment 1. Examples of such additional active ingredients include antibiotics.

The pharmaceutical composition of the present invention comprises the RNAi molecule and/or the expression vector as an active ingredient in a vehicle. Examples of the vehicle include solvents such as water, ethanol, propylene glycol, ethoxylated isostearyl alcohol, polyoxylated isostearyl alcohol, and polyoxyethylene sorbitan fatty acid esters. Such a vehicle is desirably sterilized. Also, such a vehicle is preferably adjusted, if necessary, to be isotonic with blood.

The content of the RNAi molecule and/or expression vector as an active ingredient in the pharmaceutical composition of the present invention differs depending on various conditions such as the type of a causative gene of a disease to be treated, the mechanism of onset thereof on which the gene acts, the functions or effects and stability of the RNAi molecule, the expression level of the expression vector, the dosage form of the pharmaceutical composition, the type of the carrier used, an administration method, and the state of a test subject receiving the pharmaceutical composition. This content may be selected appropriately on the basis of a technique known in the art. Specifically, for example, the content of the RNAi molecule or the expression vector of the present invention in an injection solution to be administered to an adult human male (body weight: 60 kg) that does not require combined use with another pharmaceutical drug can be approximately 0.01% (w/v) to approximately 20% (w/v), preferably approximately 0.1% (w/v) to approximately 10% (w/v), per dosage unit of the injection solution. Specifically, for example, 1 ml of one injection can usually contain 1 μg to 200 μg of the siRNA. When the nucleic acid of the present invention needs to be administered in large amounts for obtaining the pharmacological effect of the pharmaceutical composition of the present invention, the pharmaceutical composition may be administered at several divided doses in order to reduce burdens on the test subject.

The pharmaceutical composition of the present invention may further contain a pharmaceutically acceptable carrier, if necessary. The "pharmaceutically acceptable carrier" refers to an additive usually used in the pharmaceutical formulating art. Examples thereof include excipients, binders, disintegrants, fillers, emulsifiers, glidants or flow aids, and lubricants.

Examples of the excipients include sugars such as monosaccharides, disaccharides, cyclodextrin, and polysaccharides (more specifically including, but not limited to, glucose, sucrose, lactose, raffinose, mannitol, sorbitol, inositol, dextrin, maltodextrin, starch, and cellulose), metal salts (e.g., sodium chloride, sodium phosphate or calcium phosphate, calcium sulfate, magnesium sulfate, and calcium carbonate), citric acid, tartaric acid, glycine, low-, middle-, or high-molecular weight polyethylene glycol (PEG), Pluronic, kaolin, silicic acid, and combinations thereof.

Examples of the binders include starch glues composed of corn, wheat, rice, or potato starch, simple syrup, glucose solution, gelatin, tragacanth, methylcellulose, hydroxypropylmethylcellulose, sodium carboxymethylcellulose, shellac, polyvinylpyrrolidone.

Examples of the disintegrants include the starches described above, lactose, carboxymethyl starch, cross-linked polyvinylpyrrolidone, agar, laminaran powder, sodium bicarbonate, calcium carbonate, alginic acid or sodium alginate, polyoxyethylene sorbitan fatty acid ester, sodium lauryl sulfate, monoglyceride stearate, and salts thereof.

Examples of the fillers include the sugars described above, calcium phosphate (e.g., tricalcium phosphate or calcium hydrogen phosphate), and combinations thereof.

Examples of the emulsifiers include sorbitan fatty acid ester, glycerin fatty acid ester, sucrose fatty acid ester, and propylene glycol fatty acid ester.

Examples of the glidants or flow aids and the lubricants include silicate, talc, stearate, and polyethylene glycol.

These carriers are used mainly for facilitating the formulation of the dosage form and maintaining the dosage form and the drug effects as well as for preventing the in vivo nuclease-catalyzed degradation of the RNAi molecule serving as an active ingredient in the agent for suppressing the expression of a dominant mutant gene, and may be used appropriately according to the need. The pharmaceutical composition may also comprise, in addition to the additives described above, optional additives such as corrigents, solubilizers, suspending agents, diluents, surfactants, stabilizers, absorption promoters, expanders, wetting agents, humectants, adsorbents, disintegration inhibitors, coating agents, coloring agents, preservatives, antioxidants, fragrances, flavors, sweeteners, and buffers.

The pharmaceutical composition of the present invention can also contain another drug without losing the pharmacological effect of the RNAi molecule. For example, an injection may contain a predetermined amount of an antibiotic.

The dosage form of the pharmaceutical composition of this embodiment is not particularly limited as long as the form does not deactivate the RNAi molecule or the expression vector as an active ingredient in the suppressing agent or the additional active ingredient. Since RNA is generally unstable, the dosage form for administration of the RNAi molecule is preferably a dosage form insusceptible to in vivo degradation. For example, any of liquid, solid, and semisolid forms may be used. Specific examples of the dosage form include: parenteral dosage forms such as injections, suspensions, emulsions, eye drops, nasal drops, creams, ointments, plasters, patches, and suppositories; and oral dosage forms such as solutions, powders, granules, tablets, capsules, sublingual formulations, and troches. The dosage form of the pharmaceutical composition of this embodiment comprising the suppressing agent comprising the RNAi molecule or the expression vector as an active ingredient is preferably an injection.

The pharmaceutical composition of this embodiment or the agent for suppressing the expression of a dominant mutant gene according to embodiment 1 may be prepared in the form of nanoparticles (including e.g., a targeted nanoparticle delivery system described in Davis M E, et al., Nature, 2010, 464: 1067-1070), a liposome (including e.g., membrane-permeable peptide-binding liposomes and SNALPs), or a cholesterol conjugate. An RNAi delivery system described in Castanotto D. & Rossi J J., Nature, 2009, 457, 426-433 may be used.

2-2. Administration Method

The pharmaceutical composition of this embodiment can be administered to an organism in a pharmaceutically effective amount for the treatment of the disease of interest. The recipient organism is a vertebrate, preferably a mammal, more preferably a human.

In the present specification, the "pharmaceutically effective amount" refers to a dose required, for the RNAi molecule and/or the expression vector as an active ingredient in the suppressing agent contained in the pharmaceutical composition of the present invention, to treat the disease of interest or relieve its symptoms (specifically, a dose at which the active ingredient can suppress the trait exhibition of the dominant mutant gene causative of the disease) with no or little adverse reaction (e.g., suppression of the expression of the wild-type gene, etc.) harmful to the recipient organism. The specific amount differs depending on the type of the targeted gene, the trait-exhibiting effect of the dominant mutant gene, the dosage form used, information about a test subject (or a human subject), and an administration route. The range of the pharmaceutically effective amount and a preferable administration route for administration to a human are generally set on the basis of data obtained from cell culture assay and animal experiments. The dose is finally determined and adjusted at a physician's discretion according to an individual human subject. In this case, information about the human subject to be considered includes, for example, the degree of progression or severity of the disease, general health conditions, age, body weight, sex, diet, drug sensitivity, and resistance to treatment.

The RNAi molecule of the present invention may be administered systemically or locally. An appropriate route can be selected according to, for example, the type, site of onset, degree of progression of the disease. For a disease whose onset is localized at a site, local administration is preferable, in which the RNAi molecule of the present invention is directly administered to the site of onset and its neighborhood through injection or the like. This is because the RNAi molecule of the present invention can be delivered in sufficient amounts to the site (tissue or organ) to be treated with little influence on the other tissues. For a disease, such as metastatic cancer, whose site to be treated cannot be identified or a disease whose onset is systemic, systemic administration through intravenous injection or the like is preferable, though the administration route is not limited thereto. This is because the RNAi molecule of the present invention can be distributed throughout the body via blood flow and thereby delivered even to a lesion that cannot be found by diagnosis.

The RNAi molecule of the present invention can be administered by any appropriate method without deactivating the active ingredient contained. For example, any of parenteral (e.g., injection, aerosol, application, eye drop, and nasal drop) and oral administrations can be performed. Injection is preferable.

In the case of administration through injection, an injection site is not particularly limited. The injection site may be any site at which the RNAi molecule of the present invention or the RNAi molecule produced from the expression vector of the present invention can exert its functions on the target molecule and achieve the purpose of the pharmaceutical composition. Examples thereof include intravenous, intraarterial, intrahepatic, intramuscular, intraarticular, intramedullary, intraspinal, intraventricular, transdermal, hypodermic, intradermal, intraperitoneal, intranasal, enteral, and sublingual injections. Intravascular injection such as intravenous injection or intraarterial injection is preferable. This is because, as described above, the pharmaceutical composition of the present invention can be distributed throughout the body via blood flow and also because this injection is relatively low invasive. The RNAi molecule may be administered systemically through intravascular injection using, for example, the targeted nanoparticle delivery system of Davis et al. described above.

2-3. Use

The pharmaceutical composition of the present invention can be used for the treatment of a disease. The pharmaceutical composition of the present invention can be applied to a disease caused by the expression of a dominant mutant gene, for example, an autosomal dominantly inherited disease, thereby selectively suppressing the expression of the mutant gene while allowing traits to be manifested from genes having normal functions or the wild-type gene encoding a protein. Thus, the pharmaceutical composition of the present invention can be used in the treatment of inherited diseases, cancers, and the like, which have previously been difficult to treat, and can also be used in the breeding of animal or plant species, etc. In this regard, the disease targeted by the pharmaceutical composition of this embodiment is a disease based on a dominant trait brought about by the dominant mutant gene targeted by the RNAi molecule contained in the suppressing agent or the RNAi molecule expressed from the expression vector contained therein. Specific examples of such diseases include a disease caused by a postnatally occurring mutation in genomic DNA within a particular cell, and a disease caused by an autosomal dominant mutation. Specific examples of these diseases are as described above. Thus, the pharmaceutical composition of this embodiment can be applied to various diseases by using an RNAi molecule against a dominant mutant gene causative of a disease to be treated or an expression vector comprising a DNA encoding it as an active ingredient.

EXAMPLES

Example 1

Test on ASP-RNAi Effect of siRNA on EGFR Gene

An siRNA specifically suppressing the expression of a mutant epidermal growth factor receptor (EGFR) gene (this siRNA is also referred to as EGFR-siRNA) was designed and tested for its expression suppressive effect on the mutant gene (cancer-causative gene), i.e., its allele-specific gene silencing (or allele-specific RNAi ASP-RNAi) effect.

Gain of function mutant EGFR genes are causative genes of non-small cell lung cancer (NSCLC). Hence, the EGFR-siRNA of the present invention can be used as an effective therapeutic agent for non-small cell lung cancer, if it has an ASP-RNAi effect that specifically suppresses only the expression of such gain of function mutant EGFR genes.

(1) Type of Mutant EGFR Gene

Figure 8:
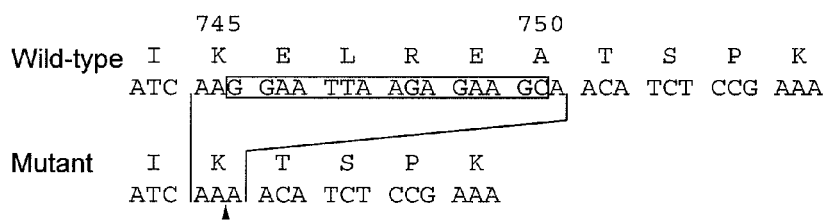
FIG. 8A is a diagram showing the comparison of a deletion site and its neighboring nucleotide sequences (and an amino acid sequence encoded thereby) between the wild-type EGFR gene (SEQ ID NO: 150 nucleotide sequence; SEQ ID NO: 149 amino acid sequence) and a deletion mutant EGFR gene del(E764-A750) (SEQ ID NO: 152 nucleotide sequence; SEQ ID NO: 151 amino acid sequence). The boxed region in the nucleotide sequence of the wild-type EGFR gene (SEQ ID NO: 150) corresponds to the deleted region in the mutant EGFR gene. A position corresponding to a point of discontinuity on a transcript of this mutant gene is indicated by arrowhead.
FIG. 8B shows the expression suppressive effects of EGFR-siRNA on the non-target wild-type EGFR gene and the deletion mutant EGFR gene del(E764-A750), wherein these effects were calculated as their respective relative values with the luciferase activity of siControl as 1.0. The luciferase activity was corrected with the expression level of β-galactosidase as an external control insusceptible to the RNAi-mediated suppression of expression.
FIG. 8C shows the ASP scores of EGFR-siRNA against the non-target wild-type EGFR gene and the deletion mutant EGFR gene del(E764-A750). The threshold (ASP score of 0.4) is indicated by broken line.
Figure 1:
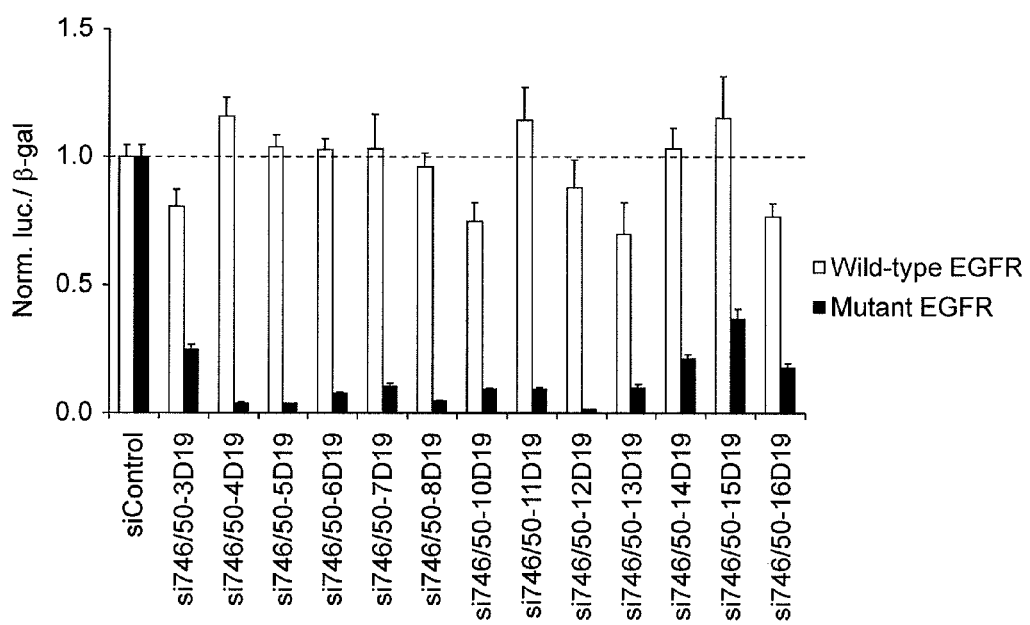
Figures 2, 8:
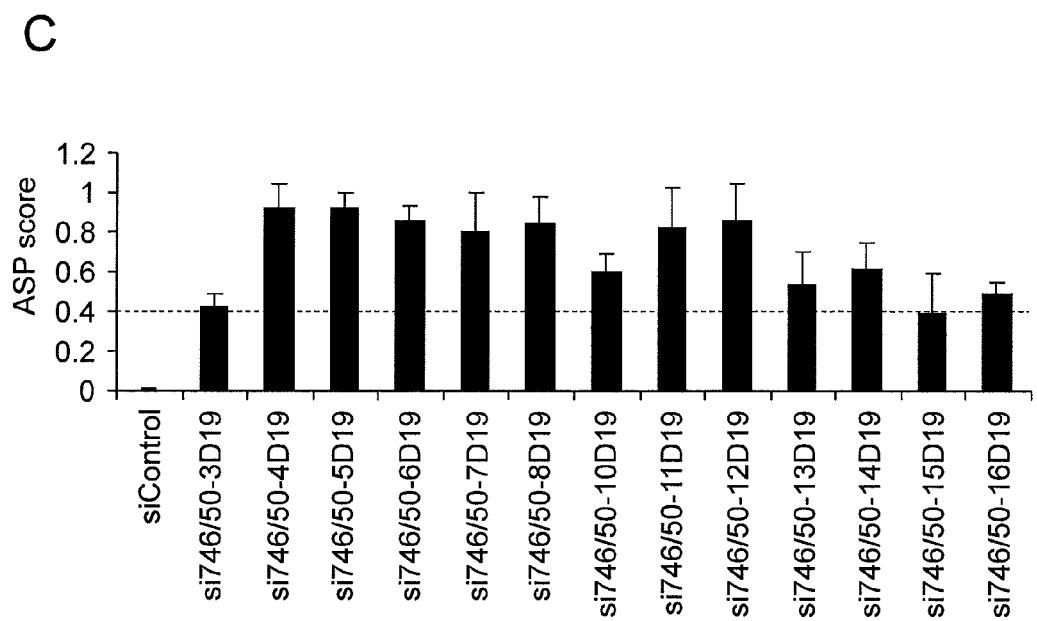
Figure 9:
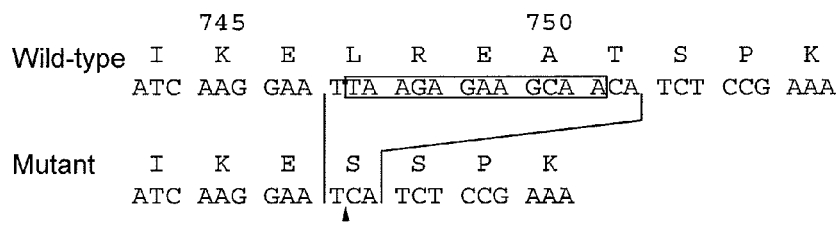
FIG. 9A is a diagram showing the comparison of a deletion site and its neighboring nucleotide sequences (and an amino acid sequence encoded thereby) between the wild-type EGFR gene (SEQ ID NO: 150 nucleotide sequence; SEQ ID NO.
FIG. 9B shows the expression suppressive effects of EGFR-siRNA on the non-target wild-type EGFR gene and the deletion mutant EGFR gene del(L747-T751)-L747S, wherein these effects were calculated as their respective relative values with the luciferase activity of siControl as 1.0. The luciferase activity of each sample was corrected with the expression level of β-galactosidase as an external control insusceptible to the RNAi-mediated suppression of expression.
FIG. 9C shows the ASP scores of EGFR-siRNA against the non-target wild-type EGFR gene and the deletion mutant EGFR gene del(L747-T751)-L747S. The threshold (ASP score of 0.4) is indicated by broken line.
Figure 1:
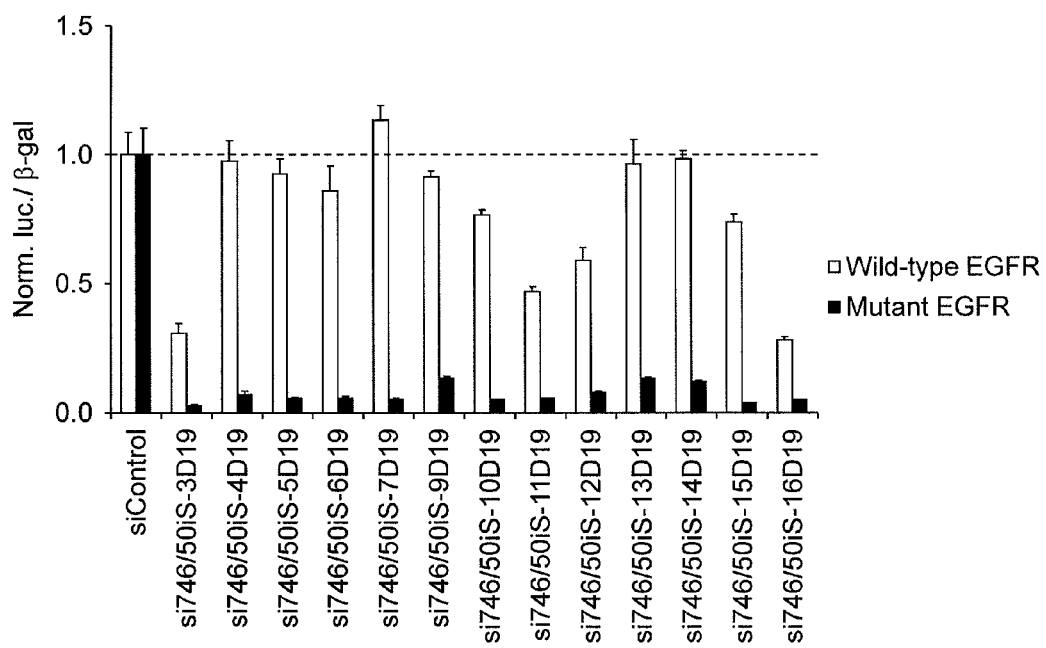
Figures 2, 9:
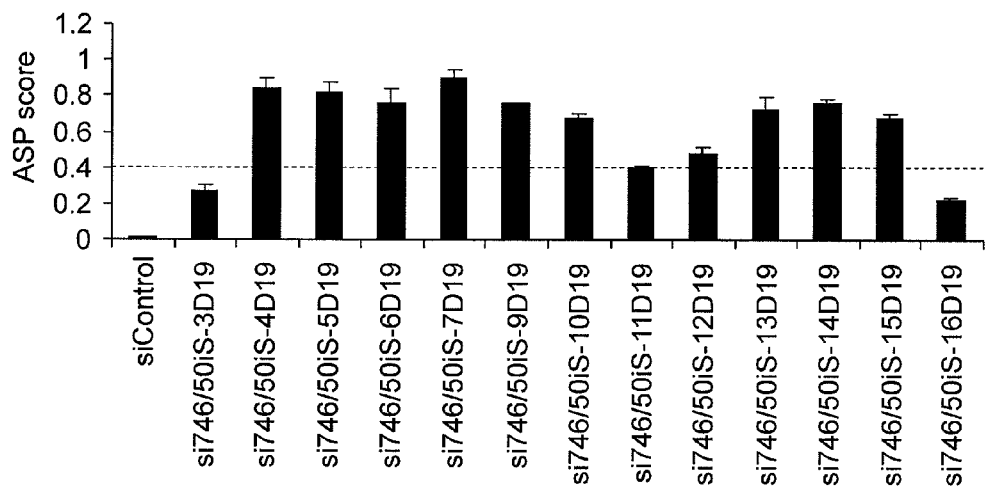
Figure 10:
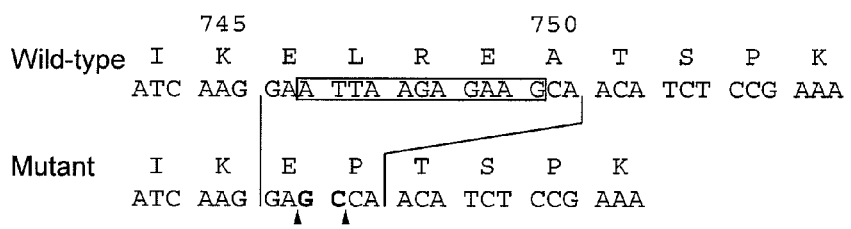
FIG. 10A is a diagram showing the comparison of a deletion site and its neighboring nucleotide sequences (and an amino acid sequence encoded thereby) between the wild-type EGFR gene (SEQ ID NO: 150 nucleotide sequence; SEQ ID NO: 149 amino acid sequence) and a deletion/insertion mutant EGFR gene del(L747-E749)-A750P(G) (SEQ ID NO: 156 nucleotide sequence; SEQ ID NO: 155 amino acid sequence). The boxed region in the nucleotide sequence of the wild-type EGFR gene (SEQ ID NO: 150) corresponds to the deleted region in the mutant EGFR gene. The base in bold type in the mutant EGFR gene (SEQ ID NO: 156) corresponds to the inserted base. A position corresponding to each point of discontinuity on a transcript of this mutant gene is indicated by arrowhead. This deletion/insertion mutant has two points of discontinuity.
FIG. 10B shows the expression suppressive effects of EGFR-siRNA on the non-target wild-type EGFR gene and the deletion/insertion mutant EGFR gene del(L747-E749)-A750P(G), wherein these effects were calculated as their respective relative values with the luciferase activity of siControl as 1.0. The luciferase activity of each sample was corrected with the expression level of β-galactosidase as an external control insusceptible to the RNAi-mediated suppression of expression.
FIG. 10C shows the ASP scores of EGFR-siRNA against the non-target wild-type EGFR gene and the deletion/insertion mutant EGFR gene del(L747-E749)-A750P(G). The threshold (ASP score of 0.4) is indicated by broken line.
Figure 1:
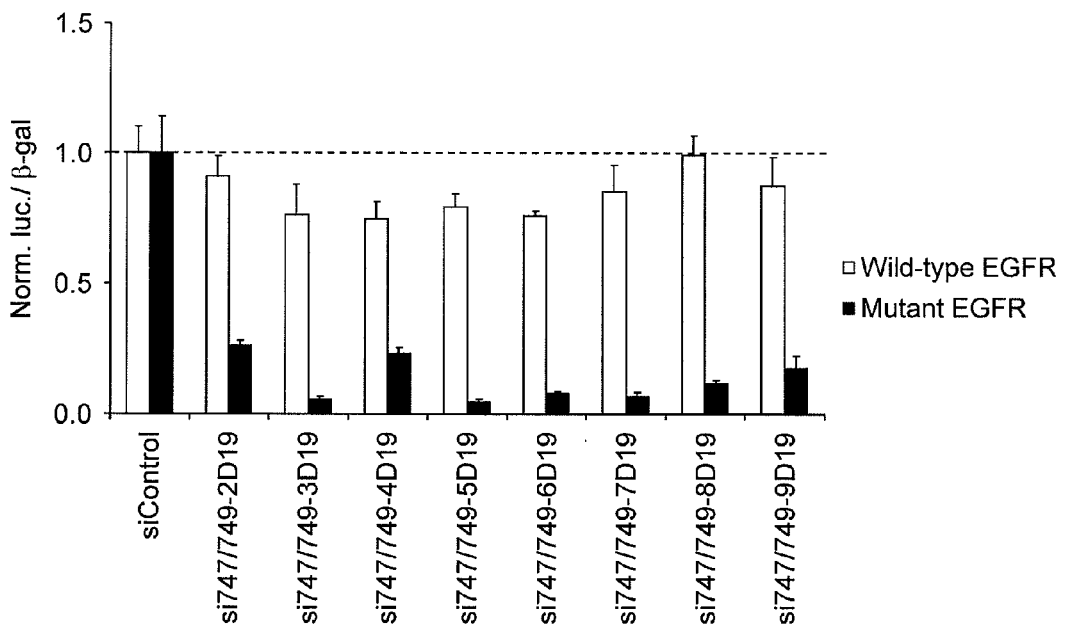
Figures 2, 10:
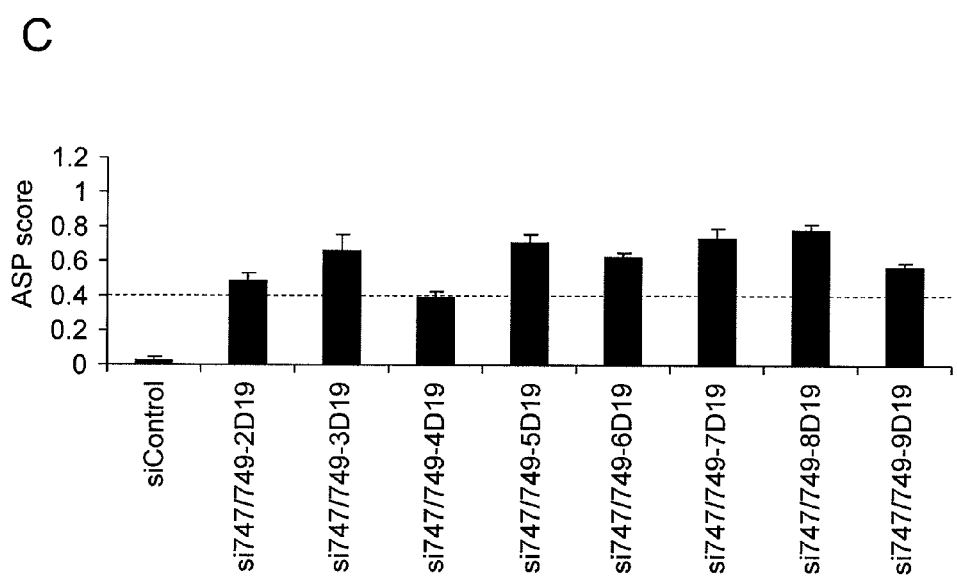
Figure 11:
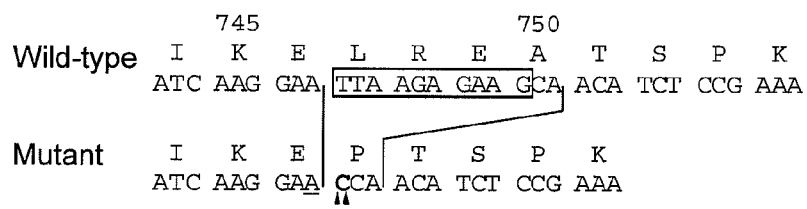
FIG. 11A is a diagram showing the comparison of a deletion site and its neighboring nucleotide sequences (and an amino acid sequence encoded thereby) between the wild-type EGFR gene (SEQ ID NO: 150 nucleotide sequence; SEQ ID NO: 149 amino acid sequence) and a deletion/insertion mutant EGFR gene del(L747-E749)-A750P(A) (SEQ ID NO: 158 nucleotide sequence; SEQ ID NO: 157 amino acid sequence). The boxed region in the nucleotide sequence of the wild-type EGFR gene (SEQ ID NO: 150) corresponds to the deleted region in the mutant EGFR gene. The base in bold type in the mutant EGFR gene (SEQ ID NO: 158) corresponds to the inserted base. A position corresponding to each point of discontinuity on a transcript of this mutant gene is indicated by arrowhead. This deletion/insertion mutant has two points of discontinuity.
FIG. 11B shows the expression suppressive effects of EGFR-siRNA on the non-target wild-type EGFR gene and the deletion/insertion mutant EGFR gene del(L747-E749)-A750P(A), wherein these effects were calculated as their respective relative values with the luciferase activity of siControl as 1.0. The luciferase activity of each sample was corrected with the expression level of β-galactosidase as an external control insusceptible to the RNAi-mediated suppression of expression.
FIG. 11C shows the ASP scores of EGFR-siRNA against the non-target wild-type EGFR gene and the deletion/insertion mutant EGFR gene del(L747-E749)-A750P(A). The threshold (ASP score of 0.4) is indicated by broken line.
Figure 1:
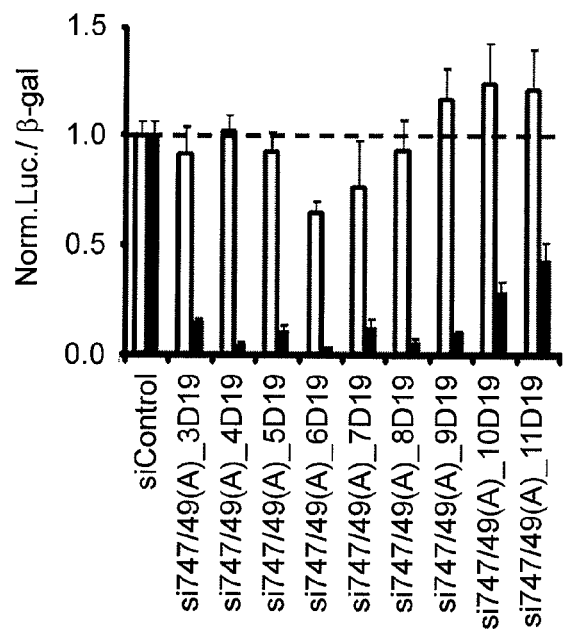
Figures 2, 11:
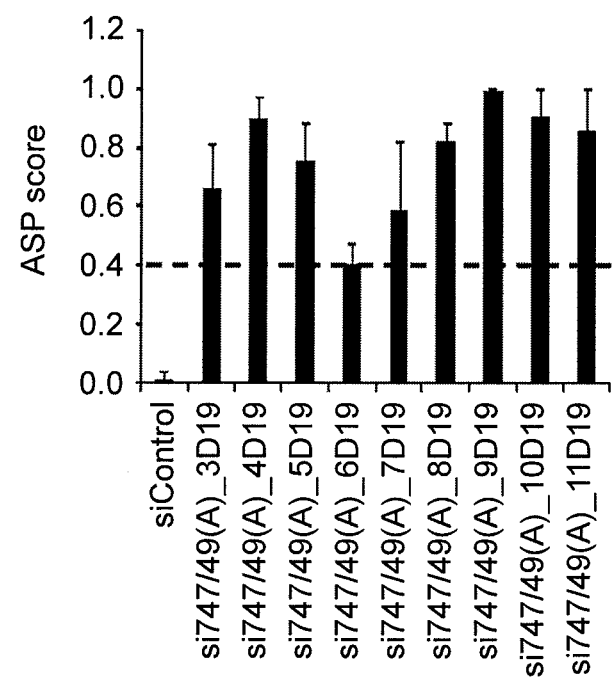

Non-small cell lung cancer patients have been found to have various disease-related mutations (gain of function mutations) in the EGFR gene (Accession No. NM_005228). Examples of these mutations include: as shown in FIG. 8-1 A, "del(E746-A750) mutation" that deletes the nucleotide sequence from positions 2235 to 2249 (counted from A in the start codon as the first position; the same holds true for the description below) (the gene deletion mutation results in a mutant protein in which glutamic acid 746 to alanine 750 (counted from initiating methionine as the first position) are deleted); as shown in FIG. 9-1 A, "del(L747-T751)-L747S mutation" that deletes the nucleotide sequence from positions 2240 to 2251 (the gene deletion mutation results in a mutant protein in which leucine 747 to threonine 751 are deleted and leucine 747 is substituted by serine); as shown in FIG. 10-1 A, "del(L747-E749)-A750P(G) mutation" that deletes the nucleotide sequence from positions 2238 to 2248 and newly inserts 2 bases to the deletion site (the gene deletion/insertion mutation results in a mutant protein in which leucine 747 to glutamic acid 749 are deleted and alanine 750 is substituted by proline); and as shown in FIG. 11-1 A, "del(L747-E749)-A750P(A) mutation" by which a base corresponding to position 2238 (counted from A in the start codon), i.e., the third base in a codon (GAG) encoding E746 is not "G" (Pao et al., 2005, PloS Medicine, Vol. 2, Issue 3: e73) but is "A" (Paez et al., 2004, Science, vol. 304, 1497-1500). Alternative examples thereof also include point mutations.

Thus, each EGFR-siRNA was designed in accordance with the method for designing the RNAi molecule according to embodiment 1, and the prepared EGFR-siRNAs were tested for the presence or absence of their abilities to specifically suppress the expression of these mutant genes.

(2) Design and Preparation of EGFR-siRNA

Positions corresponding to those indicated by arrowheads in FIGS. 8-1 A, 9-1 A, 10-1 A, and 11-1 A, respectively, on mutant gene products (mutation mRNAs) derived from the del(E746-A750) mutation, del(L747-T751)-L747S mutation, and del(L747-E749)-A750P mutation described above correspond to the point of discontinuity described in the present specification. Specifically, transcripts of the del (E746-A750) mutant gene and the del(L747-T751)-L747S mutant gene each have one point of discontinuity, while a transcript of the del(L747-E749)-A750P mutant gene has two points of discontinuity. Thus, bases 5' and 3' flanking this point of discontinuity were selected as first and second reference bases, respectively (reference base selection step). The del(L747-E749)-A750P mutant gene transcript has two points of discontinuity, which are located in the proximity to flank only 1 base (in the case of L747-E749)-A750P(A)) or 2 bases (in the case of L747-E749)-A750P(G)). Hence, here, bases 5' and 3' flanking the downstream (3') point of discontinuity were selected as first and second reference bases, respectively, as a matter of form. Next, the 3'-terminal base of each RNAi sense strand region was selected so as to differ one by one in the number of bases from the base corresponding to the second reference base to the 3' end (3'-terminal base selection step). Subsequently, a nucleotide sequence comprising 19 consecutive bases including the first and second reference bases on the transcript from each mutant gene was selected as an RNAi sense strand region (RNAi sense strand region selection step). Also, a nucleotide sequence comprising a nucleotide sequence complementary to the selected nucleotide sequence of the RNAi sense strand region was selected as an RNAi antisense strand region (RNAi antisense strand region selection step).

The specific nucleotide sequences of the EGFR-siRNAs designed and used in this Example are shown in Tables 1 to 4.

TABLE 1

| siRNA name | ss/as | Nucleotide sequence (5' → 3') | SEQ ID NO |
|---|---|---|---|
| si746/50-3D19 | ss | UUCCCGUCGCUAUCAA^AAC | 1 |
| | as | GUU^UUGAUAGCGACGGGAA | 2 |
| si746/50-4D19 | ss | UCCCGUCGCUAUCAA^AACA | 3 |
| | as | UGUU^UUGAUAGCGACGGGA | 4 |
| si746/50-5D19 | ss | CCCGUCGCUAUCAA^AACAU | 5 |
| | as | AUGUU^UUGAUAGCGACGGG | 6 |
| si746/50-6D19 | ss | CCGUCGCUAUCAA^AACAUC | 7 |
| | as | GAUGUU^UUGAUAGCGACGG | 8 |
| si746/50-7D19 | ss | CGUCGCUAUCAA^AACAUCU | 9 |
| | as | AGAUGUU^UUGAUAGCGACG | 10 |
| si746/50-8D19 | ss | GUCGCUAUCAA^AACAUCUC | 11 |
| | as | GAGAUGUU^UUGAUAGCGAC | 12 |
| si746/50-10D19 | ss | CGCUAUCAA^AACAUCUCCG | 13 |
| | as | CGGAGAUGUU^UUGAUAGCG | 14 |
| si746/50-11D19 | ss | GCUAUCAA^AACAUCUCCGA | 15 |
| | as | UCGGAGAUGUU^UUGAUAGC | 16 |
| si746/50-12D19 | ss | CUAUCAA^AACAUCUCCGAA | 17 |
| | as | UUCGGAGAUGUU^UUGAUAG | 18 |
| si746/50-13D19 | ss | UAUCAA^AACAUCUCCGAAA | 19 |
| | as | UUUCGGAGAUGUU^UUGAUA | 20 |
| si746/50-14D19 | ss | AUCAA^AACAUCUCCGAAAG | 21 |
| | as | CUUUCGGAGAUGUU^UUGAU | 22 |
| si746/50-15D19 | ss | UCAA^AACAUCUCCGAAAGC | 23 |
| | as | GCUUUCGGAGAUGUU^UUGA | 24 |
| si746/50-16D19 | ss | CAA^AACAUCUCCGAAAGCC | 25 |
| | as | GGCUUUCGGAGAUGUU^UUG | 26 |

TABLE 2

| siRNA name | ss/as | Nucleotide sequence (5' → 3') | SEQ ID NO |
|---|---|---|---|
| si747/51-3D19 | ss | GUCGCUAUCAAGGAAU^CAU | 27 |
| | as | AUG^AUUCCUUGAUAGCGAC | 28 |
| si747/51-4D19 | ss | UCGCUAUCAAGGAAU^CAUC | 29 |
| | as | GAUG^AUUCCUUGAUAGCGA | 30 |
| si747/51-5D19 | ss | CGCUAUCAAGGAAU^CAUCU | 31 |
| | as | AGAUG^AUUCCUUGAUAGCG | 32 |
| si747/51-6D19 | ss | GCUAUCAAGGAAU^CAUCUC | 33 |
| | as | GAGAUG^AUUCCUUGAUAGC | 34 |
| si747/51-7D19 | ss | CUAUCAAGGAAU^CAUCUCC | 35 |
| | as | GGAGAUG^AUUCCUUGAUAG | 36 |
| si747/51-9D19 | ss | AUCAAGGAAU^CAUCUCCGA | 37 |
| | as | UCGGAGAUG^AUUCCUUGAU | 38 |
| si747/51-10D19 | ss | UCAAGGAAU^CAUCUCCGAA | 39 |
| | as | UUCGGAGAUG^AUUCCUUGA | 40 |
| si747/51-11D19 | ss | CAAGGAAU^CAUCUCCGAAA | 41 |
| | as | UUUCGGAGAUG^AUUCCUUG | 42 |
| si747/51-12D19 | ss | AAGGAAU^CAUCUCCGAAAG | 43 |
| | as | CUUUCGGAGAUG^AUUCCUU | 44 |
| si747/51-13D19 | ss | AGGAAU^CAUCUCCGAAAGC | 45 |
| | as | GCUUUCGGAGAUG^AUUCCU | 46 |
| si747/51-14D19 | ss | GGAAU^CAUCUCCGAAAGCC | 47 |
| | as | GGCUUUCGGAGAUG^AUUCC | 48 |
| si747/51-15D19 | ss | GAAU^CAUCUCCGAAAGCCA | 49 |
| | as | UGGCUUUCGGAGAUG^AUUC | 50 |
| si747/51-16D19 | ss | AAU^CAUCUCCGAAAGCCAA | 51 |
| | as | UUGGCUUUCGGAGAUG^AUU | 52 |

TABLE 3

| siRNA name | ss/as | Nucleotide sequence (5' → 3') | SEQ ID NO |
|---|---|---|---|
| si747/49-2D19 | ss | CGUCGCUAUCAAGGA^GC^CA | 53 |
| | as | UG^GC^UCCUUGAUAGCGACG | 54 |
| si747/49-3D19 | ss | GUCGCUAUCAAGGA^GC^CAA | 55 |
| | as | UUG^GC^UCCUUGAUAGCGAC | 56 |
| si747/49-4D19 | ss | UCGCUAUCAAGGA^GC^CAAC | 57 |
| | as | GUUG^GC^UCCUUGAUAGCGA | 58 |
| si747/49-5D19 | ss | CGCUAUCAAGGA^GC^CAACA | 59 |
| | as | UGUUG^GC^UCCUUGAUAGCG | 60 |
| si747/49-6D19 | ss | GCUAUCAAGGA^GC^CAACAU | 61 |
| | as | AUGUUG^GC^UCCUUGAUAGC | 62 |
| si747/49-7D19 | ss | CUAUCAAGGA^GC^CAACAUC | 63 |
| | as | GAUGUUG^GC^UCCUUGAUAG | 64 |
| si747/49-8D19 | ss | UAUCAAGGA^GC^CAACAUCU | 65 |
| | as | AGAUGUUG^GC^UCCUUGAUA | 66 |
| si747/49-9D19 | ss | AUCAAGGA^GC^CAACAUCUC | 67 |
| | as | GAGAUGUUG^GC^UCCUUGAU | 68 |

TABLE 4

| siRNA name | ss/as | Nucleotide sequence (5' → 3') | SEQ ID NO |
|---|---|---|---|
| si747/49(A)_3D19 | ss | CGUCGCUAUCAAGGAA^C^CA | 129 |
|  | as | UG^C^UUCCUUGAUAGCGACG | 130 |
| si747/49(A)_4D19 | ss | GUCGCUAUCAAGGAA^C^CAA | 131 |
|  | as | UUG^C^UUCCUUGAUAGCGAC | 132 |
| si747/49(A)_5D19 | ss | UCGCUAUCAAGGAA^C^CAAC | 133 |
|  | as | GUUG^C^UUCCUUGAUAGCGA | 134 |
| si747/49(A)_6D19 | ss | CGCUAUCAAGGAA^C^CAACA | 135 |
|  | as | UGUUG^C^UUCCUUGAUAGCG | 136 |
| si747/49(A)_7D19 | ss | GCUAUCAAGGAA^C^CAACAU | 137 |
|  | as | AUGUUG^C^UUCCUUGAUAGC | 138 |
| si747/49(A)_8D19 | ss | CUAUCAAGGAA^C^CAACAUC | 139 |
|  | as | GAUGUUG^C^UUCCUUGAUAG | 140 |
| si747/49(A)_9D19 | ss | UAUCAAGGAA^C^CAACAUCU | 141 |
|  | as | AGAUGUUG^C^UUCCUUGAUA | 142 |
| si747/49(A)_10D19 | ss | AUCAAGGAA^C^CAACAUCUC | 143 |
|  | as | GAGAUGUUG^C^UUCCUUGAU | 144 |
| si747/49(A)_11D19 | ss | UCAAGGAA^C^CAACAUCUCC | 145 |
|  | as | GGAGAUGUUG^C^UUCCUUGA | 146 |

Table 1 shows the nucleotide sequences of the sense strand region (ss) and antisense strand region (as) of each siRNA designed against the del(E746-A750) mutant gene. Table 2 shows the nucleotide sequences of the sense strand region (ss) and antisense strand region (as) of each siRNA designed against the del(L747-T751)-L747S mutant gene. Table 3 shows the nucleotide sequences of the sense strand region (ss) and antisense strand region (as) of each siRNA designed against the del(L747-E749)-A750P(G) mutant gene. Table 4 shows the nucleotide sequences of the sense strand region (ss) and antisense strand region (as) of each siRNA designed against the del(L747-E749)-A750P(A) mutant gene. The nucleotide sequences shown in each table are described except for 3'-terminal additional bases consisting of UU at each of the 3' ends of the sense strand region and the antisense strand region, for the sake of convenience. Also, SEQ ID NOs in each table correspond to numbers in Sequence Listing.

As for the EGFR-siRNA names in each table, for example, "si746/50-3D19" in Table 1 represents an siRNA against the del(E746-A750) mutation, comprising an RNAi sense strand region consisting of 19 bases, with the number of bases from the second reference base to the 3' end set to 3. Specifically, "si" of "si746/50" in "si746/50-3D19" represents an siRNA; "746/50" of "si746/50" represents 746 to 750 in the del (E746-A750) mutation; "D" of "3D19" represents a deletion mutation; "3" of "3D19" represents that the number of bases from the second reference base to the 3' end is 3; and "19" of "3D19" represents that the RNAi sense strand region consists of 19 bases. The names of the siRNAs against the del(L747-E749)-A750P(A) mutant gene shown in Table 4 were distinguished from the siRNAs against the del(L747-E749)-A750P (G) mutant gene shown in Table 3 by adding "(A)" to "si747/49-3D19" (i.e., indicated by "si747/49(A)-3D19") in the definitions described above. Also, "A" in each sense strand region (ss) in each table represents a point of discontinuity, and "A" in each antisense strand region (as) represents a position corresponding to the point of discontinuity in the sense strand region. The underlined base in the sense strand region (ss) in each table represents the second reference base. The inserted bases (2 bases) in the del(L747-E749)-A750P (G) mutation are indicated in bold type.

The synthesis of each siRNA was outsourced to Sigma-Aldrich Corp. The synthesized siRNAs each had a sense strand region and an antisense strand region annealed to each other, and were used directly in experiments.

(3) Construction of Reporter Gene Expression Plasmid

In order to evaluate and screen the EGFR-siRNAs prepared in the paragraph (1) for their RNAi effects, reporter gene expression plasmids for the dominant mutant genes targeted by the siRNAs and the non-target wild-type gene were constructed using plasmids pGL3-TK (Ohnishi Y., et al., 2006, Journal of RNAi and Gene Silencing, Vol. 2: 154-160) expressing the *Photinus* luciferase gene and phRL-TK (Promega Corp.) expressing the *Renilla* luciferase gene.

The methods for designing a synthetic oligo-DNA containing each mutation site, inserting the DNA into a reporter gene expression plasmid, and screening for suitable siRNAs followed Ohnishi Y., et al., 2008, PloS One, Vol. 3, Issue 5: e2248. Specifically, sense and antisense strand regions were each synthesized for each oligo-DNA containing the gene deletion or deletion/insertion mutation site of del(E746-A750), del(L747-T751)-L747S, or del(L747-E749)-A750P in the EGFR gene responsible for non-small cell lung cancer (this synthesis was outsourced to Sigma-Aldrich Corp.). For this DNA synthesis, uracil (U) in each sense strand region and antisense strand region shown in Tables 1 to 4 was converted to thymine (T). An oligo-DNA of the wild-type gene having no mutation was similarly synthesized. Their respective specific nucleotide sequences are shown in Tables 5 and 6. These sense and antisense strand regions contained linker sequences constituting restriction enzyme cleavage sites, at both ends of the sense and antisense strand regions of the EGFR gene fragments. In the tables, the linker sequences are underlined, and the point of discontinuity for each EGFR gene is indicated by "^". In each table, the second reference base in each sense strand region (ss) is highlighted. The inserted bases (2 bases) in the del(L747-E749)-A750P(G) mutant gene and the inserted base (1 base) in the del(L747-E749)-A750P(A) mutant gene are indicated in bold type in Tables 5 and 6, respectively. EGFR(T790T) and EGFR(T790M) represent synthetic oligo-DNAs for point mutation in EGFR, wherein bases indicated by lower-case character represent point mutation sites.

TABLE 5

| Sequence name | ss/as | Nucleotide sequence (5' → 3') | SEQ ID NO |
|---|---|---|---|
| EGFR (T790T) | ss | CTAGCATGCGTGCAGCTCATCAcGCAGCTCATGCA | 69 |
|  | as | GGCCTGCATGAGCTGCgTGATGAGCTGCACGCATG | 70 |
| EGFR (T790M) | ss | CTAGCATGCGTGCAGCTCATCAtGCAGCTCATGCA | 71 |
|  | as | GGCCTGCATGAGCTGCaTGATGAGCTGCACGCATG | 72 |

TABLE 5-continued

| Sequence name | ss/as | Nucleotide sequence (5' → 3') | SEQ ID NO |
|---|---|---|---|
| EGFR (WT) | ss | CTAGCATGCATTCCCGTCGCTATCAAGGAATTAAGAGAAGCAACATCTCCGAAAGCCAACAAGGAAA | 73 |
|  | as | GGCCTTTCCTTGTTGGCTTTCGGAGATGTTGCTTCTCTTAATTCCTTGATAGCGACGGGAATGCATG | 74 |
| EGFR [del(E746-A750)] | ss | CTAGCATGCATTCCCGTCGCTATCAA^ACATCTCCGAAAGCCAACAAGGAAA | 75 |
|  | as | GGCCTTTCCTTGTTGGCTTTCGGAGATGTT^TTGATAGCGACGGGAATGCATG | 76 |
| EGFR [del(L747-T751)-L747S] | ss | CTAGCATGCATTCCCGTCGCTATCAAGGAAT^ATCTCCGAAAGCCAACAAGGAAA | 77 |
|  | as | GGCCTTTCCTTGTTGGCTTTCGGAGATG^ATTCCTTGATAGCGACGGGAATGCATG | 78 |
| EGFR [del(L747-E749)-A750P] | ss | CTAGCATGCGTCGCTATCAAGGA^GC^AACATCTCCGA | 79 |
|  | as | GGCCTCGGAGATGTTG^GC^TCCTTGATAGCGACGCATG | 80 |

| Sequence name | ss/as | Nucleotide sequence (5' → 3') | SEQ ID NO |
|---|---|---|---|
| EGFR [del (L747-E749)_A750P(A)] | ss | CTAGCATGCGTCGCTATCAAG GAA^C^CAACATCTCCGA | 147 |
|  | as | GGCCTCGGAGATGTTG^G^TTCCTTGATAGCGACGCATG | 148 |

Next, the synthesized oligo-DNAs of the sense and antisense strands were annealed. Specifically, the single-stranded oligo-DNAs of the sense and antisense strand regions (final concentration: 1 μM each), 10× annealing buffer (Invitrogen Corp.; final concentration: 1×), and sterilized water were mixed into a final volume of 10 μL, heat-treated at 80° C. for 5 minutes, and then left at room temperature for 30 minutes to form a duplex.

Subsequently, the oligo-DNA duplex was inserted to two plasmids (described above) treated with restriction enzymes. Specifically, the pGL3-TK and phRL-TK plasmids were treated with restriction enzymes XbaI and NotI. Then, the normal gene was inserted to the 3' untranslated region (3' UTR) of the reporter gene in the pGL3-TK plasmid, while the dominant mutant gene was inserted to this region in the phRL-TK plasmid to construct the wild type EGFR and dominant mutant EGFR reporter gene expression plasmids. Also, reporter gene expression plasmids were constructed in the same way as above except that the reporter genes were interchanged between the normal and dominant mutant genes.

(4) Cell Culture

Human-derived cell line HeLa cells were cultured at 37° C. under 5% $CO_2$ using a DMEM culture solution (Wako Pure Chemical Industries, Ltd.) containing 10% fetal bovine serum (FBS; Invitrogen Corp.) and antibiotics (100 units/mL penicillin and 100 μg/mL streptomycin; Wako Pure Chemical Industries, Ltd.).

(5) Transfection and Reporter Assay

Various EGFR-siRNAs were studied for their RNAi effects and the general structural rule of RNAi molecules suitable for RNAi induction by reporter assay using the reporter gene expression plasmids.

On the day before gene introduction, the HeLa cells were dispersed by trypsin digestion. The cell dispersion was then adjusted to a cell density of $1 \times 10^5$ cells/cm$^2$ and inoculated to a 96-well culture plate. The HeLa cells were cultured in an antibiotic-free DMEM culture solution. 24 hours later, 3 types of plasmids were introduced into the HeLa cells: (a) a pGL3-TK backbone plasmid (60 ng/well), which was the wild-type EGFR reporter gene expression plasmid, (b) each phRL-TK backbone plasmid (20 ng/well), which was the mutant EGFR reporter gene expression plasmid, and (c) a pSV-β-galactosidase control plasmid (Promega Corp.) (10 ng/well), which was a β-galactosidase gene expression plasmid insusceptible to the RNAi-mediated suppression of expression as an external control, together with various EGFR-siRNAs (shown in Tables 1 to 4; final concentration: 20 nM) designed against the target EGFR dominant mutant genes. The negative control used was an siRNA (final concentration: 20 nM) that did not induce RNAi (siControl; Qiagen N.V.). Lipofectamine 2000 (Invitrogen Corp.) was employed for the introduction of these nucleic acids. The transfection method followed the protocol included in the product. 24 hours after the introduction of the nucleic acids, cell extracts were prepared using (Dual-Luciferase reporter assay system) Passive lysis buffer included in the kit Dual-Luciferase reporter assay system (Promega Corp.). The respective activities of each expressed reporter gene (and two luciferases) and the control β-galactosidase were determined using Dual-Luciferase reporter assay system (Promega Corp.) and Beta-Glo assay system (Promega Corp.). The assay employed Fusion Universal Microplate Analyzer (Perkin Elmer Inc.). In order to further exclude possible measurement errors attributed to the difference in the activities of the two luciferases used as reporters, an experiment was also conducted using reporter genes interchanged among the mutant genes del(E746-A750), del(L747-T751)-L747S, and del(L747-E749)-A750P.

(6) Results

The results of each EGFR-siRNA against the del(E746-A750) mutant gene are shown in FIG. 8-1 B. The results of each EGFR-siRNA against the del(L747-T751)-L747S mutant gene are shown in FIG. 9-1 B. The results of each EGFR-siRNA against the del(L747-E749)-A750P(G) or del(L747-E749)-A750P(A) mutant gene are shown in FIG. 10-1 B or 11-1 B. In each diagram, luciferase activities derived from the non-target wild-type EGFR gene and the target mutant EGFR genes were calculated as their respective relative values with the luciferase activity of siControl as 1.0. The luciferase activity of each sample was corrected with the expression level of β-galactosidase as an external control insusceptible to the RNAi-mediated suppression of expression.

Each RNAi sense strand region had the total base length fixed to 19 bases, but differed one by one in the length of downstream bases from the second reference base to the 3'-terminal base of the RNAi sense strand region. As shown in FIGS. 8-1 B and 9-1 B, the siRNAs in which any one of the 4th to 15th bases downstream from the second reference base was selected as the 3'-terminal base of the RNAi sense strand region (indicated by -4D19 to -15D19) were shown to strongly suppress the expression of the mutant EGFR genes compared with expression suppressed by the control (siControl), but hardly suppress the expression of the wild-type EGFR gene or suppress it at substantially the same level as in the control. This result means that these siRNAs are useful with high ASP-RNAi effects.

As is evident from FIG. 1 B, the siRNAs in which any one of the 2nd to 9th bases downstream therefrom was selected as the 3'-terminal base of the RNAi sense strand region strongly suppressed the expression of the mutant EGFR genes compared with expression suppressed by the control (siControl), but hardly suppressed the expression of the wild-type EGFR gene or suppressed it at substantially the same level as in the control. This result was slightly inconsistent with the results about the del(E746-A750) mutation or the del(L747-T751)-L747S mutation. As shown in FIGS. 10-1 A and 11-1 A, however, the del(L747-E749)-A750P(G) and -A750P(A) mutant gene transcripts each have two points of discontinuity, which are located in the proximity to flank 2 bases and 1 base, respectively. Thus, in this Example, bases 5' and 3' flanking the downstream (3') point of discontinuity were selected, as described above, as first and second reference bases, respectively, as a matter of form to prepare si747/49-2D19 to −9D19 and si747/49(A)-3D19 to −11D19. In other words, bases 5' and 3' flanking the upstream (5') point of discontinuity may be regarded as first and second reference bases, respectively. In this case, the siRNAs are defined as si747/49-4D19 to -11D19 and si747/49(A)-4D19 to −12D19, and the results of these siRNAs are consistent with the results about the del(E746-A750) mutation or the del(L747-T751)-L747S mutation.

The results described above suggested that the selection of any one of the 4th to 15th bases downstream from the second reference base as the 3'-terminal base of the RNAi sense strand region is preferable for designing useful EGFR-siRNAs having high ASP-RNAi effects.

Thus, it cannot be said that as long as an RNAi molecule targeting a transcript containing a point of discontinuity contains two bases (first and second reference bases) flanking the point of discontinuity, the other sequences can be selected arbitrarily. The results described above indicated that desirable ASP-RNAi effects cannot be obtained unless the first and second reference bases are located at the predetermined positions of the RNAi sense strand region. This tendency, albeit with some variations, was shown to be a phenomenon observed regardless of the different nucleotide sequences of target regions in the same gene or different target genes, as also shown in Example 5 described later and FIGS. 12 and 13.

Example 2

Deletion (or Deletion/Insertion) Mutant Gene-Specific RNAi Effect of EGFR-siRNA on Human Non-Small Cell Lung Cancer-Derived Cell Line The EGFR-siRNAs that exhibited effective expression suppressive effects on the mutant EGFR genes del(E746-A750), del(L747-T751)-L747S, del(L747-E749)-A750P in Example 1 were studied for the presence or absence of their specific expression suppressive effects (ASP-RNAi effects) even on endogenous mutant EGFR genes. In this experiment, human lung cancer-derived PC3 cells having the EGFR del (L747-E749)-A750P mutation were used as an example. si747/49-3D19 and si747/49(A)-8D19 particularly having expression suppressive effects on the del(L747-E749)-A750P mutation in Example 1 were used as EGFR-siRNAs to knock down the endogenous mutant EGFR gene by RNAi.

[Method]

(1) Cell Culture

The human non-small cell lung cancer-derived cell line PC3 cells were cultured at 37° C. under 5% $CO_2$ using an EMEM culture solution (Wako Pure Chemical Industries, Ltd.) containing 10% fetal bovine serum (FBS; Invitrogen Corp.).

(2) Introduction of EGFR-siRNA by Electroporation

The cells cultured in the preceding paragraph (1) were dispersed by trypsin digestion, then collected by centrifugation (120 G, 5 min.) and suspended at a concentration of approximately $1 \times 10^6$ cells in 100 µL of an electroporation buffer (Amaxa Cell Line Nucleofector Solution V, Amaxa Biosystems GmbH) containing each EGFR-siRNA (final concentration: 5 µM). These 3 samples for electroporation thus prepared were subjected to nucleic acid introduction (one of the samples was a control experimental group without nucleic acid introduction) by electroporation (program: U-005, gene introduction system Nucleofector, Amaxa Biosystems GmbH) according to the protocol included therein. The introduced nucleic acid was si747/49-3D19, si747/49 (A)-8D19, or a control siRNA (Qiagen N.V.) that did not induce RNAi.

The cells of these 3 groups were separately cultured in a 6-well culture plate using the culture solution of the paragraph (1) and collected 24 hours later.

(3) cDNA Synthesis

From the cells collected in the preceding paragraph (2), total RNAs were collected using TRIzol reagent (Invitrogen Corp.) according to the protocol included therein. Then, cDNAs were synthesized through reverse transcriptase reaction using SuperScript III Reverse Transcriptase (Invitrogen Corp.) and $Oligo(dT)_{15}$ (Promega Corp.) and then treated with RNase H (Invitrogen Corp.). All of these procedures followed the protocols included in the products.

(4) PCR Analysis

The cDNAs obtained in the preceding paragraph (3) were analyzed by PCR using AmpliTaq Gold DNA Polymerase (Applied Biosystems, Inc.) and primers specifically amplifying the EGFR mutation sites and their neighboring sequences. The temperature and time conditions of PCR involved initial denaturation (95° C., 10 min.) followed by 26 cycles each involving 3 steps: denaturation (94° C., 30 sec.), annealing (55° C., 30 sec.), and elongation (72° C., 30 sec.). Then, the PCR amplification products were analyzed by electrophoresis (7% polyacrylamide gel, 100 mA, 1 hr.). The primer sequences used are shown in Table 7.

TABLE 7

| Primer name | Forward(F)/Reverse(R) | Nucleotide sequence (5' → 3') | SEQ ID NO |
|---|---|---|---|
| EGFR | F | CCCAGAAGGTGAGAAAGTTGAAATT | 81 |
|  | R | TCATCGAGGATTTCCTTGTTGGC | 82 |

[Results]

Figure 14:
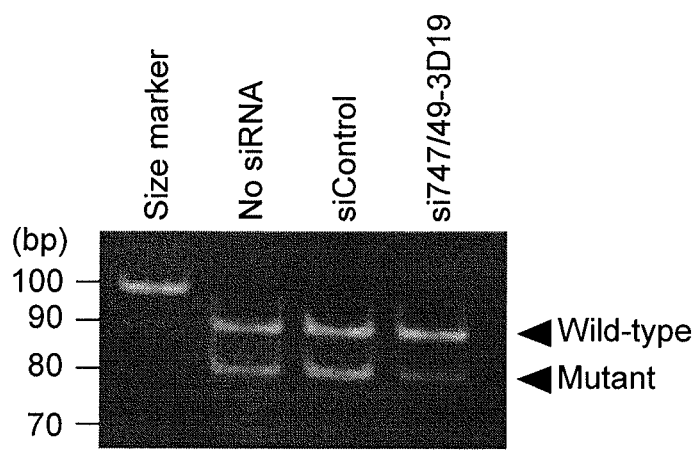
FIG. 14 is an electrophoretic pattern showing a mutant gene-specific RNAi effect in a human non-small cell lung cancer-derived cell line (PC3 cells) when EGFR-siRNA (si747/49-3D19) against EGFR del(L747-E749)-A750P mutation is introduced.
Figure 15:
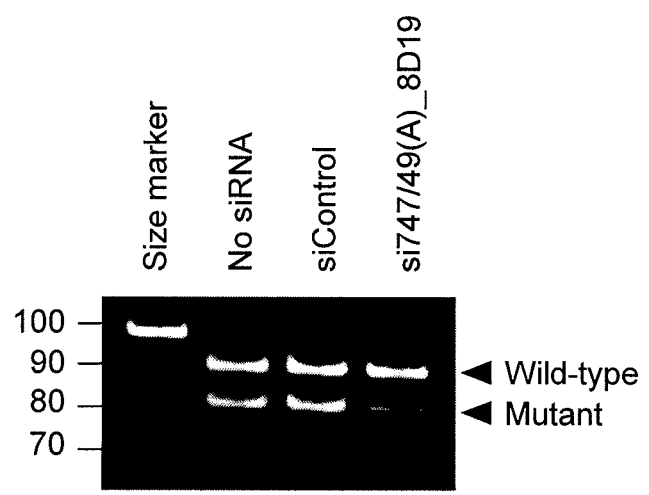
FIG. 15 is an electrophoretic pattern showing a mutant gene-specific RNAi effect in PC3 cells when EGFR-siRNA (si747/49(A)-8D19) is introduced.

The results obtained using si747/49-3D19 and si747/49 (A)-8D19 are shown in FIGS. 14 and 15, respectively. These results demonstrated that both the EGFR-siRNAs specifically and strongly suppressed the expression of the endogenous mutant EGFR gene without suppressing the expression of the wild-type EGFR gene.

Example 3

Evaluation on Influence of EGFR-siRNA on Cell Death and Cell Growth Ability of Human Non-Small Cell Lung Cancer-Derived Cell Line The EGFR-siRNAs (si747/49-3D19 and si747/49(A)-8D19) used in Example 2 were studied for whether or not their specific and effective suppression of the expression of the endogenous mutant EGFR gene (del(L747-E749)-A750P) influenced cell growth or cell death in terms of the total number of cells, cytotoxicity, cell growth and survival activity, and cell death (apoptosis).

(1) Cell Culture

PC3 cells were cultured in the same way as in "Example 2(1)".

(2) Introduction of EGFR-siRNA by Electroporation

Electroporation was performed in the same way as in "Example 2(2)".

The cells were cultured (cell density: approximately $3 \times 10^4$ cells/well) in a 96-well culture plate using the culture solution of the paragraph (1). One day and 4 days later, the cells were subjected to each evaluation experiment. si747/49-3D19 was also subjected to similar evaluation experiments, together with a control, 2 days and 6 days after the cell culture.

1. Cell Growth Ability (Total Number of Cells) Assay

[Method]

In order to examine time-dependent change in the number of PC3 cells (cell growth ability) after the introduction of si747/49-3D19, intracellular lactate dehydrogenase (LDH) level was measured using CytoTox 96(R) Non-Radioactive Cytotoxicity Assay (Promega Corp.). The experiment was conducted according to the protocol included in the product. Briefly, a cell lysis buffer (Lysis Solution (10×)) included in the assay kit was added to the culture solutions of all sample groups. All LDHs contained in all the cells were released by incubation at 37° C. for 45 minutes. This LDH level was measured to indirectly calculate the total number of cells. Absorbance was measured using BenchMark Plus (Bio-Rad Laboratories, Inc.). The negative controls used were a sample non-supplemented with an siRNA (No siRNA) and a sample supplemented with an siRNA that did not induce RNAi (siControl; Qiagen N.V.).

[Results]

Figure 16:
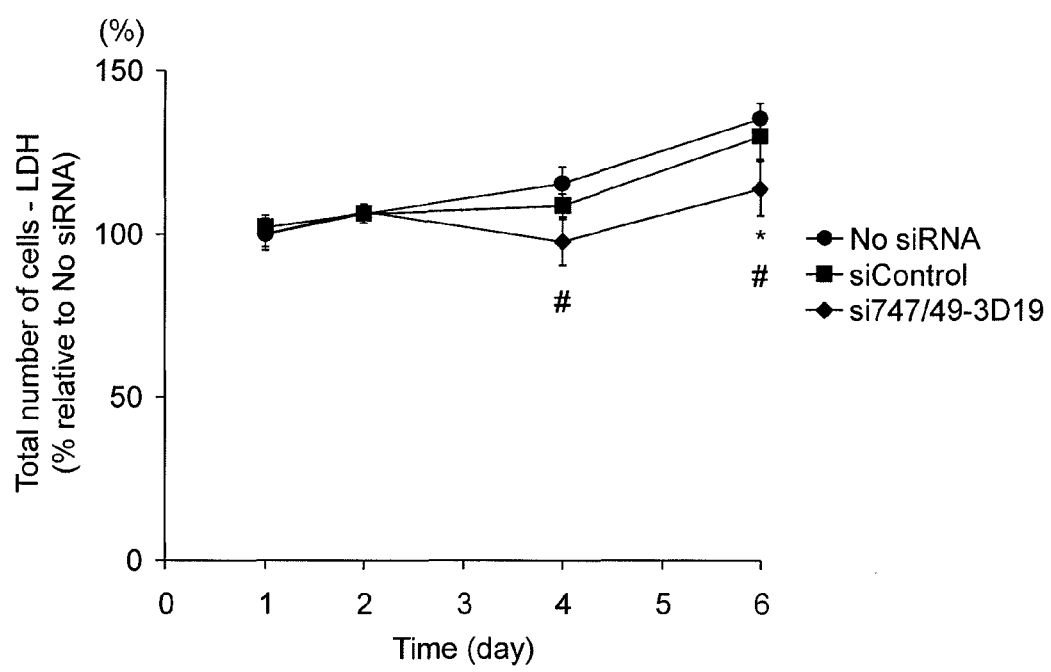
FIG. 16 is a diagram showing the total number of PC3 cells representing the cell growth suppressive effect of EGFR-siRNA (si747/49-3D19) when the siRNA is introduced into PC3 cells.

The results are shown in FIG. 16. In this diagram, the total number of cells is indicated by the relative value (%) of LDH level with the LDH level of "No siRNA" at day 1 as 100%. The EGFR-siRNA (si747/49-3D19) significantly decreased the total number of PC3 cells compared with both "No siRNA" and "siControl". Specifically, this result means that si747/49-3D19 suppressed the cell growth of the PC3 cells. This result also indicates that si747/49-3D19 specifically and effectively suppressed the expression of the PC3 endogenous dominant mutant EGFR (del(L747-E749)-A750P) gene, which promotes cell growth activity by constitutive activation.

2. Cytotoxicity Evaluation

[Method]

In order to evaluate cytotoxicity to PC3 cells after the introduction of si747/49-3D19, the level of LDH released from the cells into a culture solution by cytotoxicity was measured using CytoTox 96 Non-Radioactive Cytotoxicity Assay (Promega Corp.). The experimental procedures followed the protocol included in the product. Absorbance was measured using BenchMark Plus (Bio-Rad Laboratories, Inc.). The negative controls used were the same two controls (No siRNA and siControl) as in the cell growth ability assay.

[Results]

Figure 17:
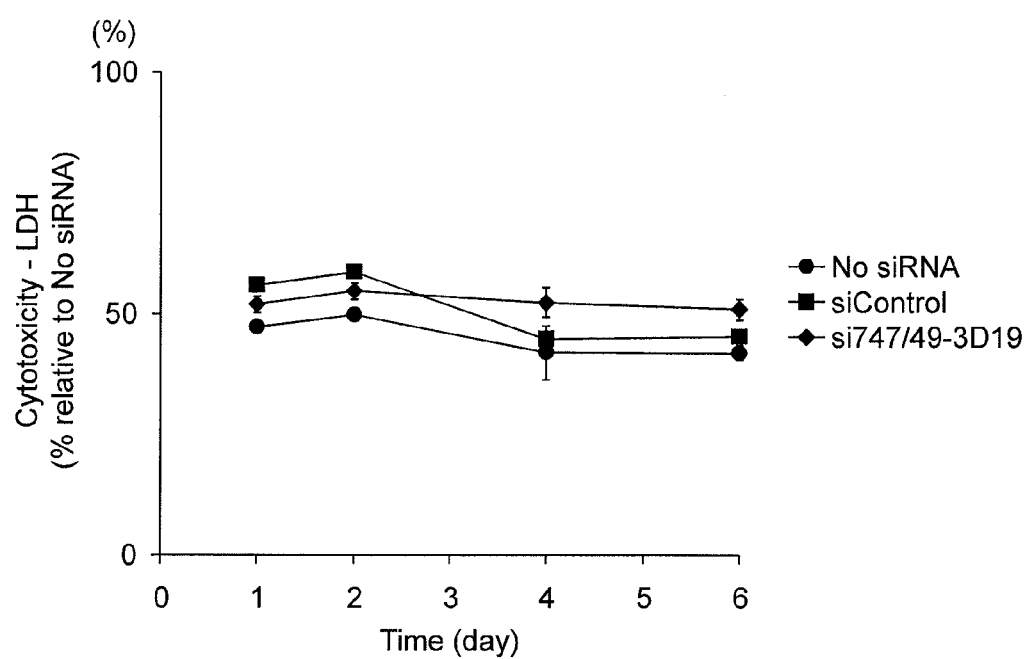
FIG. 17 is a diagram showing the cytotoxic effect of EGFR-siRNA (si747/49-3D19) when the siRNA is introduced into PC3 cells.

The results are shown in FIG. 17. In this diagram, cytotoxicity is indicated by the relative value (%) of LDH level with the level of LDH contained in all the cells of "No siRNA" (the same sample supplemented with the cell lysis buffer as in the cell growth ability assay) at day 1 as 100%. These results demonstrated that si747/49-3D19 does not induce cell death attributed to cytotoxicity or the suppression of the expression of the endogenous mutant EGFR gene, at a level equivalent to or more than "No siRNA" or "siControl".

3. Cell Growth and Survival Activity Evaluation (1)

[Method]

In order to evaluate the cell growth and survival activity of PC3 cells after the introduction of si747/49-3D19, MTS reductive effect induced by nicotinamide adenine dinucleotide (NADH) contained in live cells was measured using CellTiter 96 AQueous Non-Radioactive Cell Proliferation Assay (Promega Corp.). The experimental procedures followed the protocol included in the product. Absorbance was measured using BenchMark Plus (Bio-Rad Laboratories, Inc.). The negative controls used were the same two controls (No siRNA and siControl) as in the cell growth ability assay.

[Results]

Figure 18:
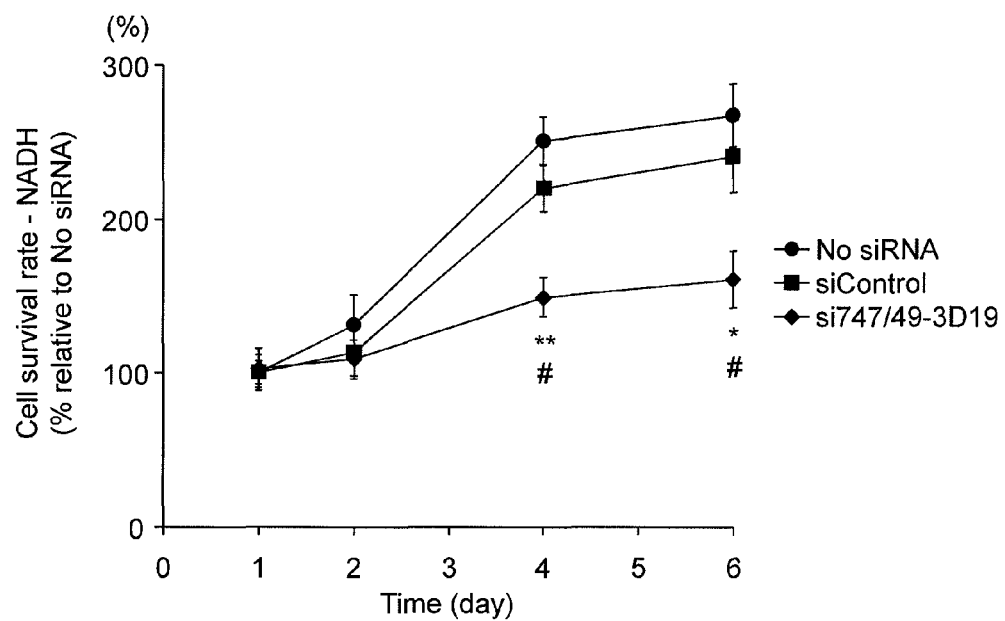
FIG. 18 is a diagram (1) showing the cell growth and survival activity of PC3 cells when EGFR-siRNA (si747/49-3D19) is introduced into PC3 cells.
Figure 19:
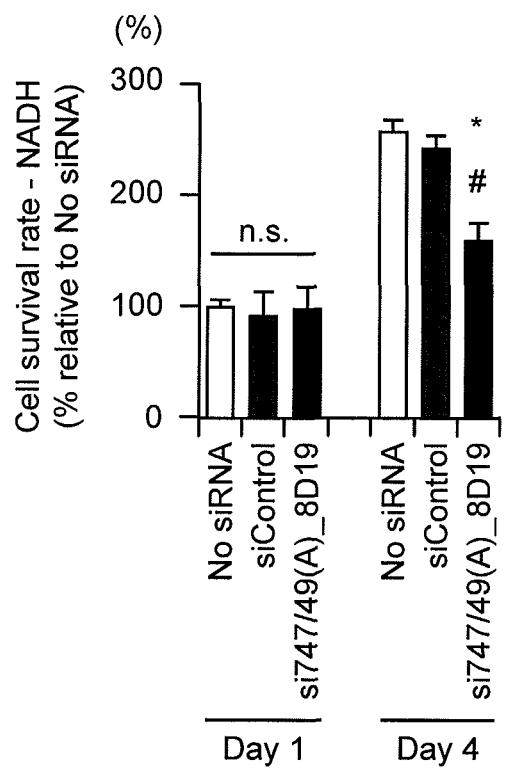
FIG. 19 is a diagram showing the total number of PC3 cells representing the cell growth suppressive effect of EGFR-siRNA (si747/49(A)-8D19) when the siRNA is introduced into PC3 cells.

The results of si747/49-3D19 and the results of si747/49(A)-8D19 are shown in FIGS. 18 and 19, respectively. In these diagrams, cell growth and survival activity (cell survival rate) are indicated by relative values (%) with the NADH activity of "No siRNA" at day 1 as 100%. si747/49-3D19 and si747/49(A)-8D19 significantly suppressed the growth rates of the cells or reduced their survival rates, compared with both "No siRNA" and "siControl".

4. Cell Growth and Survival Activity Evaluation (2)

[Method]

In order to evaluate the cell growth and survival activity of PC3 cells after the introduction of si747/49-3D19, the relative ATP level of the cells was measured using CellTiter-Glo Assay (Promega Corp.). The experimental procedures followed the protocol included in the product. Luminescence intensity was measured using Fusion Universal Microplate Analyzer (Perkin Elmer Inc.). The negative controls used were the same two controls (No siRNA and siControl) as in the cell growth ability assay.

[Results]

Figure 20:
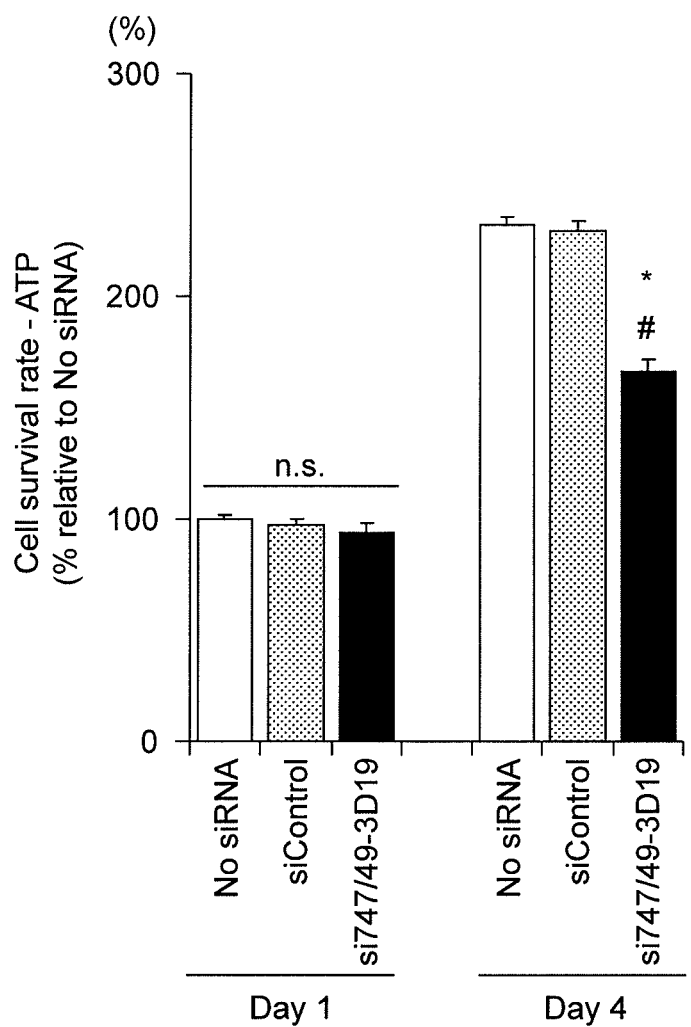
FIG. 20 is a diagram (2) showing the cell growth and survival activity of PC3 cells when EGFR-siRNA (si747/49-3D19) is introduced into PC3 cells.

The results are shown in FIG. 20. Cell growth and survival activity (cell survival rate) are indicated by relative values at days 1 and 4 with the relative ATP level of "No siRNA" at culture day 1 as 100%. As shown in this diagram, si747/49-3D19 significantly suppressed the growth rates of the cells or reduced their survival rates, compared with both "No siRNA" and "siControl" at culture day 4.

5. Cell Death Evaluation

[Method]

In order to evaluate the cell death (apoptosis) of PC3 cells after the introduction of si747/49-3D19, caspase 3/7 activity was measured using Caspase-Glo 3/7 Assay (Promega Corp.). The experimental procedures followed the protocol included in the product. Luminescence intensity was measured using Fusion Universal Microplate Analyzer (Perkin Elmer Inc.). The negative controls used were the same two controls (No siRNA and siControl) as in the cell growth ability assay.

[Results]

Figure 21:
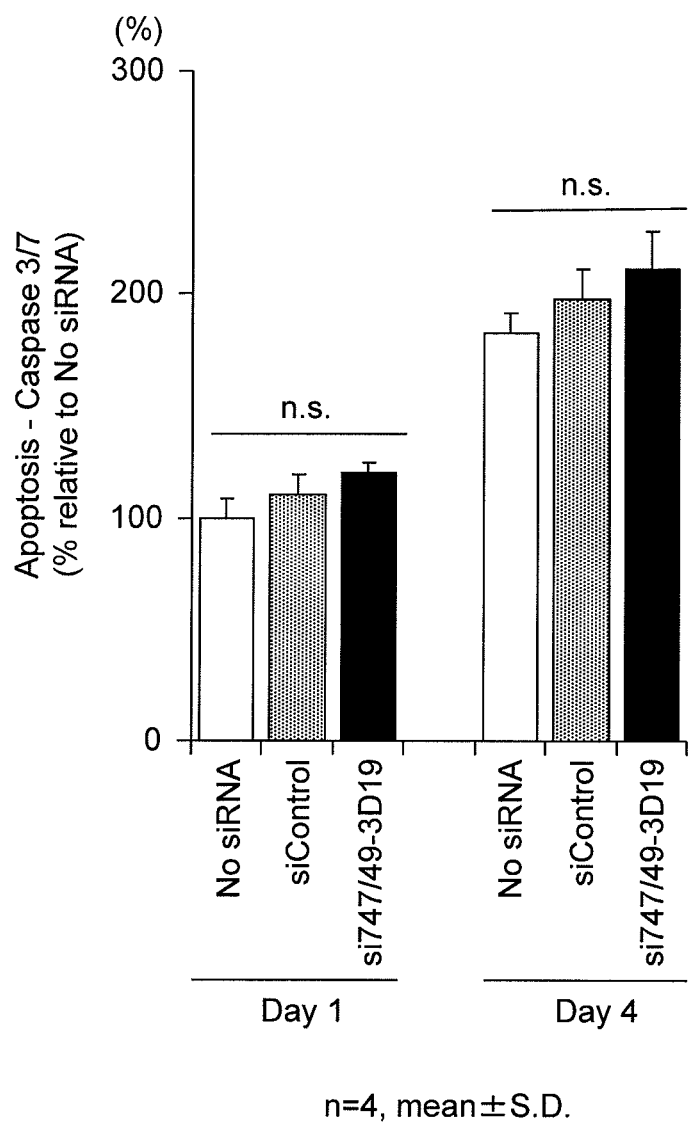
FIG. 21 is a diagram showing the cell death (apoptosis) of PC3 cells when EGFR-siRNA (si747/49-3D19) is introduced into PC3 cells.

The results are shown in FIG. 21. Apoptosis is indicated by the relative values of caspase 3/7 activity at days 1 and 4 with the activity of "No siRNA" at culture day 1 as 100%. As shown in this diagram, si747/49-3D19 did not cause significant change in caspase 3/7 activity compared with both "No siRNA" and "siControl" at culture day 4. This indicates that the mutant EGFR gene-specific suppression of expression by si747/49-3D19 does not induce apoptosis.

Example 4

Point Mutant Gene-Specific RNAi Effect of EGFR-siRNA on Human Non-Small Cell Lung Cancer-Derived Cell Line (1) Test on ASP-RNAi Effect of EGFR-siRNA on EGFR Gene

[Method]

Figure 22:
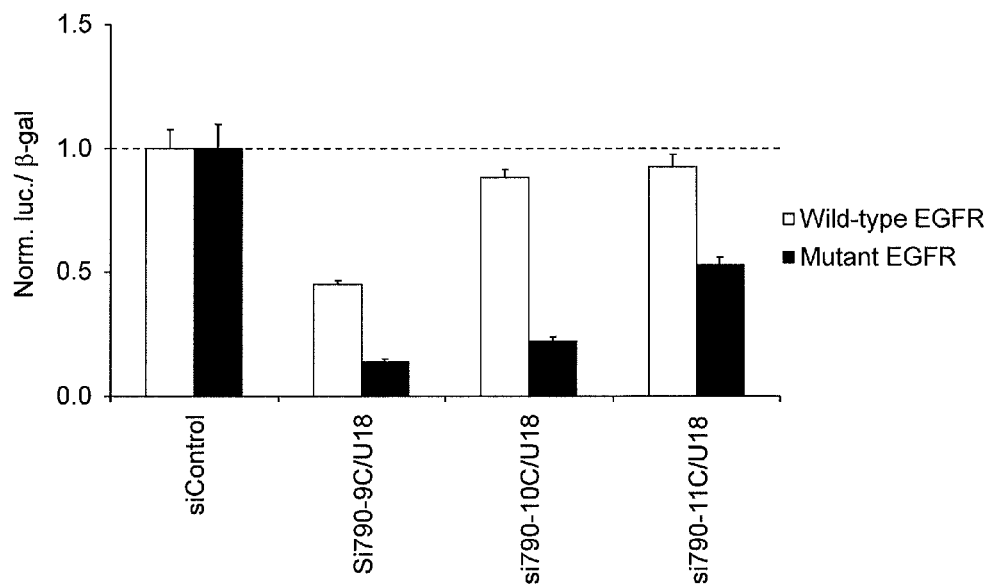
FIG. 22A is a diagram showing the comparison of a substitution site and its neighboring nucleotide sequences (and an amino acid sequence encoded thereby) between the wild-type EGFR gene (SEQ ID NO: 166 nucleotide sequence; SEQ ID NO: 165 amino acid sequence) and the sense strand region of an siRNA designed against T790M mutation in a point mutant (substitution mutant) EGFR gene (SEQ ID NO: 168 nucleotide sequence; SEQ ID NO: 167 amino acid sequence). The base in bold type in the nucleotide sequence of the mutant EGFR gene (SEQ ID NO: 168) corresponds to the substitution site in the mutant EGFR gene.
FIG. 22B shows the expression suppressive effects of EGFR-siRNA on the non-target wild-type EGFR gene and the substitution mutant EGFR gene T790M, wherein these effects were calculated as their respective relative values with the luciferase activity of siControl as 1.0. The luciferase activity was corrected with the expression level of β-galactosidase as an external control insusceptible to the RNAi-mediated suppression of expression.

As described in Example 1, non-small cell lung cancer patients are also known to have a point mutation as a disease-related gain of function mutation in the EGFR gene (Paez G. J. et al., Science, 2004, 304; 1497-1500). Examples of the point mutation include, as shown in FIG. 22A, the point mutation of "T790M mutation" that substitutes the base C at position 2369 by T (the gene point mutation results in the amino acid substitution of tryptophan 790 by methionine (T790M)). A mutant gene having a substitution mutation attributed to such a point mutation is not targeted by the agent for suppressing the expression of a dominant mutant gene according to Example 1 of this application, because its transcript has no point of discontinuity.

However, another siRNA that can specifically suppress the expression of a mutant EGFR gene having a substitution mutation attributed to such a point mutation without influencing the expression of the wild-type EGFR gene and constitutionally differs from the agent for suppressing the expression of a dominant mutant gene according to embodiment 1, and/or an expression vector comprising an operably linked DNA encoding the siRNA can be expected to produce higher suppressive effects by the combined use with the EGFR-siRNA described in Example 1.

Thus, an siRNA specifically suppressing the expression of a point mutant epidermal growth factor receptor (EGFR) gene (this siRNA is also referred to as EGFR-siRNA) was designed and tested for its expression suppressive effect on the mutant gene (cancer-causative gene). Table 8 shows the nucleotide sequences of the sense strand region (ss) and antisense strand region (as) of each siRNA designed against the T790M mutation. The base in bold type in each nucleotide sequence corresponds to the point mutation site. The nucleotide sequences shown in this table are described except for 3'-terminal additional bases consisting of UU at each of the 3' ends of the sense strand and the antisense strand, for the sake of convenience. Also, SEQ ID NOs in the table correspond to numbers in Sequence Listing. As for the EGFR-siRNA names in this table, for example, "si790-9C/U18" in Table 8 represents that: the number of bases from the point mutation site of the T790M mutation to the 5'-terminal base in the sense strand region is 9 bases; the point mutation substitutes the base C on the wild-type EGFR gene by U (T); and the number of bases is 18 bases for both the sense and antisense strand regions.

TABLE 8

| siRNA name | ss/as | Nucleotide sequence (5' → 3') | SEQ ID NO |
|---|---|---|---|
| si790-9C/U18 | ss | GCUCAUCAUGCAGCUCAU | 87 |
| | as | AUGAGCUGCAUGAUGAGC | 88 |
| si790-10C/U18 | ss | AGCUCAUCAUGCAGCUCA | 89 |
| | as | UGAGCUGCAUGAUGAGCU | 90 |
| si790-11C/U18 | ss | CAGCUCAUCAUGCAGCUC | 91 |
| | as | GAGCUGCAUGAUGAGCUG | 92 |

(2) Construction of Reporter Gene Expression Plasmid and Reporter Assay

In order to evaluate and screen the EGFR-siRNAs prepared in the paragraph 1 for their RNAi effects, reporter gene expression plasmids for the dominant mutant genes targeted by the siRNAs and the non-target wild-type gene were constructed and used in cell culture, transfection, and reporter assay. The basic operational procedures followed the methods described in Example 1.

[Results]

The results are shown in FIG. 22B. As shown in this diagram, si790-9C/U18 was not much preferable, because this siRNA had relatively strong suppressive effects on the expression of the wild-type EGFR gene, compared with siControl. By contrast, si790-10C/U18 and si790-11C/U18 were shown to hardly exhibit expression suppressive effects on the wild-type EGFR gene and have effective suppressive effects on the mutant EGFR gene.

These results demonstrated that si790-10C/U18 and si790-11C/U18 are preferable EGFR-siRNAs.

Example 5

Translocation Mutant Gene-Specific RNAi Effect of BCR-ABL-siRNA on BCR-ABL Chimeric Gene An siRNA having the constitution of embodiment 1 was designed against a BCR-ABL chimeric gene attributed to a translocation mutation in Philadelphia chromosome (this siRNA is also referred to as BCR-ABL-siRNA), and tested for its expression suppressive effect on the BCR-ABL chimeric gene causative of leukemia.

[Method]

As described above, BCR-ABL chimeric genes are regarded as causative genes of CML or ALL found in patients having Philadelphia chromosome. The BCR-ABL-siRNA of the present invention that can specifically suppress only the expression of the gain of function mutant BCR-ABL genes can be used as an effective preventive or therapeutic agent for CML or ALL in patients having Philadelphia chromosome.

(1) Type of BCR-ABL Chimeric Gene

Ph translocation breakpoints in the BCR gene are known to concentrate on two sites: Major-BCR (downstream; M-BCR) and minor-BCR (upstream; m-BCR). The involvement of further downstream μ-BCR (p230) has been reported for chronic neutrophilic leukemia and essential thrombocythemia. These mutations results in p210BCR/ABL (M-BCR breakpoint), p190BCR/ABL (m-BCR breakpoint), and p230BCR/ABL (μ-BCR breakpoint) proteins, respectively. Of them, p210BCR/ABL is found in almost all CML cases and Ph-positive ALL cases, while p190BCR/ABL is found in the remaining half of Ph-positive ALL patients.

Thus, each BCR-ABL-siRNA against a BCR-ABL chimeric gene attributed to the M-BCR breakpoint most frequently found in the disease was designed and prepared in accordance with the method for designing the RNAi molecule according to embodiment 1, and tested for the presence or absence of their abilities to specifically suppress the expression of these translocation mutant genes.

(2) Design and Preparation of BCR-ABL-siRNA

Positions corresponding to those indicated by arrowheads in FIGS. 12-1A and 13-1A for the wild-type ABL gene and the wild-type BCL gene, respectively, on a mutant gene product (mutant mRNA) of the BCR-ABL chimeric gene attributed to the M-BCR breakpoint correspond to the point of discontinuity described in the present specification. Bases 5' and 3' flanking this point of discontinuity were selected as first and second reference bases, respectively. BCR-ABL-siRNAs were designed and prepared in the same way as in Example 1.

The specific nucleotide sequences of the BCR-ABL-siRNAs designed and used in this Example are shown in Table 9. Table 9 shows the nucleotide sequences of the sense strand region (ss) and antisense strand region (as) of each siRNA designed against the BCR-ABL chimeric gene attributed to the M-BCR breakpoint. The nucleotide sequences shown in Table 9, however, are described except for 3'-terminal additional bases consisting of UU at each of the 3' ends of the sense strand region and the antisense strand region, for the sake of convenience. Also, SEQ ID NOs in this table correspond to numbers in Sequence Listing.

TABLE 9

| siRNA name | ss/as | Nucleotide sequence (5' → 3') | SEQ ID NO |
|---|---|---|---|
| siBCR/ABL-3D19 | ss | UUUAAGCAGAGUUCAA^CUC | 93 |
|  | as | GAG^UUGAACUCUGCUUAAA | 94 |

TABLE 9-continued

| siRNA name | ss/as | Nucleotide sequence (5' → 3') | SEQ ID NO |
|---|---|---|---|
| siBCR/ABL-4D19 | ss | UUAAGCAGAGUUCAA^CUCU | 95 |
|  | as | AGAG^UUGAACUCUGCUUAA | 96 |
| siBCR/ABL-5D19 | ss | UAAGCAGAGUUCAA^CUCUA | 97 |
|  | as | UAGAG^UUGAACUCUGCUUA | 98 |
| siBCR/ABL-6D19 | ss | AAGCAGAGUUCAA^CUCUAC | 99 |
|  | as | GUAGAG^UUGAACUCUGCUU | 100 |
| siBCR/ABL-7D19 | ss | AGCAGAGUUCAA^CUCUACG | 101 |
|  | as | CGUAGAG^UUGAACUCUGCU | 102 |
| siBCR/ABL-8D19 | ss | GCAGAGUUCAA^CUCUACGU | 103 |
|  | as | ACGUAGAG^UUGAACUCUGC | 104 |
| siBCR/ABL-9D19 | ss | CAGAGUUCAA^CUCUACGUC | 105 |
|  | as | GACGUAGAG^UUGAACUCUG | 106 |
| siBCR/ABL-10D19 | ss | AGAGUUCAA^CUCUACGUCU | 107 |
|  | as | AGACGUAGAG^UUGAACUCU | 108 |
| siBCR/ABL-11D19 | ss | GAGUUCAA^CUCUACGUCUC | 109 |
|  | as | GAGACGUAGAG^UUGAACUC | 110 |
| siBCR/ABL-12D19 | ss | AGUUCAA^CUCUACGUCUCC | 111 |
|  | as | GGAGACGUAGAG^UUGAACU | 112 |
| siBCR/ABL-13D19 | ss | GUUCAA^CUCUACGUCUCCU | 113 |
|  | as | AGGAGACGUAGAG^UUGAAC | 114 |
| siBCR/ABL-14D19 | ss | UUCAA^CUCUACGUCUCCUC | 115 |
|  | as | GAGGAGACGUAGAG^UUGAA | 116 |
| siBCR/ABL-15D19 | ss | UCAA^CUCUACGUCUCCUCC | 117 |
|  | as | GGAGGAGACGUAGAG^UUGA | 118 |
| siBCR/ABL-16D19 | ss | CAA^CUCUACGUCUCCUCCG | 119 |
|  | as | CGGAGGAGACGUAGAG^UUG | 120 |

The synthesis of each siRNA was outsourced to Sigma-Aldrich Corp. The synthesized siRNAs each had a sense strand region and an antisense strand region annealed to each other, and were used directly in experiments.

(3) Construction of Reporter Gene Expression Plasmid

The methods for constructing reporter gene expression plasmids, designing synthetic oligo-DNAs containing the mutation site, inserting the DNAs into the reporter gene expression plasmids, and screening for suitable siRNAs followed the methods described in "(3) Construction of reporter gene expression plasmid" of Example 1. The specific nucleotide sequences of the synthetic oligo-DNAs used are shown in Table 10.

TABLE 10

| Sequence name | ss/as | Nucleotide sequence (5' → 3') | SEQ ID NO |
|---|---|---|---|
| BCR/ABL | ss | CTAGCATGCTTTAAGCAGAGTTCAA^TCTACGTCTCCTCCGA | 121 |
|  | as | GGCCTCGGAGGAGACGTAGAG^TTGAACTCTGCTTAAGCATG | 122 |
| ABL | ss | CTAGCATGCTGCTTCTGATGGCAAGCTCTACGTCTCCTCCGA | 123 |
|  | as | GGCCTCGGAGGAGACGTAGAGCTTGCCATCAGAAGCAGCATG | 124 |
| BCR | ss | CTAGCATGCTTTAAGCAGAGTTCAAATCTGTACTGCACCCTGA | 125 |
|  | as | GGCCTCAGGGTGCAGTACAGATTTGAACTCTGCTTAAGCATG | 126 |

(4) Cell Culture

Cells were cultured in accordance with the method described in "(4) Cell culture" of Example 1.

(5) Transfection and Reporter Assay

These procedures followed the method described in "(5) Transfection and reporter assay" of Example 1.

[Results]

The results of each BCR-ABL-siRNA against the BCR-ABL chimeric gene are shown in FIGS. 12-1 B and 13-1 B. In order to evaluate each BCR-ABL-siRNA for its expression suppressive effect specific for the gene, this effect must be evaluated on the BCR-ABL chimeric gene and two wild-type genes (ABL gene and BCR gene). In this regard, the target gene-specific expression suppressive effect of each BCR-ABL-siRNA was evaluated using the BCR-ABL chimeric gene combined with the wild-type ABL gene (FIG. 12-1 B) and the BCR-ABL chimeric gene combined with the wild-type BCR gene (FIG. 13-1 B). In each diagram, as described above, luciferase activities derived from the non-target wild-type ABL or BCR gene and the target BCR-ABL chimeric gene were calculated as their respective relative values with the luciferase activity of siControl as 1.0. The luciferase activity of each sample was corrected with the expression level of β-galactosidase as an external control insusceptible to the RNAi-mediated suppression of expression.

Each RNAi sense strand region had the total base length fixed to 19 bases, but differed one by one in the length of downstream bases from the second reference base to the 3'-terminal base of the siRNA sense strand region. As shown in FIGS. 12-1 B and 13-1 B, the siRNAs in which any one of the 4th to 13th bases downstream from the second reference base was selected as the 3'-terminal base of the RNAi sense strand region (indicated by -4D19 to -13D19) were shown to strongly suppress the expression of the BCR-ABL chimeric gene compared with expression suppressed by the control (siControl), but hardly suppress the expression of the wild-type ABL or BCR gene or suppress it at substantially the same level as in the control. This result means that these siRNAs are useful with high ASP-RNAi effects.

As in "Example 1" above, the results described above demonstrated that the selection of any one of the 4th to 15th bases downstream from the second reference base as the 3'-terminal base of the RNAi sense strand region is preferable for designing useful BCR-ABL-siRNAs having high ASP-RNAi effects.

Example 6

Influence of EGFR-siRNA and Anticancer Agent Gefitinib on Cell Survival Activity of Human Non-Small Cell Lung Cancer-Derived Cell Line Each EGFR-siRNA that specifically suppressed the expression of the mutant EGFR gene having del(L747-E749)-A750P mutation or del(E746-A750) mutation in Example 1, and an anticancer agent gefitinib reportedly effective for non-small cell lung cancer expressing mutant EGFR were used and studied for their influence on cell growth and cell survival activity.

[Method]

(1) Cell Culture

The analysis employed human non-small cell lung cancer-derived cell line PC3 cells and PC9 cells having EGFR del(L747-E749)-A750P mutation and del(E746-A750) mutation, respectively, and control human HeLa cells having wild-type EGFR. The PC3 cells were cultured in the same way as in "Example 2:(1)". The HeLa cells were cultured in the same way as in "Example 1:(4)". The PC9 cells were cultured at 37° C. under 5% $CO_2$ using an RPMI-1640 culture solution (Wako Pure Chemical Industries, Ltd.) containing 10% fetal bovine serum (FBS; Invitrogen Corp.).

(2) Gefitinib Treatment

The cultured PC3 cells, PC9 cells, and HeLa cells were separately dispersed by trypsin digestion, then collected by centrifugation (120 G, 5 min.), and cultured (cell density: approximately $1\times10^5$ cells/cm$^2$) in a 96-well culture plate. 24 hours later, the cells were exposed to 0, $10^{-3}$, $10^{-2}$, $10^{-1}$, $10^0$, and $10^1$ μM (final concentration) gefitinib (trade name: Iressa; AstraZeneca plc). 3 days later, cell survival activity was measured.

(3) Introduction of EGFR-siRNA into PC3 Cell by Electroporation

The EGFR-siRNA was introduced in to the cells in the same way as in "Example 2:(2)". Specifically, the PC3 cells cultured using the culture solution of the paragraph (1) were dispersed by trypsin digestion, then collected by centrifugation (120 G, 5 min.) and suspended at a concentration of approximately $1\times10^6$ cells in 100 μL of an electroporation buffer (Amaxa Cell Line Nucleofector Solution V, Amaxa Biosystems GmbH) containing the EGFR-siRNA (si747/49-3D19) or an siRNA that did not induce RNAi (siControl; Qiagen N.V.) (final concentration: 100, 50, 25, 10, 5, 1, and 0 nM). Each siRNA was introduced into the cells by electroporation (program: U-005, gene introduction system Nucleofector, Amaxa Biosystems GmbH) according to the protocol included therein. The cells were cultured in the medium described in "Example 2:(1)". 3 days later, cell survival activity was measured.

(4) Introduction of EGFR-siRNA into PC9 Cell by Lipofection

The cells were cultured (cell density: approximately $1\times10^5$ cells/cm$^2$) in a 96-well culture plate in the same way as in the paragraph (1). The EGFR-siRNA (si746/50-4D19) or an siRNA that did not induce RNAi (siControl; Qiagen N.V.) (final concentration: 100, 50, 25, 10, 5, 1, and 0 nM) was introduced into PC9 cells using Lipofectamine 2000 (Invitrogen Corp.). The transfection procedures followed the protocol included therein. After 3 days of culture, cell survival activity was measured.

(5) Cell Growth and Survival Activity Evaluation

Evaluation was performed in the same way as in "Example 3; 3. Cell growth and survival activity evaluation (1)".

[Results]

(1) Influence of Gefitinib on Cell Growth and Survival Activity

Figure 23:
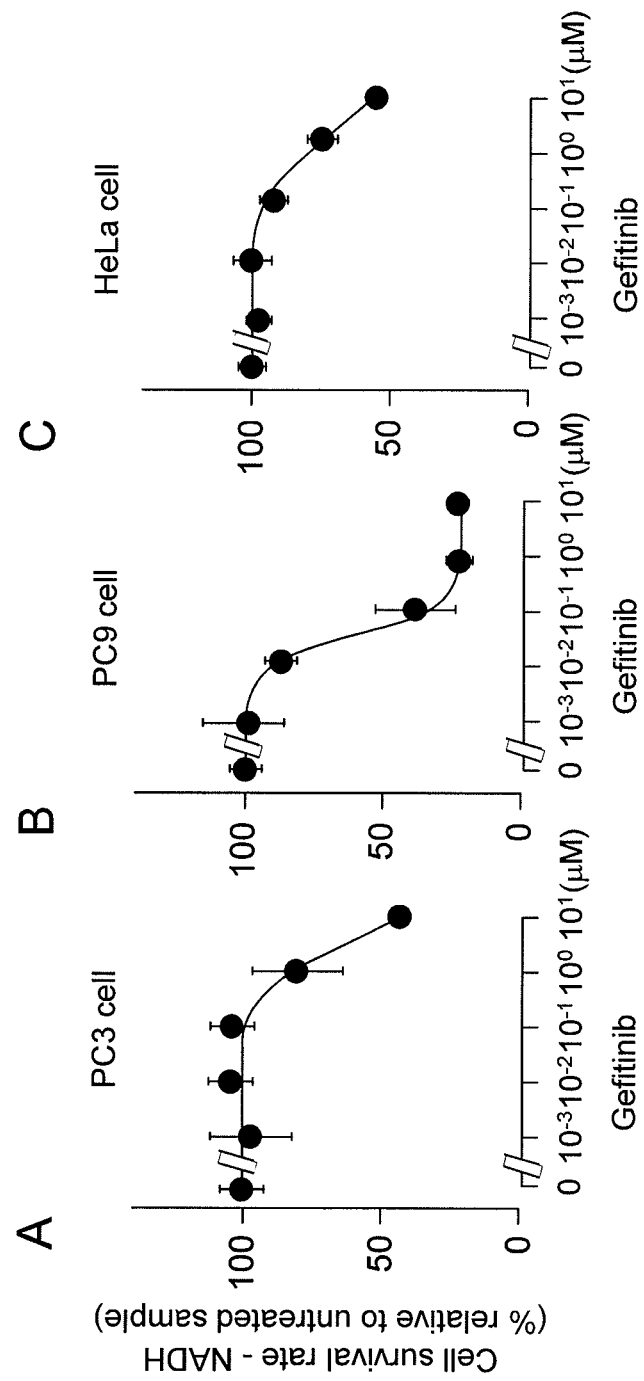
FIG. 23 is a diagram showing the cell growth and survival activity of each of PC3 cells (human non-small cell lung cancer-derived cell line having mutant EGFR del(L747-E749)-A750P), PC9 cells (human non-small cell lung cancer-derived cell line having mutant EGFR del(E746-A750)), and HeLa cells (human uterine cervix cancer-derived cell line having wild-type EGFR) exposed to an anticancer agent gefitinib at varying concentrations.

The results of evaluating the influence of gefitinib on the cell growth and survival activity of each cell are shown in FIGS. 23A to 23C. FIG. 23A shows the results about the PC3 cells having del(L747-E749)-A750P mutation. FIG. 23B shows the results about the PC9 cells having del(E746-A750) mutation. FIG. 23C shows the results about the HeLa cells. In each diagram, the values are indicated as relative values with the survival activity of their respective untreated cells as 100%.

The PC9 cells apparently exhibited suppressed cell growth and reduced survival activity in the presence of gefitinib with a concentration of $10^{-2}$ μM or higher, whereas the PC3 cells and the HeLa cells exhibited suppressed cell growth and reduced survival activity in a concentration-dependent manner in the presence of 1 μM or higher gefitinib. This result suggested that the PC9 cells are gefitinib-sensitive cells whose growth can be suppressed by the administration of gefitinib in small amounts, whereas the PC3 cells are gefitinib-resistant cells whose cell growth and survival activity are insusceptible to the suppressive effect of gefitinib unless gefitinib is administered at a high concentration that influences even the HeLa cells, i.e., suppresses even cells having wild-type EGFR.

The results described above demonstrated that gefitinib may serve as an effective anticancer agent for non-small cell lung cancer having a gefitinib-sensitive EGFR mutation such as del(E746-A750) mutation, but does not produce effects on non-small cell lung cancer that has del(L747-E749)-A750P mutation and has acquired gefitinib resistance unless gefitinib is administered at a high concentration that may have adverse reaction on recipient individuals.

In fact, it has been reported that the efficacy of gefitinib is closely related to a mutation in the EGFR gene (Paez G. J. et al. Science, 2004, 304; 1497-1500; and Lynch T. J. et al. N Engl J Med, 2004, 350; 2129-2139). The administration of gefitinib is known to produce dramatic therapeutic effects on patients having a gefitinib-sensitive EGFR mutation, but possibly bring about adverse reaction such as interstitial pneumonia or acute lung injury to patients having a gefitinib-resistant EGFR mutation. The results of this Example also support this fact.

(2) Influence of EGFR-siRNA on Cell Growth and Survival Activity

Figure 24:
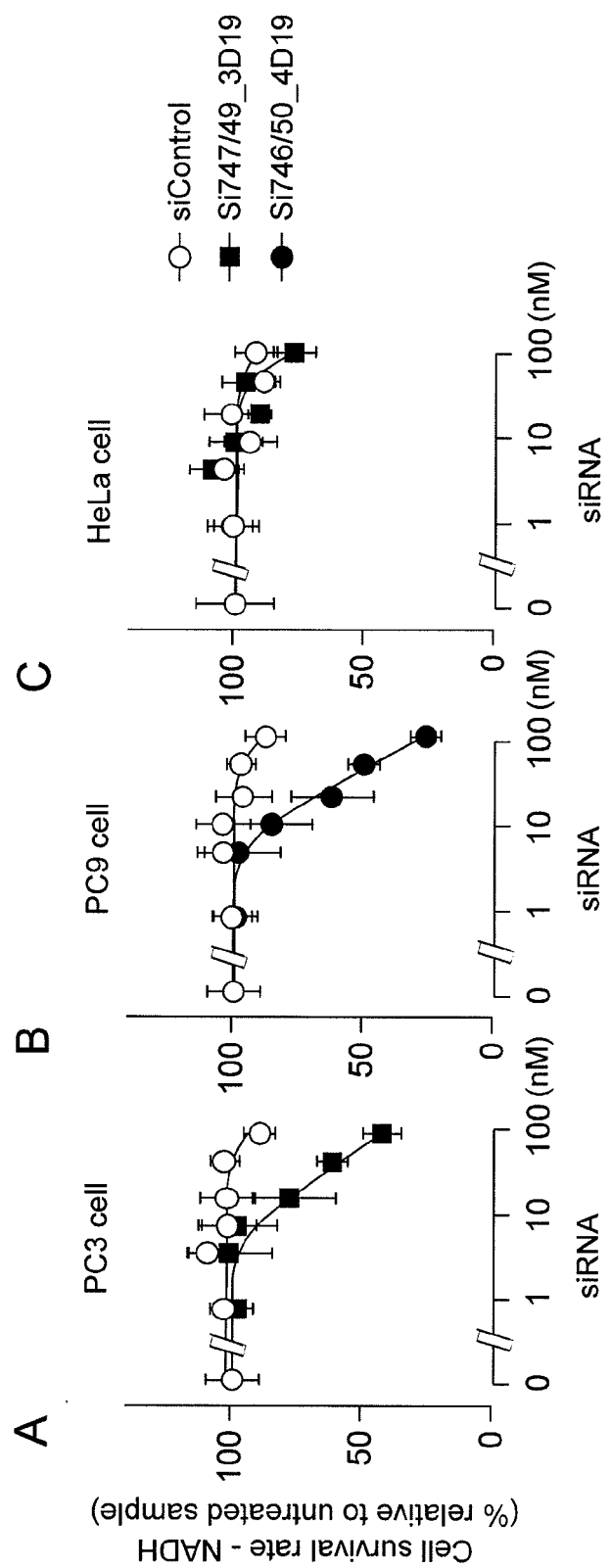
FIG. 24 is a diagram showing the cell growth and survival activity of each of PC3 cells, PC9 cells, and HeLa cells to which EGFR-siRNA was administered at varying concentrations.

The results of examining the influence of each EGFR-siRNA on the cell growth and survival activity of each cell are shown in FIGS. 24A to 24C.

FIG. 24A shows the results of the EGFR-siRNA (si747/49-3D19) on PC3 cells having del(L747-E749)-A750P mutation. FIG. 24B shows the results of the EGFR-siRNA (si746/50-4D19) on PC9 cells having del(E746-A750) mutation. FIG. 24C shows the results of the EGFR-siRNA (si747/49-3D19) on HeLa cells. In each diagram, the values are indicated as relative values with the survival activity of their respective untreated cells as 100%.

As shown in this diagram, the EGFR-siRNAs (si746/50-4D19 and si747/49-3D19) were observed to apparently suppress cell growth and reduce survival activity for both the PC3 cells and the PC9 cells having the EGFR mutation. By contrast, neither of the EGFR-siRNAs exhibited suppressive effects on the cell growth and survival activity of the HeLa cells having wild-type EGFR.

The results described above demonstrated that the EGFR-siRNA of the present invention hardly influences the expression of the wild-type EGFR gene (i.e., the EGFR-siRNA of the present invention has no or minimal adverse reaction) and can induce the suppression of cell growth and reduction in survival activity with exceedingly high specificity for both gefitinib-resistant and gefitinib-sensitive EGFR mutations at a concentration lower than that of gefitinib.

Example 7

Preparation of Mouse Model by Xenoectopic Transplantation of Human Non-Small Cell Lung Cancer-Derived Cell Line and Effect of EGFR-siRNA Thereon The effects of each EGFR-siRNA studied at the cell level were tested at the individual level.

[Method]

PC3 cells were subcutaneously transplanted to nude mice to prepare mouse models with subcutaneous tumor. The mouse models were used to test tumor growth inhibitory effects by the administration of each EGFR-siRNA.

(1) Preparation of Mouse Model by Xenoectopic Transplantation of Human Non-Small Cell Lung Cancer-Derived PC3 Cell (i) Cell Culture The PC3 cells were cultured in the same way as in "Example 2:(1)".

(ii) Transplantation of PC3 Cell

The cultured PC3 cells were dispersed by trypsin digestion, then collected by centrifugation (120 G, 5 min.), and resuspended in a serum- and antibiotic-free culture solution (RPMI-1640, Wako Pure Chemical Industries, Ltd.) to adjust the number of cells to $1 \times 10^7$ cells/mL. This cell suspension and BD Matrigel Basement Membrane Matrix (Becton, Dickinson and Company) were mixed in equal amounts to adjust the number of cells to $5 \times 10^6$ cells/mL. This suspension was subcutaneously administered at a dose of 100 µL (0.5× $10^6$ cells) to the right flank region of each immunodeficient model nude mouse (5 weeks old, BALB/cAJcl-nu/nu, CLEA Japan, Inc.).

(2) Administration of EGFR-siRNA to Subcutaneous Tumor in Mouse (i) Preparation and Administration of EGFR-siRNA A nucleic acid delivery vehicle AteloGene (registered trademark) Local Use (Koken Co., Ltd.) composed mainly of atelocollagen was complexed with si747/49-3D19 or si747/49(A)-8D19 that exhibited effective cell growth suppressive effects on PC3 cells in Examples 1 to 3. The complexing procedures followed the protocol included therein. The final concentration of each EGFR-siRNA (si747/49-3D 19 or si747/49(A)-8D 19) was set to 0.1 mg/mL. An siRNA that did not induce RNAi (siControl; Qiagen N.V.) was similarly complexed, and an siRNA-free atelocollagen solution was also prepared for control experiments.

(ii) Administration of siRNA to Subcutaneous Tumor

One week after PC3 cell transplantation (6 weeks old), tumor volume was calculated from tumor diameters. Three samples prepared above, i.e., the siRNA-free atelocollagen solution and 20 µg/200 µL solutions of siControl and each EGFR-siRNA were separately administered once at a dose of 1.0 mg/kg body weight directly to the tumor that reached approximately 50 mm³. The tumor volume was calculated according to the following equation:

$$\text{Volume} = (\text{minor axis})^2 \times (\text{major axis}) \times 0.5$$

(iii) Follow-Up after siRNA Administration

Figure 25:
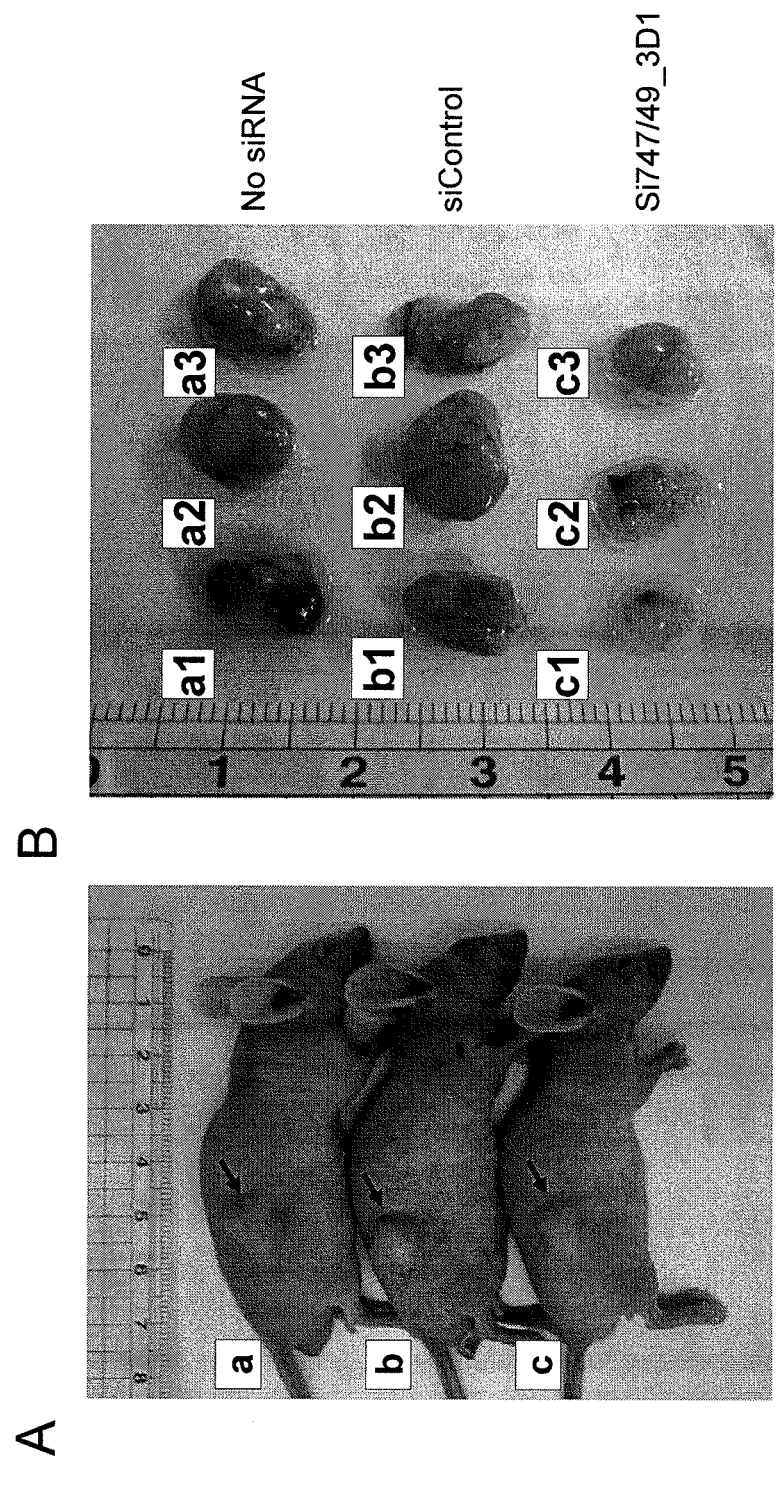
FIG. 25A shows nude mice in the 3rd week (9 weeks old) after administration of an siRNA or the like to a tumor (indicated by arrow) derived from subcutaneously transplanted PC3 cells. a represents an individual that received no siRNA. b represents an individual that received siControl. c represents individual that received EGFR-siRNA (si747/49-3D19).
FIG. 25B shows PC3 cell-derived tumors excised, in the 3rd week (9 weeks old) after administration of an siRNA or the like, from a population (a1 to a3) that received no siRNA, a population (b1 to b3) that received siControl, and a population (c1 to c3) that received EGFR-siRNA (si747/49-3D19).
Figure 28:
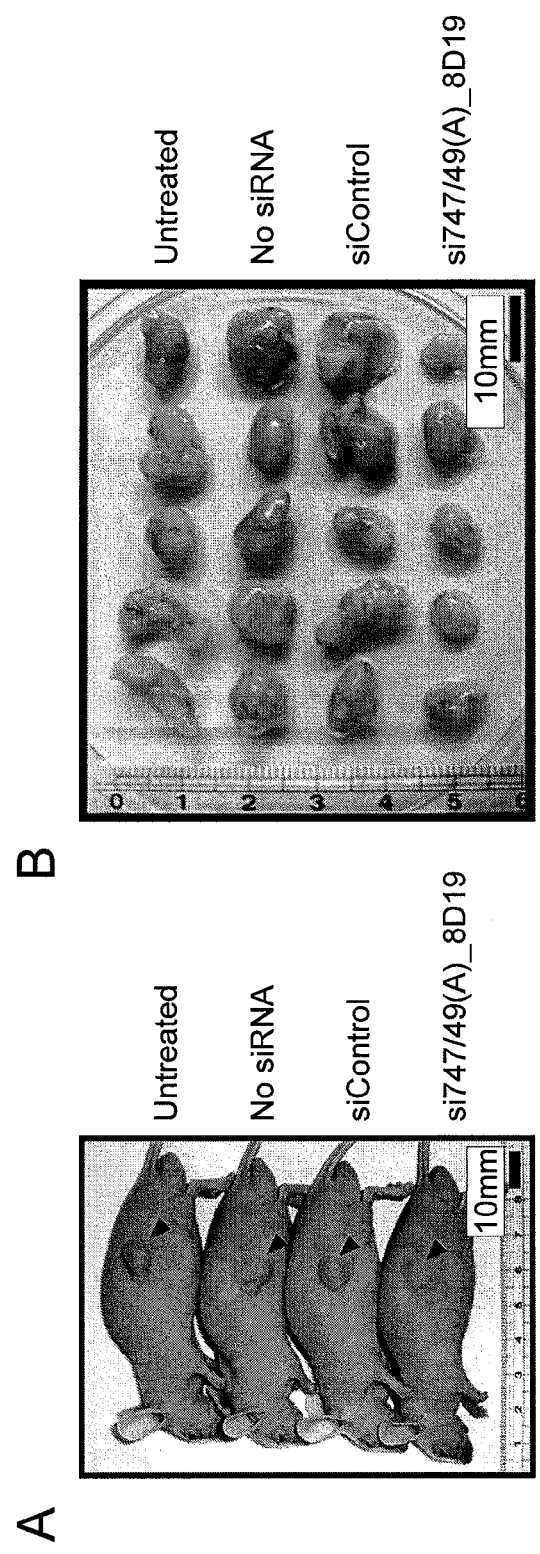

In the 3rd week after the administration of the siRNA, etc. (9 weeks old) (FIG. 25A, si747/49-3D19; FIG. 28A, si747/49(A)-8D19), the tumor volume was calculated according to the equation. In addition, the tumor was taken out of each mouse (FIG. 25B, si747/49-3D19; FIG. 28B, si747/49(A)-8D19), and its wet weight was measured.

[Results]

Figure 26:
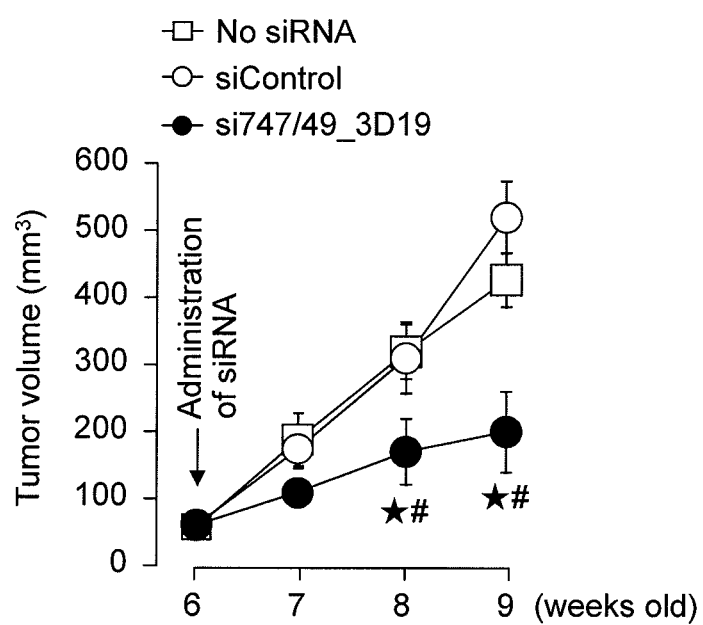
FIG. 26 is a diagram showing time-dependent change in tumor volume caused by administration of EGFR-siRNA (si747/49-3D19) to PC3 cells subcutaneously transplanted to nude mice. The asterisk represents the presence of significant difference ($p<0.05$) compared with the tumor volume of an individual that received no siRNA. The mark # represents the presence of significant difference ($p<0.05$) compared with the tumor volume of an individual that received siControl.
Figure 27:
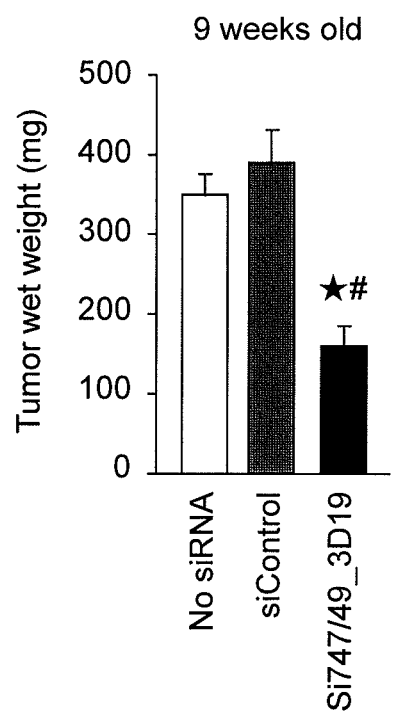
FIG. 27 is a diagram showing tumor wet weight attributed to administration of EGFR-siRNA (si747/49-3D19) to PC3 cells subcutaneously transplanted to nude mice. The asterisk represents the presence of significant difference ($p<0.05$) compared with the tumor wet weight of an individual that received no siRNA. The mark # represents the presence of significant difference ($p<0.05$) compared with the tumor wet weight of an individual that received siControl.
Figure 29:
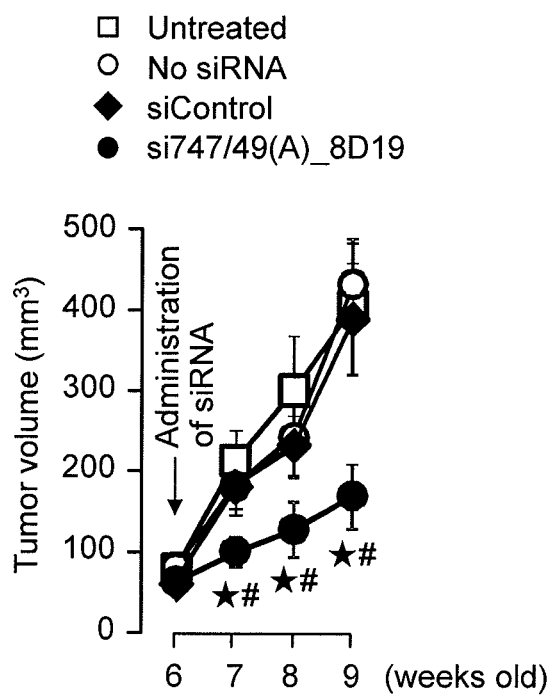
FIG. 29 is a diagram showing time-dependent change in tumor volume caused by administration of EGFR-siRNA (si747/49(A)-8D19) to PC3 cells subcutaneously transplanted to nude mice. The asterisk represents the presence of significant difference ($p<0.05$) compared with the tumor volume of an individual that received no siRNA. The mark # represents the presence of significant difference ($p<0.05$) compared with the tumor volume of an individual that received siControl.
Figure 30:
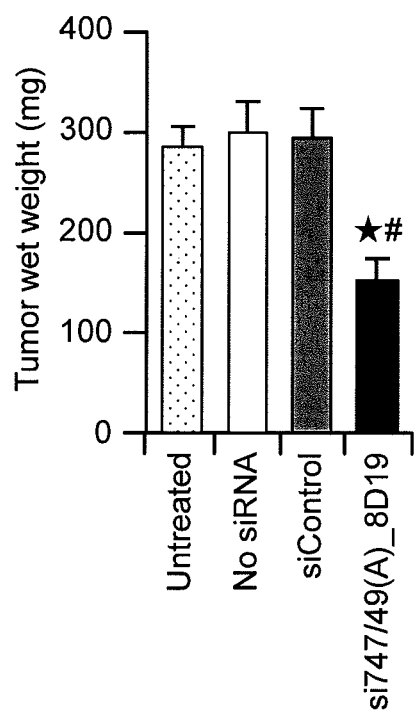
FIG. 30 is a diagram showing tumor wet weight attributed to administration of EGFR-siRNA (si747/49(A)-8D19) to PC3 cells subcutaneously transplanted to nude mice. The asterisk represents the presence of significant difference ($p<0.05$) compared with the tumor wet weight of an individual that received no siRNA. The mark # represents the presence of significant difference ($p<0.05$) compared with the tumor wet weight of an individual that received siControl.

Time-dependent change in tumor volume caused by the administration of each EGFR-siRNA is shown in FIG. 26 (administration of si747/49-3D19) and FIG. 29 (administration of si747/49(A)-8D19). The wet weight of the excised tumor is shown in FIG. 27 (administration of si747/49-3D19) and FIG. 30 (administration of si747/49(A)-8D19). The administration of the EGFR-siRNA (si747/49-3D19 or si747/49(A)-8D19) to the population was shown to significantly suppress the swelling of the subcutaneous tumor, compared with only the atelocollagen solution administered to the population and siControl administered to the population. The wet weight of the tumor was also significantly reduced by the administration of the EGFR-siRNA (si747/49-3D19 or si747/49(A)-8D19), compared with these controls.

From the results described above, the EGFR-siRNA of the present invention was confirmed to be effective for suppressing cancer cell growth not only at the cell level but at the individual level. These results also demonstrated that the EGFR-siRNA of the present invention can exceedingly effectively and safely suppress even the growth and survival activity of cancer cells having a gefitinib-resistant EGFR mutation for which the administration of gefitinib has not previously been used due to its large adverse reaction.

The presence or absence of mutant EGFR genes in the cancer cells of non-small cell lung cancer patients can be tested by a highly sensitive detection method such as LNA-PNA-PCR clamp method (JP Patent No. 4216266). Gefitinib may serve as an exceedingly effective therapeutic agent for patients having EGFR genes having a gefitinib-sensitive mutation such as del(E746-A750) mutation. However, none of the previously known drugs are effective without adverse reaction for cancer cells that have a mutation such as del (L747-E749)-A750P but have acquired gefitinib resistance. The EGFR-siRNA of the present invention was shown to be able to serve as a very effective anticancer agent even for non-small cell lung cancer patients having such a gefitinib-resistant EGFR gene mutation for which an effective treatment method has not been established.

Example 8

Test on Adverse Reaction Attributed to Suppression of Expression of Endogenous Wild-Type EGFR Gene As demonstrated by Examples described above, the EGFR-siRNA of the present invention specifically suppresses the expression of only a mutant EGFR gene, whereas the conventional siRNA strongly suppresses the expression of both wild-type and mutant EGFR genes without differentiating therebetween. Thus, the EGFR-siRNA of the present invention and the conventional siRNA were tested for the presence or absence of adverse reaction attributed to their administration to mouse individuals.

[Method]

Various siRNAs were intraperitoneally administered to ICR mice (male, 10 weeks old). A total of four experimental groups were used: a group that received no siRNA and received only an atelocollagen solution (No siRNA); a group that received an siRNA that did not induce RNAi (siControl; Qiagen N.V.); a group that received si747/49-3D19 specifically suppressing the expression of the mutant EGFR gene; and a group that received siEgfr suppressing the expression of the endogenous wild-type EGFR gene residing in vivo in mice. These test samples were prepared in the same way as in Example 7 and intraperitoneally administered to mice. The specific nucleotide sequences of the siEgfr designed and used in this Example are shown in Table 11.

TABLE 11

| siRNA name | ss/as | Nucleotide sequence (5' → 3') | SEQ ID NO |
|---|---|---|---|
| siEgfr | ss | GGAGGGACAUCGUCCAAAAUU | 127 |
|  | as | UUUUGGACGAUGUCCCUCCUU | 128 |

3 days after administration, blood was collected from each mouse. The collected total blood was centrifuged (1200×g, 10 min.) to obtain plasma. Subsequently, total bilirubin, indirect bilirubin, and direct bilirubin levels in the plasma were measured using QuantiChrom™ Bilirubin Assay Kit (BioAssay Systems LLC). Also, alkaline phosphatase level was measured using LabAssay™ ALP (Wako Pure Chemical Industries, Ltd.). The experimental procedures followed the protocol included in each kit.

[Results]

Figure 31:
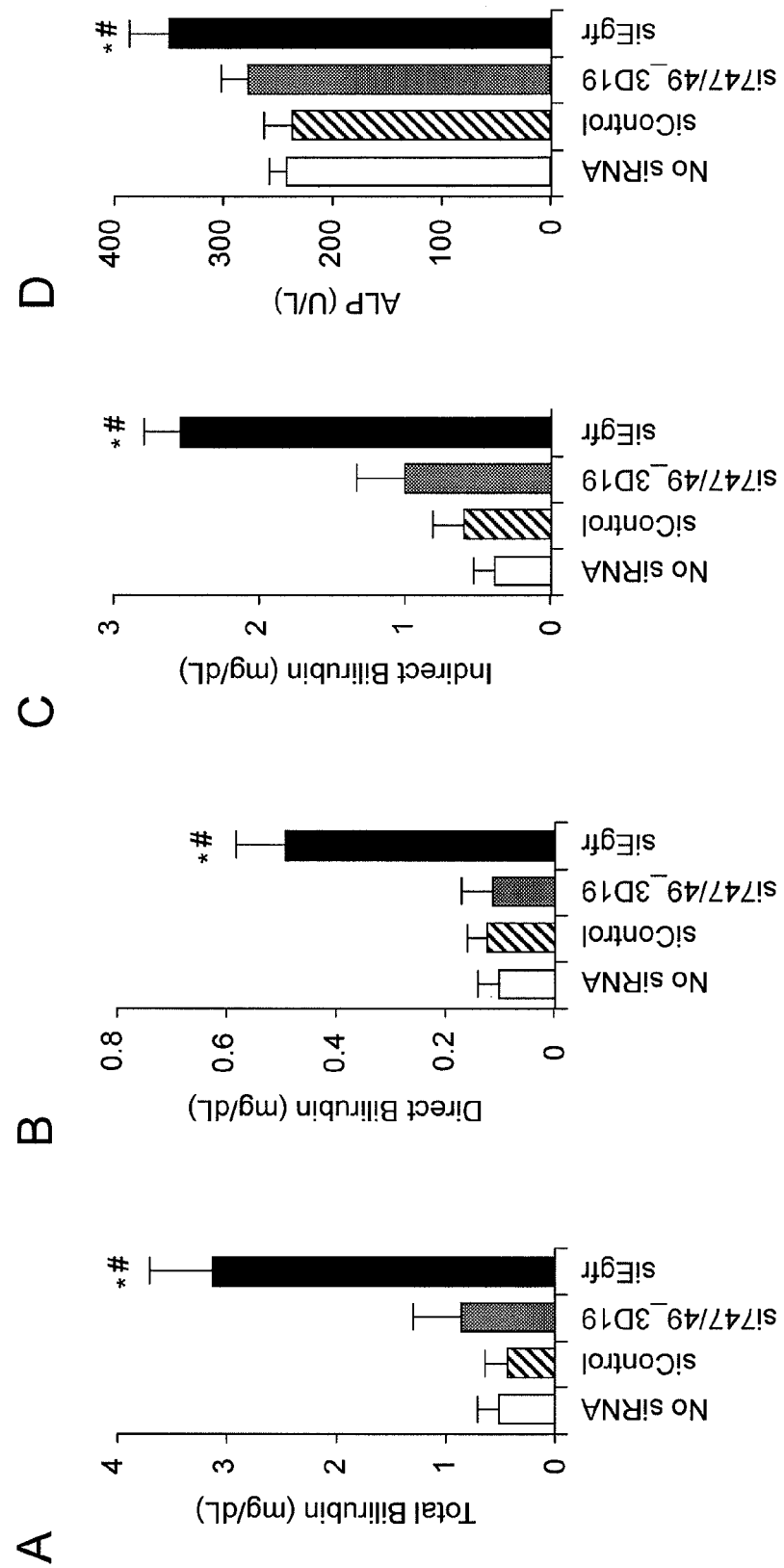
FIG. 31 shows the influence of adverse reaction of EGFR-siRNA on mouse individual.

The results are shown in FIG. 31. A significant rise in the levels of total bilirubin (FIG. 31 A), direct bilirubin (FIG. 31 B), indirect bilirubin (FIG. 31 C), and alkaline phosphatase (FIG. 31 D) in the plasma was observed in the group that received siEgfr suppressing the expression of the endogenous wild-type EGFR gene, compared with the No siRNA group and the siControl-administered group. By contrast, no significant change was observed in the group that received the EGFR-siRNA (si747/49-3D19) of the present invention. This significant rise in plasma parameters was attributed to the expression of the endogenous wild-type EGFR gene suppressed by the administration of siEgfr. The data on the changed plasma parameters suggested the induced disorder of the hepatobiliary system. The endogenous wild-type EGFR gene is necessary for hepatic cellular regeneration (Natarajan et al., 2007, Proc Natl Acad Sci USA., Vol. 104: 17081-17086). In conclusion, these results suggested that the suppression of the expression of the endogenous wild-type EGFR gene carries a risk of causing very serious adverse reaction. By contrast, it was demonstrated that the administration of the EGFR-siRNA of the present invention does not influence the plasma parameters and hardly influences the expression of the endogenous wild-type EGFR gene. This result suggests that the EGFR-siRNA of the present invention, unlike the conventional EGFR-siRNA, carries no or very low risk of causing adverse reaction such as the disorder of the hepatobiliary system as described above. This demonstrated usefulness of the RNA interference technique using the agent for suppressing the expression of a dominant mutant gene according to the present invention.

All publications, patents, and patent applications cited herein are incorporated herein by reference in their entirety.

The invention claimed is:

1. A double-stranded RNA (dsRNA) molecule that is between 19-30 base-pairs in length and that comprises a sense strand and an antisense strand fully complementary to the sense strand, wherein the sense strand comprises a sequence selected from the group consisting of SEQ ID Nos: 29, 31, 33, 35, 37, 39, 41, 43, 45, 47 and 49.

2. An agent for suppressing the expression of EGFR gene containing del(L747-T751)-L747S mutation, comprising the dsRNA molecule according to claim 1 as an active ingredient.

3. An agent for suppressing the expression of EGFR gene containing del(L747-T751)-L747S mutation, comprising an expression vector comprising an operably linked DNA encoding the dsRNA molecule according to claim 1 as an active ingredient.

4. The suppressing agent according to claim 2 or 3, wherein the dsRNA molecule is an siRNA or an shRNA.

5. A pharmaceutical composition comprising at least one suppressing agent according to claim 2 or 3 as an active ingredient.

6. The pharmaceutical composition according to claim 5, further comprising, as an active ingredient: an RNAi molecule whose sense strand region consists of a nucleotide sequence represented by SEQ ID NO: 83 or 85, and/or an expression vector comprising an operably linked DNA transcribing the nucleotide sequence represented by SEQ ID NO: 83 or 85; and/or an RNAi molecule whose sense strand region consists of a nucleotide sequence represented by SEQ ID NO: 89, and/or an expression vector comprising an operably linked DNA transcribing the nucleotide sequence represented by SEQ ID NO: 89.

* * * * *

SEQUENCE LISTING

```
<160> NUMBER OF SEQ ID NOS: 168

<210> SEQ ID NO 1
<211> LENGTH: 19
<212> TYPE: RNA
<213> ORGANISM: Homo sapiens

<400> SEQUENCE: 1
uucccgucgc uaucaaaac                                                  19
```

```
<210> SEQ ID NO 2
<211> LENGTH: 19
<212> TYPE: RNA
<213> ORGANISM: Homo sapiens

<400> SEQUENCE: 2
guuuugauag cgacgggaa                                                  19

<210> SEQ ID NO 3
<211> LENGTH: 19
<212> TYPE: RNA
<213> ORGANISM: Homo sapiens

<400> SEQUENCE: 3
ucccgucgcu aucaaaaca                                                  19

<210> SEQ ID NO 4
<211> LENGTH: 19
<212> TYPE: RNA
<213> ORGANISM: Homo sapiens

<400> SEQUENCE: 4 uguuugaua gcgacggga                                                   19

<210> SEQ ID NO 5
<211> LENGTH: 19
<212> TYPE: RNA
<213> ORGANISM: Homo sapiens

<400> SEQUENCE: 5
cccgucgcua ucaaaacau                                                  19

<210> SEQ ID NO 6
<211> LENGTH: 19
<212> TYPE: RNA
<213> ORGANISM: Homo sapiens

<400> SEQUENCE: 6 auguuugau agcgacggg                                                   19

<210> SEQ ID NO 7
<211> LENGTH: 19
<212> TYPE: RNA
<213> ORGANISM: Homo sapiens

<400> SEQUENCE: 7
ccgucgcuau caaaacauc                                                  19

<210> SEQ ID NO 8
<211> LENGTH: 19
<212> TYPE: RNA
<213> ORGANISM: Homo sapiens

<400> SEQUENCE: 8
gauguuuuga uagcgacgg                                                  19

<210> SEQ ID NO 9
<211> LENGTH: 19
<212> TYPE: RNA
<213> ORGANISM: Homo sapiens

<400> SEQUENCE: 9
cgucgcuauc aaaacaucu                                                  19
```

<210> SEQ ID NO 10
<211> LENGTH: 19
<212> TYPE: RNA
<213> ORGANISM: Homo sapiens

<400> SEQUENCE: 10
agauguuuug auagcgacg                                              19

<210> SEQ ID NO 11
<211> LENGTH: 19
<212> TYPE: RNA
<213> ORGANISM: Homo sapiens

<400> SEQUENCE: 11
gucgcuauca aaacaucuc                                              19

<210> SEQ ID NO 12
<211> LENGTH: 19
<212> TYPE: RNA
<213> ORGANISM: Homo sapiens

<400> SEQUENCE: 12
gagauguuuu gauagcgac                                              19

<210> SEQ ID NO 13
<211> LENGTH: 19
<212> TYPE: RNA
<213> ORGANISM: Homo sapiens

<400> SEQUENCE: 13
cgcuaucaaa acaucuccg                                              19

<210> SEQ ID NO 14
<211> LENGTH: 19
<212> TYPE: RNA
<213> ORGANISM: Homo sapiens

<400> SEQUENCE: 14
cggagauguu uugauagcg                                              19

<210> SEQ ID NO 15
<211> LENGTH: 19
<212> TYPE: RNA
<213> ORGANISM: Homo sapiens

<400> SEQUENCE: 15
gcuaucaaaa caucuccga                                              19

<210> SEQ ID NO 16
<211> LENGTH: 19
<212> TYPE: RNA
<213> ORGANISM: Homo sapiens

<400> SEQUENCE: 16
ucggagaugu uuugauagc                                              19

<210> SEQ ID NO 17
<211> LENGTH: 19
<212> TYPE: RNA
<213> ORGANISM: Homo sapiens

<400> SEQUENCE: 17
cuaucaaaac aucuccgaa                                              19

```
<210> SEQ ID NO 18
<211> LENGTH: 19
<212> TYPE: RNA
<213> ORGANISM: Homo sapiens

<400> SEQUENCE: 18
uucggagaug uuuugauag                                                      19

<210> SEQ ID NO 19
<211> LENGTH: 19
<212> TYPE: RNA
<213> ORGANISM: Homo sapiens

<400> SEQUENCE: 19
uaucaaaaca ucuccgaaa                                                      19

<210> SEQ ID NO 20
<211> LENGTH: 19
<212> TYPE: RNA
<213> ORGANISM: Homo sapiens

<400> SEQUENCE: 20
uuucggagau guuuugaua                                                      19

<210> SEQ ID NO 21
<211> LENGTH: 19
<212> TYPE: RNA
<213> ORGANISM: Homo sapiens

<400> SEQUENCE: 21
aucaaaacau cuccgaaag                                                      19

<210> SEQ ID NO 22
<211> LENGTH: 19
<212> TYPE: RNA
<213> ORGANISM: Homo sapiens

<400> SEQUENCE: 22
cuuucggaga uguuuugau                                                      19

<210> SEQ ID NO 23
<211> LENGTH: 19
<212> TYPE: RNA
<213> ORGANISM: Homo sapiens

<400> SEQUENCE: 23
ucaaaacauc uccgaaagc                                                      19

<210> SEQ ID NO 24
<211> LENGTH: 19
<212> TYPE: RNA
<213> ORGANISM: Homo sapiens

<400> SEQUENCE: 24
gcuuucggag auguuuuga                                                      19

<210> SEQ ID NO 25
<211> LENGTH: 19
<212> TYPE: RNA
<213> ORGANISM: Homo sapiens

<400> SEQUENCE: 25
```
caaaacaucu ccgaaagcc                                                19

<210> SEQ ID NO 26
<211> LENGTH: 19
<212> TYPE: RNA
<213> ORGANISM: Homo sapiens

<400> SEQUENCE: 26
ggcuuucgga gauguuuug                                                19

<210> SEQ ID NO 27
<211> LENGTH: 19
<212> TYPE: RNA
<213> ORGANISM: Homo sapiens

<400> SEQUENCE: 27
gucgcuauca aggaaucau                                                19

<210> SEQ ID NO 28
<211> LENGTH: 19
<212> TYPE: RNA
<213> ORGANISM: Homo sapiens

<400> SEQUENCE: 28
augauuccuu gauagcgac                                                19

<210> SEQ ID NO 29
<211> LENGTH: 19
<212> TYPE: RNA
<213> ORGANISM: Homo sapiens

<400> SEQUENCE: 29
ucgcuaucaa ggaaucauc                                                19

<210> SEQ ID NO 30
<211> LENGTH: 19
<212> TYPE: RNA
<213> ORGANISM: Homo sapiens

<400> SEQUENCE: 30
gaugauuccu ugauagcga                                                19

<210> SEQ ID NO 31
<211> LENGTH: 19
<212> TYPE: RNA
<213> ORGANISM: Homo sapiens

<400> SEQUENCE: 31
cgcuaucaag gaaucaucu                                                19

<210> SEQ ID NO 32
<211> LENGTH: 19
<212> TYPE: RNA
<213> ORGANISM: Homo sapiens

<400> SEQUENCE: 32
agaugauucc uugauagcg                                                19

<210> SEQ ID NO 33
<211> LENGTH: 19
<212> TYPE: RNA
<213> ORGANISM: Homo sapiens

<400> SEQUENCE: 33

```
gcuaucaagg aaucaucuc                                              19

<210> SEQ ID NO 34
<211> LENGTH: 19
<212> TYPE: RNA
<213> ORGANISM: Homo sapiens

<400> SEQUENCE: 34
gagaugauuc cuugauagc                                              19

<210> SEQ ID NO 35
<211> LENGTH: 19
<212> TYPE: RNA
<213> ORGANISM: Homo sapiens

<400> SEQUENCE: 35
cuaucaagga aucaucucc                                              19

<210> SEQ ID NO 36
<211> LENGTH: 19
<212> TYPE: RNA
<213> ORGANISM: Homo sapiens

<400> SEQUENCE: 36
ggagaugauu ccuugauag                                              19

<210> SEQ ID NO 37
<211> LENGTH: 19
<212> TYPE: RNA
<213> ORGANISM: Homo sapiens

<400> SEQUENCE: 37
aucaaggaau caucuccga                                              19

<210> SEQ ID NO 38
<211> LENGTH: 19
<212> TYPE: RNA
<213> ORGANISM: Homo sapiens

<400> SEQUENCE: 38
ucggagauga uuccuugau                                              19

<210> SEQ ID NO 39
<211> LENGTH: 19
<212> TYPE: RNA
<213> ORGANISM: Homo sapiens

<400> SEQUENCE: 39
ucaaggaauc aucuccgaa                                              19

<210> SEQ ID NO 40
<211> LENGTH: 19
<212> TYPE: RNA
<213> ORGANISM: Homo sapiens

<400> SEQUENCE: 40
uucggagaug auuccuuga                                              19

<210> SEQ ID NO 41
<211> LENGTH: 19
<212> TYPE: RNA
<213> ORGANISM: Homo sapiens
```

```
<400> SEQUENCE: 41
caaggaauca ucuccgaaa                                                19

<210> SEQ ID NO 42
<211> LENGTH: 19
<212> TYPE: RNA
<213> ORGANISM: Homo sapiens

<400> SEQUENCE: 42
uuucggagau gauuccuug                                                19

<210> SEQ ID NO 43
<211> LENGTH: 19
<212> TYPE: RNA
<213> ORGANISM: Homo sapiens

<400> SEQUENCE: 43
aaggaaucau cuccgaaag                                                19

<210> SEQ ID NO 44
<211> LENGTH: 19
<212> TYPE: RNA
<213> ORGANISM: Homo sapiens

<400> SEQUENCE: 44
cuuucggaga ugauuccuu                                                19

<210> SEQ ID NO 45
<211> LENGTH: 19
<212> TYPE: RNA
<213> ORGANISM: Homo sapiens

<400> SEQUENCE: 45
aggaaucauc uccgaaagc                                                19

<210> SEQ ID NO 46
<211> LENGTH: 19
<212> TYPE: RNA
<213> ORGANISM: Homo sapiens

<400> SEQUENCE: 46
gcuuucggag augauuccu                                                19

<210> SEQ ID NO 47
<211> LENGTH: 19
<212> TYPE: RNA
<213> ORGANISM: Homo sapiens

<400> SEQUENCE: 47
ggaaucaucu ccgaaagcc                                                19

<210> SEQ ID NO 48
<211> LENGTH: 19
<212> TYPE: RNA
<213> ORGANISM: Homo sapiens

<400> SEQUENCE: 48
ggcuuucgga gaugauucc                                                19

<210> SEQ ID NO 49
<211> LENGTH: 19
<212> TYPE: RNA
<213> ORGANISM: Homo sapiens
```

<400> SEQUENCE: 49
gaaucaucuc cgaaagcca                                                19

<210> SEQ ID NO 50
<211> LENGTH: 19
<212> TYPE: RNA
<213> ORGANISM: Homo sapiens

<400> SEQUENCE: 50
uggcuuucgg agaugauuc                                                19

<210> SEQ ID NO 51
<211> LENGTH: 19
<212> TYPE: RNA
<213> ORGANISM: Homo sapiens

<400> SEQUENCE: 51
aaucaucucc gaaagccaa                                                19

<210> SEQ ID NO 52
<211> LENGTH: 19
<212> TYPE: RNA
<213> ORGANISM: Homo sapiens

<400> SEQUENCE: 52
uuggcuuucg gagaugauu                                                19

<210> SEQ ID NO 53
<211> LENGTH: 19
<212> TYPE: RNA
<213> ORGANISM: Homo sapiens

<400> SEQUENCE: 53
cgucgcuauc aaggagcca                                                19

<210> SEQ ID NO 54
<211> LENGTH: 19
<212> TYPE: RNA
<213> ORGANISM: Homo sapiens

<400> SEQUENCE: 54
uggcuccuug auagcgacg                                                19

<210> SEQ ID NO 55
<211> LENGTH: 19
<212> TYPE: RNA
<213> ORGANISM: Homo sapiens

<400> SEQUENCE: 55
gucgcuauca aggagccaa                                                19

<210> SEQ ID NO 56
<211> LENGTH: 19
<212> TYPE: RNA
<213> ORGANISM: Homo sapiens

<400> SEQUENCE: 56
uuggcuccuu gauagcgac                                                19

<210> SEQ ID NO 57
<211> LENGTH: 19
<212> TYPE: RNA

<213> ORGANISM: Homo sapiens

<400> SEQUENCE: 57
ucgcuaucaa ggagccaac                                                    19

<210> SEQ ID NO 58
<211> LENGTH: 19
<212> TYPE: RNA
<213> ORGANISM: Homo sapiens

<400> SEQUENCE: 58
guuggcuccu ugauagcga                                                    19

<210> SEQ ID NO 59
<211> LENGTH: 19
<212> TYPE: RNA
<213> ORGANISM: Homo sapiens

<400> SEQUENCE: 59
cgcuaucaag gagccaaca                                                    19

<210> SEQ ID NO 60
<211> LENGTH: 19
<212> TYPE: RNA
<213> ORGANISM: Homo sapiens

<400> SEQUENCE: 60
uguuggcucc uugauagcg                                                    19

<210> SEQ ID NO 61
<211> LENGTH: 19
<212> TYPE: RNA
<213> ORGANISM: Homo sapiens

<400> SEQUENCE: 61
gcuaucaagg agccaacau                                                    19

<210> SEQ ID NO 62
<211> LENGTH: 19
<212> TYPE: RNA
<213> ORGANISM: Homo sapiens

<400> SEQUENCE: 62
auguuggcuc cuugauagc                                                    19

<210> SEQ ID NO 63
<211> LENGTH: 19
<212> TYPE: RNA
<213> ORGANISM: Homo sapiens

<400> SEQUENCE: 63
cuaucaagga gccaacauc                                                    19

<210> SEQ ID NO 64
<211> LENGTH: 19
<212> TYPE: RNA
<213> ORGANISM: Homo sapiens

<400> SEQUENCE: 64
gauguuggcu ccuugauag                                                    19

<210> SEQ ID NO 65
<211> LENGTH: 19

```
<212> TYPE: RNA
<213> ORGANISM: Homo sapiens

<400> SEQUENCE: 65
uaucaaggag ccaacaucu                                                 19

<210> SEQ ID NO 66
<211> LENGTH: 19
<212> TYPE: RNA
<213> ORGANISM: Homo sapiens

<400> SEQUENCE: 66
agauguuggc uccuugaua                                                 19

<210> SEQ ID NO 67
<211> LENGTH: 19
<212> TYPE: RNA
<213> ORGANISM: Homo sapiens

<400> SEQUENCE: 67
aucaaggagc caacaucuc                                                 19

<210> SEQ ID NO 68
<211> LENGTH: 19
<212> TYPE: RNA
<213> ORGANISM: Homo sapiens

<400> SEQUENCE: 68
gagauguugg cuccuugau                                                 19

<210> SEQ ID NO 69
<211> LENGTH: 35
<212> TYPE: DNA
<213> ORGANISM: Homo sapiens

<400> SEQUENCE: 69
ctagcatgcg tgcagctcat cacgcagctc atgca                               35

<210> SEQ ID NO 70
<211> LENGTH: 35
<212> TYPE: DNA
<213> ORGANISM: Homo sapiens

<400> SEQUENCE: 70
ggcctgcatg agctgcgtga tgagctgcac gcatg                               35

<210> SEQ ID NO 71
<211> LENGTH: 35
<212> TYPE: DNA
<213> ORGANISM: Homo sapiens

<400> SEQUENCE: 71
ctagcatgcg tgcagctcat catgcagctc atgca                               35

<210> SEQ ID NO 72
<211> LENGTH: 35
<212> TYPE: DNA
<213> ORGANISM: Homo sapiens

<400> SEQUENCE: 72
ggcctgcatg agctgcatga tgagctgcac gcatg                               35

<210> SEQ ID NO 73
```

<211> LENGTH: 67
<212> TYPE: DNA
<213> ORGANISM: Homo sapiens

<400> SEQUENCE: 73
ctagcatgca ttcccgtcgc tatcaaggaa ttaagagaag caacatctcc gaaagccaac    60
aaggaaa    67

<210> SEQ ID NO 74
<211> LENGTH: 67
<212> TYPE: DNA
<213> ORGANISM: Homo sapiens

<400> SEQUENCE: 74
ggcctttcct tgttggcttt cggagatgtt gcttctctta attccttgat agcgacggga    60
atgcatg    67

<210> SEQ ID NO 75
<211> LENGTH: 52
<212> TYPE: DNA
<213> ORGANISM: Homo sapiens

<400> SEQUENCE: 75
ctagcatgca ttcccgtcgc tatcaaaaca tctccgaaag ccaacaagga aa    52

<210> SEQ ID NO 76
<211> LENGTH: 52
<212> TYPE: DNA
<213> ORGANISM: Homo sapiens

<400> SEQUENCE: 76
ggcctttcct tgttggcttt cggagatgtt ttgatagcga cgggaatgca tg    52

<210> SEQ ID NO 77
<211> LENGTH: 55
<212> TYPE: DNA
<213> ORGANISM: Homo sapiens

<400> SEQUENCE: 77
ctagcatgca ttcccgtcgc tatcaaggaa tcatctccga aagccaacaa ggaaa    55

<210> SEQ ID NO 78
<211> LENGTH: 55
<212> TYPE: DNA
<213> ORGANISM: Homo sapiens

<400> SEQUENCE: 78
ggcctttcct tgttggcttt cggagatgat tccttgatag cgacgggaat gcatg    55

<210> SEQ ID NO 79
<211> LENGTH: 37
<212> TYPE: DNA
<213> ORGANISM: Homo sapiens

<400> SEQUENCE: 79
ctagcatgcg tcgctatcaa ggagccaaca tctccga    37

<210> SEQ ID NO 80
<211> LENGTH: 37
<212> TYPE: DNA
<213> ORGANISM: Homo sapiens

<400> SEQUENCE: 80
ggcctcggag atgttggctc cttgatagcg acgcatg                                37

<210> SEQ ID NO 81
<211> LENGTH: 25
<212> TYPE: DNA
<213> ORGANISM: Homo sapiens

<400> SEQUENCE: 81
cccagaaggt gagaaagttg aaatt                                             25

<210> SEQ ID NO 82
<211> LENGTH: 23
<212> TYPE: DNA
<213> ORGANISM: Homo sapiens

<400> SEQUENCE: 82
tcatcgagga tttccttgtt ggc                                               23

<210> SEQ ID NO 83
<211> LENGTH: 18
<212> TYPE: RNA
<213> ORGANISM: Artificial
<220> FEATURE:
<223> OTHER INFORMATION: human EGFR siRNA

<400> SEQUENCE: 83
gcucaucaug caccucau                                                     18

<210> SEQ ID NO 84
<211> LENGTH: 18
<212> TYPE: RNA
<213> ORGANISM: Artificial
<220> FEATURE:
<223> OTHER INFORMATION: human EGFR siRNA

<400> SEQUENCE: 84
augaggugca ugaugagc                                                     18

<210> SEQ ID NO 85
<211> LENGTH: 18
<212> TYPE: RNA
<213> ORGANISM: Artificial
<220> FEATURE:
<223> OTHER INFORMATION: human EGFR siRNA

<400> SEQUENCE: 85
gcucaucaug cagcacau                                                     18

<210> SEQ ID NO 86
<211> LENGTH: 18
<212> TYPE: RNA
<213> ORGANISM: Artificial
<220> FEATURE:
<223> OTHER INFORMATION: human EGFR siRNA

<400> SEQUENCE: 86
augugcugca ugaugagc                                                     18

<210> SEQ ID NO 87
<211> LENGTH: 18
<212> TYPE: RNA
<213> ORGANISM: Homo sapiens

<400> SEQUENCE: 87

-continued

```
gcucaucaug cagcucau                                              18

<210> SEQ ID NO 88
<211> LENGTH: 18
<212> TYPE: RNA
<213> ORGANISM: Homo sapiens

<400> SEQUENCE: 88
augagcugca ugaugagc                                              18

<210> SEQ ID NO 89
<211> LENGTH: 18
<212> TYPE: RNA
<213> ORGANISM: Homo sapiens

<400> SEQUENCE: 89
agcucaucau gcagcuca                                              18

<210> SEQ ID NO 90
<211> LENGTH: 18
<212> TYPE: RNA
<213> ORGANISM: Homo sapiens

<400> SEQUENCE: 90
ugagcugcau gaugagcu                                              18

<210> SEQ ID NO 91
<211> LENGTH: 18
<212> TYPE: RNA
<213> ORGANISM: Homo sapiens

<400> SEQUENCE: 91
cagcucauca ugcagcuc                                              18

<210> SEQ ID NO 92
<211> LENGTH: 18
<212> TYPE: RNA
<213> ORGANISM: Homo sapiens

<400> SEQUENCE: 92
gagcugcaug augagcug                                              18

<210> SEQ ID NO 93
<211> LENGTH: 19
<212> TYPE: RNA
<213> ORGANISM: Homo sapiens

<400> SEQUENCE: 93
uuuaagcaga guucaacuc                                             19

<210> SEQ ID NO 94
<211> LENGTH: 19
<212> TYPE: RNA
<213> ORGANISM: Homo sapiens

<400> SEQUENCE: 94
gaguugaacu cugcuuaaa                                             19

<210> SEQ ID NO 95
<211> LENGTH: 19
<212> TYPE: RNA
<213> ORGANISM: Homo sapiens

<400> SEQUENCE: 95
```

```
uuaagcagag uucaacucu                                          19

<210> SEQ ID NO 96
<211> LENGTH: 19
<212> TYPE: RNA
<213> ORGANISM: Homo sapiens

<400> SEQUENCE: 96
agaguugaac ucugcuuaa                                          19

<210> SEQ ID NO 97
<211> LENGTH: 19
<212> TYPE: RNA
<213> ORGANISM: Homo sapiens

<400> SEQUENCE: 97
uaagcagagu ucaacucua                                          19

<210> SEQ ID NO 98
<211> LENGTH: 19
<212> TYPE: RNA
<213> ORGANISM: Homo sapiens

<400> SEQUENCE: 98
uagaguugaa cucugcuua                                          19

<210> SEQ ID NO 99
<211> LENGTH: 19
<212> TYPE: RNA
<213> ORGANISM: Homo sapiens

<400> SEQUENCE: 99
aagcagaguu caacucuac                                          19

<210> SEQ ID NO 100
<211> LENGTH: 19
<212> TYPE: RNA
<213> ORGANISM: Homo sapiens

<400> SEQUENCE: 100
guagaguuga acucugcuu                                          19

<210> SEQ ID NO 101
<211> LENGTH: 19
<212> TYPE: RNA
<213> ORGANISM: Homo sapiens

<400> SEQUENCE: 101
agcagaguuc aacucuacg                                          19

<210> SEQ ID NO 102
<211> LENGTH: 19
<212> TYPE: RNA
<213> ORGANISM: Homo sapiens

<400> SEQUENCE: 102
cguagaguug aacucugcu                                          19

<210> SEQ ID NO 103
<211> LENGTH: 19
<212> TYPE: RNA
<213> ORGANISM: Homo sapiens
```

```
<400> SEQUENCE: 103
gcagaguuca acucuacgu                                                    19

<210> SEQ ID NO 104
<211> LENGTH: 19
<212> TYPE: RNA
<213> ORGANISM: Homo sapiens

<400> SEQUENCE: 104
acguagaguu gaacucugc                                                    19

<210> SEQ ID NO 105
<211> LENGTH: 19
<212> TYPE: RNA
<213> ORGANISM: Homo sapiens

<400> SEQUENCE: 105
cagaguucaa cucuacguc                                                    19

<210> SEQ ID NO 106
<211> LENGTH: 19
<212> TYPE: RNA
<213> ORGANISM: Homo sapiens

<400> SEQUENCE: 106
gacguagagu ugaacucug                                                    19

<210> SEQ ID NO 107
<211> LENGTH: 19
<212> TYPE: RNA
<213> ORGANISM: Homo sapiens

<400> SEQUENCE: 107
agaguucaac ucuacgucu                                                    19

<210> SEQ ID NO 108
<211> LENGTH: 19
<212> TYPE: RNA
<213> ORGANISM: Homo sapiens

<400> SEQUENCE: 108
agacguagag uugaacucu                                                    19

<210> SEQ ID NO 109
<211> LENGTH: 19
<212> TYPE: RNA
<213> ORGANISM: Homo sapiens

<400> SEQUENCE: 109
gaguucaacu cuacgucuc                                                    19

<210> SEQ ID NO 110
<211> LENGTH: 19
<212> TYPE: RNA
<213> ORGANISM: Homo sapiens

<400> SEQUENCE: 110
gagacguaga guugaacuc                                                    19

<210> SEQ ID NO 111
<211> LENGTH: 19
<212> TYPE: RNA
<213> ORGANISM: Homo sapiens
```

<400> SEQUENCE: 111
aguucaacuc uacgucucc                                            19

<210> SEQ ID NO 112
<211> LENGTH: 19
<212> TYPE: RNA
<213> ORGANISM: Homo sapiens

<400> SEQUENCE: 112
ggagacguag aguugaacu                                            19

<210> SEQ ID NO 113
<211> LENGTH: 19
<212> TYPE: RNA
<213> ORGANISM: Homo sapiens

<400> SEQUENCE: 113
guucaacucu acgucuccu                                            19

<210> SEQ ID NO 114
<211> LENGTH: 19
<212> TYPE: RNA
<213> ORGANISM: Homo sapiens

<400> SEQUENCE: 114
aggagacgua gaguugaac                                            19

<210> SEQ ID NO 115
<211> LENGTH: 19
<212> TYPE: RNA
<213> ORGANISM: Homo sapiens

<400> SEQUENCE: 115
uucaacucua cgucuccuc                                            19

<210> SEQ ID NO 116
<211> LENGTH: 19
<212> TYPE: RNA
<213> ORGANISM: Homo sapiens

<400> SEQUENCE: 116
gaggagacgu agaguugaa                                            19

<210> SEQ ID NO 117
<211> LENGTH: 19
<212> TYPE: RNA
<213> ORGANISM: Homo sapiens

<400> SEQUENCE: 117
ucaacucuac gucuccucc                                            19

<210> SEQ ID NO 118
<211> LENGTH: 19
<212> TYPE: RNA
<213> ORGANISM: Homo sapiens

<400> SEQUENCE: 118
ggaggagacg uagaguuga                                            19

<210> SEQ ID NO 119
<211> LENGTH: 19
<212> TYPE: RNA

<213> ORGANISM: Homo sapiens

<400> SEQUENCE: 119
caacucuacg ucuccuccg          19

<210> SEQ ID NO 120
<211> LENGTH: 19
<212> TYPE: RNA
<213> ORGANISM: Homo sapiens

<400> SEQUENCE: 120
cggaggagac guagaguug          19

<210> SEQ ID NO 121
<211> LENGTH: 42
<212> TYPE: DNA
<213> ORGANISM: Homo sapiens

<400> SEQUENCE: 121
ctagcatgct ttaagcagag ttcaactcta cgtctcctcc ga          42

<210> SEQ ID NO 122
<211> LENGTH: 42
<212> TYPE: DNA
<213> ORGANISM: Homo sapiens

<400> SEQUENCE: 122
ggcctcggag gagacgtaga gttgaactct gcttaaagca tg          42

<210> SEQ ID NO 123
<211> LENGTH: 42
<212> TYPE: DNA
<213> ORGANISM: Homo sapiens

<400> SEQUENCE: 123
ctagcatgct gcttctgatg gcaagctcta cgtctcctcc ga          42

<210> SEQ ID NO 124
<211> LENGTH: 42
<212> TYPE: DNA
<213> ORGANISM: Homo sapiens

<400> SEQUENCE: 124
ggcctcggag gagacgtaga gcttgccatc agaagcagca tg          42

<210> SEQ ID NO 125
<211> LENGTH: 43
<212> TYPE: DNA
<213> ORGANISM: Homo sapiens

<400> SEQUENCE: 125
ctagcatgct ttaagcagag ttcaaatctg tactgcaccc tga          43

<210> SEQ ID NO 126
<211> LENGTH: 43
<212> TYPE: DNA
<213> ORGANISM: Homo sapiens

<400> SEQUENCE: 126
ggcctcaggg tgcagtacag atttgaactc tgcttaaagc atg          43

<210> SEQ ID NO 127
<211> LENGTH: 21

```
<212> TYPE: RNA
<213> ORGANISM: Artificial
<220> FEATURE:
<223> OTHER INFORMATION: human EGFR siRNA

<400> SEQUENCE: 127
ggagggacau cguccaaaau u                                          21

<210> SEQ ID NO 128
<211> LENGTH: 21
<212> TYPE: RNA
<213> ORGANISM: Artificial
<220> FEATURE:
<223> OTHER INFORMATION: human EGFR siRNA

<400> SEQUENCE: 128
uuuuggacga ugcccuccu u                                           21

<210> SEQ ID NO 129
<211> LENGTH: 19
<212> TYPE: RNA
<213> ORGANISM: Artificial
<220> FEATURE:
<223> OTHER INFORMATION: human EGFR siRNA

<400> SEQUENCE: 129
cgucgcuauc aaggaacca                                             19

<210> SEQ ID NO 130
<211> LENGTH: 19
<212> TYPE: RNA
<213> ORGANISM: Artificial
<220> FEATURE:
<223> OTHER INFORMATION: human EGFR siRNA

<400> SEQUENCE: 130
ugcuuccuug auagcgacg                                             19

<210> SEQ ID NO 131
<211> LENGTH: 19
<212> TYPE: RNA
<213> ORGANISM: Artificial
<220> FEATURE:
<223> OTHER INFORMATION: human EGFR siRNA

<400> SEQUENCE: 131
gucgcuauca aggaaccaa                                             19

<210> SEQ ID NO 132
<211> LENGTH: 19
<212> TYPE: RNA
<213> ORGANISM: Artificial
<220> FEATURE:
<223> OTHER INFORMATION: human EGFR siRNA

<400> SEQUENCE: 132
uugcuuccuu gauagcgac                                             19

<210> SEQ ID NO 133
<211> LENGTH: 19
<212> TYPE: RNA
<213> ORGANISM: Artificial
<220> FEATURE:
<223> OTHER INFORMATION: human EGFR siRNA

<400> SEQUENCE: 133
```
ucgcuaucaa ggaaccaac                                                                19

<210> SEQ ID NO 134
<211> LENGTH: 19
<212> TYPE: RNA
<213> ORGANISM: Artificial
<220> FEATURE:
<223> OTHER INFORMATION: human EGFR siRNA

<400> SEQUENCE: 134
guugcuuccu ugauagcga                                                                19

<210> SEQ ID NO 135
<211> LENGTH: 19
<212> TYPE: RNA
<213> ORGANISM: Artificial
<220> FEATURE:
<223> OTHER INFORMATION: human EGFR siRNA

<400> SEQUENCE: 135
cgcuaucaag gaaccaaca                                                                19

<210> SEQ ID NO 136
<211> LENGTH: 19
<212> TYPE: RNA
<213> ORGANISM: Artificial
<220> FEATURE:
<223> OTHER INFORMATION: human EGFR siRNA

<400> SEQUENCE: 136
uguugcuucc uugauagcg                                                                19

<210> SEQ ID NO 137
<211> LENGTH: 19
<212> TYPE: RNA
<213> ORGANISM: Artificial
<220> FEATURE:
<223> OTHER INFORMATION: human EGFR siRNA

<400> SEQUENCE: 137
gcuaucaagg aaccaacau                                                                19

<210> SEQ ID NO 138
<211> LENGTH: 19
<212> TYPE: RNA
<213> ORGANISM: Artificial
<220> FEATURE:
<223> OTHER INFORMATION: human EGFR siRNA

<400> SEQUENCE: 138
auguugcuuc cuugauagc                                                                19

<210> SEQ ID NO 139
<211> LENGTH: 19
<212> TYPE: RNA
<213> ORGANISM: Artificial
<220> FEATURE:
<223> OTHER INFORMATION: human EGFR siRNA

<400> SEQUENCE: 139
cuaucaagga accaacauc                                                                19

<210> SEQ ID NO 140
<211> LENGTH: 19
<212> TYPE: RNA
<213> ORGANISM: Artificial

```
<220> FEATURE:
<223> OTHER INFORMATION: human EGFR siRNA

<400> SEQUENCE: 140
gauguugcuu ccuugauag                                              19

<210> SEQ ID NO 141
<211> LENGTH: 19
<212> TYPE: RNA
<213> ORGANISM: Artificial
<220> FEATURE:
<223> OTHER INFORMATION: human EGFR siRNA

<400> SEQUENCE: 141
uaucaaggaa ccaacaucu                                              19

<210> SEQ ID NO 142
<211> LENGTH: 19
<212> TYPE: RNA
<213> ORGANISM: Artificial
<220> FEATURE:
<223> OTHER INFORMATION: human EGFR siRNA

<400> SEQUENCE: 142
agauguugcu uccuugaua                                              19

<210> SEQ ID NO 143
<211> LENGTH: 19
<212> TYPE: RNA
<213> ORGANISM: Artificial
<220> FEATURE:
<223> OTHER INFORMATION: human EGFR siRNA

<400> SEQUENCE: 143
aucaaggaac caacaucuc                                              19

<210> SEQ ID NO 144
<211> LENGTH: 19
<212> TYPE: RNA
<213> ORGANISM: Artificial
<220> FEATURE:
<223> OTHER INFORMATION: human EGFR siRNA

<400> SEQUENCE: 144
gagauguugc uuccuugau                                              19

<210> SEQ ID NO 145
<211> LENGTH: 19
<212> TYPE: RNA
<213> ORGANISM: Artificial
<220> FEATURE:
<223> OTHER INFORMATION: human EGFR siRNA

<400> SEQUENCE: 145
ucaaggaacc aacaucucc                                              19

<210> SEQ ID NO 146
<211> LENGTH: 19
<212> TYPE: RNA
<213> ORGANISM: Artificial
<220> FEATURE:
<223> OTHER INFORMATION: human EGFR siRNA

<400> SEQUENCE: 146
ggagauguug cuuccuuga                                              19
```

<210> SEQ ID NO 147
<211> LENGTH: 37
<212> TYPE: DNA
<213> ORGANISM: Homo sapiens

<400> SEQUENCE: 147
ctagcatgcg tcgctatcaa ggaaccaaca tctccga         37

<210> SEQ ID NO 148
<211> LENGTH: 37
<212> TYPE: DNA
<213> ORGANISM: Homo sapiens

<400> SEQUENCE: 148
ggcctcggag atgttggttc cttgatagcg acgcatg         37

<210> SEQ ID NO 149
<211> LENGTH: 11
<212> TYPE: PRT
<213> ORGANISM: Homo sapiens

<400> SEQUENCE: 149

Ile Lys Glu Leu Arg Glu Ala Thr Ser Pro Lys
1               5                   10

<210> SEQ ID NO 150
<211> LENGTH: 33
<212> TYPE: DNA
<213> ORGANISM: Homo sapiens

<400> SEQUENCE: 150
atcaaggaat taagagaagc aacatctccg aaa             33

<210> SEQ ID NO 151
<211> LENGTH: 6
<212> TYPE: PRT
<213> ORGANISM: Homo sapiens

<400> SEQUENCE: 151

Ile Lys Thr Ser Pro Lys
1               5

<210> SEQ ID NO 152
<211> LENGTH: 18
<212> TYPE: DNA
<213> ORGANISM: Homo sapiens

<400> SEQUENCE: 152
atcaaaacat ctccgaaa                              18

<210> SEQ ID NO 153
<211> LENGTH: 7
<212> TYPE: PRT
<213> ORGANISM: Homo sapiens

<400> SEQUENCE: 153

Ile Lys Glu Ser Ser Pro Lys
1               5

<210> SEQ ID NO 154
<211> LENGTH: 21
<212> TYPE: DNA
<213> ORGANISM: Homo sapiens

```
<400> SEQUENCE: 154
atcaaggaat catctccgaa a                                           21

<210> SEQ ID NO 155
<211> LENGTH: 8
<212> TYPE: PRT
<213> ORGANISM: Homo sapiens

<400> SEQUENCE: 155

Ile Lys Glu Pro Thr Ser Pro Lys
1               5

<210> SEQ ID NO 156
<211> LENGTH: 24
<212> TYPE: DNA
<213> ORGANISM: Homo sapiens

<400> SEQUENCE: 156
atcaaggagc aacatctcc gaaa                                         24

<210> SEQ ID NO 157
<211> LENGTH: 8
<212> TYPE: PRT
<213> ORGANISM: Homo sapiens

<400> SEQUENCE: 157

Ile Lys Glu Pro Thr Ser Pro Lys
1               5

<210> SEQ ID NO 158
<211> LENGTH: 24
<212> TYPE: DNA
<213> ORGANISM: Homo sapiens

<400> SEQUENCE: 158
atcaaggaac caacatctcc gaaa                                        24

<210> SEQ ID NO 159
<211> LENGTH: 10
<212> TYPE: PRT
<213> ORGANISM: Homo sapiens

<400> SEQUENCE: 159

Ala Ser Asp Gly Lys Leu Tyr Val Ser Ser
1               5                   10

<210> SEQ ID NO 160
<211> LENGTH: 30
<212> TYPE: DNA
<213> ORGANISM: Homo sapiens

<400> SEQUENCE: 160
gcttctgatg gcaagctcta cgtctcctcc                                  30

<210> SEQ ID NO 161
<211> LENGTH: 10
<212> TYPE: PRT
<213> ORGANISM: Homo sapiens

<400> SEQUENCE: 161

Phe Lys Gln Ser Ser Thr Leu Arg Leu Leu
1               5                   10
```

```
<210> SEQ ID NO 162
<211> LENGTH: 30
<212> TYPE: DNA
<213> ORGANISM: Homo sapiens

<400> SEQUENCE: 162
tttaagcaga gttcaactct acgtctcctc                                     30

<210> SEQ ID NO 163
<211> LENGTH: 10
<212> TYPE: PRT
<213> ORGANISM: Homo sapiens

<400> SEQUENCE: 163

Phe Lys Gln Ser Ser Asn Leu Tyr Cys Thr
1               5                   10

<210> SEQ ID NO 164
<211> LENGTH: 30
<212> TYPE: DNA
<213> ORGANISM: Homo sapiens

<400> SEQUENCE: 164
tttaagcaga gttcaaatct gtactgcacc                                     30

<210> SEQ ID NO 165
<211> LENGTH: 5
<212> TYPE: PRT
<213> ORGANISM: Homo sapiens

<400> SEQUENCE: 165

Leu Ile Thr Gln Leu
1               5

<210> SEQ ID NO 166
<211> LENGTH: 15
<212> TYPE: DNA
<213> ORGANISM: Homo sapiens

<400> SEQUENCE: 166
ctcatcacgc agctc                                                     15

<210> SEQ ID NO 167
<211> LENGTH: 5
<212> TYPE: PRT
<213> ORGANISM: Homo sapiens

<400> SEQUENCE: 167

Leu Ile Met Gln Leu
1               5

<210> SEQ ID NO 168
<211> LENGTH: 15
<212> TYPE: DNA
<213> ORGANISM: Homo sapiens

<400> SEQUENCE: 168
ctcatcatgc agctc                                                     15
```